United States Patent
Roberts et al.

(10) Patent No.: US 12,227,529 B2
(45) Date of Patent: Feb. 18, 2025

(54) METHOD OF PREPARING SILANOLS WITH SELECTIVE CYTOCHROME P450 VARIANTS AND RELATED COMPOUNDS AND COMPOSITIONS

(71) Applicants: DOW SILICONES CORPORATION, Midland, MI (US); CALIFORNIA INSTITUTE OF TECHNOLOGY, Pasadena, CA (US)

(72) Inventors: John Roberts, Midland, MI (US); Dimitris Elias Katsoulis, Midland, MI (US); Susanne Baehr, Pasadena, CA (US); Sabine Brinkmann-Chen, Pasadena, CA (US); S. B. Jennifer Kan, Pasadena, CA (US); Frances H. Arnold, Pasadena, CA (US)

(73) Assignees: DOW SILICONES CORPORATION, Midland, MI (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 238 days.

(21) Appl. No.: 17/800,211

(22) PCT Filed: Feb. 19, 2021

(86) PCT No.: PCT/US2021/018749
§ 371 (c)(1),
(2) Date: Aug. 16, 2022

(87) PCT Pub. No.: WO2021/168228
PCT Pub. Date: Aug. 26, 2021

(65) Prior Publication Data
US 2023/0102728 A1    Mar. 30, 2023

Related U.S. Application Data

(60) Provisional application No. 62/979,960, filed on Feb. 21, 2020.

(51) Int. Cl.
*C07F 7/08* (2006.01)
(52) U.S. Cl.
CPC .................. *C07F 7/0836* (2013.01)
(58) Field of Classification Search
CPC .... C07F 7/0836; C07F 7/0896; C12N 9/0071; C12Y 114/14001
See application file for complete search history.

(56) References Cited

U.S. PATENT DOCUMENTS

| | | | |
|---|---|---|---|
| 7,524,664 B2 * | 4/2009 | Arnold .................. | C12N 9/0077 435/71.1 |
| 2006/0216802 A1 | 9/2006 | Hauer et al. | |
| 2017/0218346 A1 | 8/2017 | Kan et al. | |
| 2022/0098222 A1 | 3/2022 | Eldred et al. | |

FOREIGN PATENT DOCUMENTS

WO    2004099398 A1    11/2004

OTHER PUBLICATIONS

G. H. Barnes, Jr., N. E. J. Daughenbaugh, Organosilanols via Reaction of Organosilicon Hydrides with Water. J. Org. Chem. 1966, 31, 885-887.
M. Shi, K. M. Nicholas, Catalytic Dehydrocoupling of Silane by a Homogenous Rhodium Complex with Water. J. Chem. Res. (S), 1997, 400-401.
Yu, M.; Jing, H.; Liu, X.; Fu, X. Visible-Light-Promoted Generation of Hydrogen from the Hydrolysis of Silanes Catalyzed by Rhodium(III) Porphyrins. Organometallics 2015, 34, 5754-5758.
Y. Kikukawa, Y. Kuroda, K. Yamaguchi, N. Mizuno, Diamond-Shaped [Ag4]4+ Cluster Encapsulated by Silicotungstate Ligands: Synthesis and Catalysis of Hydrolytic Oxidation of Silanes. Angew. Chem. Int. Ed. 2012, 51, 2434-2437.
Y. Lee, D. Seomoon, S. Kim, H. Han, S. Chang, P. H. Lee, Highly Efficient Iridium-Catalyzed Oxidation of Organosilanes to Silanols. J. Org. Chem. 2004, 69, 1741-1743.
E. A. Ison, R. A. Corbin, M. M. Abu-Omar, Hydrogen Production from Hydrolytic Oxidation of Organosilanes Using a Cationic Oxorhenium Catalyst. J. Am. Chem. Soc. 2005, 127, 11938-11939.
E. Matarasso-Tchiroukhine, AreneCr(CO)2(n2-HSiHPh2) Complexes as Catalysts for the Si—H Bond Activation. Hydrolysis of the Si—H Bond and Dehydrogenative Coupling between Diphenylsilane and Nucleophiles. J. Chem. Soc., Chem. Commun 1990, 681-682.
J. Schubert, C. Lorenz, Conversion of Hydrosilanes to Silanols and Silyl Esters Catalyzed by [Ph3PCuH]6. Inorg. Chem. 1997, 36, 1258-1259.
A. K. Liang Teo, W. Y. Fan, A novel iron complex for highly efficient catalytic hydrogen generation from the hydrolysis of organosilanes. Chem. Commun. 2014, 50, 7191-7194.
Y. Okada, M. Oba, A. Arai, K. Tanaka, K. Nishiyama, W. Ando, Diorganotelluride-Catalyzed Oxidation of Silanes to Silanols under Atmospheric Oxygen. Inorg. Chem. 2010, 49, 383-385.
W. Adam, H. Garcia, C. M. Mitchell, C. R. Saha-Moller, O. Weichold, The selective catalytic oxidation of silanes to silanols with H2O2 activated by the Ti-beta zeolite Chem. Commun. 1998, 2609-2610.

(Continued)

*Primary Examiner* — Pancham Bakshi
(74) *Attorney, Agent, or Firm* — Warner Norcross + Judd LLP

(57) ABSTRACT

This disclosure provides a method of preparing a silanol-functional organosilicon compound with a cytochrome P450 variant that facilitates the oxidization of a silyl hydride group to a silanol group in the presence of oxygen. The method includes combining the cytochrome P450 variant and an organosilicon compound having at least one silicon-bonded hydrogen atom to give a reaction mixture and exposing the reaction mixture to oxygen to oxidize the organosilicon compound, thereby preparing the silanol-functional organosilicon compound. Cytochrome P450 variants suitable for use in the method are also disclosed, along with methods for engineering and optimizing the same. Nucleic acids encoding the cytochrome P450 variants and compositions, expression vectors, and host cells including the same are also disclosed.

20 Claims, 16 Drawing Sheets
Specification includes a Sequence Listing.

(56) References Cited

OTHER PUBLICATIONS

D. Limnios, C. G. Kokotos, Organocatalytic Oxidation of Organosilanes to Silanols. ACS Catal. 2013, 3, 2239-2243.
P. Manikandan, S. Nagini, Cytochrome P450 Structure, Function and Clinical Significance: A Review. Curr. Drug. Targets. 2018, 19, 38-54.
C. J. C. Whitehouse, S. G. Bell, L.-L. Wong, P450BM3 (CYP102A1): Connecting the dots. Chem. Soc. Rev. 2012, 41, 1218-1260.
E. M. Isin, F. P. Guengerich, Complex reactions catalyzed by cytochrome P450 enzymes. Biochim. Biophys. Acta. 2007, 3, 314-329.
P. R. Ortiz de Montellano, Hydrocarbon Hydroxylation by Cytochrome P450 Enzymes. Chem Rev. 2010, 110, 932-948.
S. Shaik, S. Cohen, Y. Wang, H. Chen, D. Kumar, W. Thiel, P450 Enzymes: Their Structure, Reactivity, and Selectivity—Modeled by QM/MM Calculations. Chem. Rev. 2010, 210, 949-1017.
P. Treguer, D. M. Nelson, A. J. V. Bennekom, D. J. DeMaster, A. Leynaert, B. Quéguiner, The Silica Balance in the World's Oceans: A Reestimate. Science 1995, 268, 375-379.
M. B. Frampton, R. Simionescu, P. M. Zelisko, Enzyme-Mediated Synthesis of Silsesquioxanes. Silicon 2009, 1, 47-56.
V. Abbate, A. R. Bassindale, K. F. Brandstadt, R. Lawson, P. G. Taylor, Enzyme mediated silicon-oxygen bond formation; the use of Rhizopus oryzae lipase, lysozyme and phytase under mild conditions. Dalt. Trans. 2010, 39, 9361-9368.
V. Abbate, K. F. Brandstadt, P. G. Taylor, A. R. Bassindale, Enzyme-Catalyzed Transetherfication of Alkoxysilanes, Catalysts 2013, 3, 27-35.
S. Y. Tabatabaei Dakhili, S. A. Caslin, A. S. Faponle, P. Quayle, S. P. de Visser, L. Shin Wong, Recombinant silicateins as model biocatalysts in organosiloxane chemistry. Proc. Natl. Acad. Sci. U.S.A. 2017, 114, E5285-E5291.
M. B. Frampton, P. M. Zelisko, Biocatalysis in Silicon Chemistry. Chem. Asian J. 2017, 12, 1153-1167.
M. B. Frampton, P. M. Zelisko, Organosilicon Biotechnology. Silicon 2009, 1, 147-163.
S. B. J. Kan, R. D. Lewis, K. Chen, F. H. Arnold, Directed Evolution of Cytochrome c for Carbon-Silicon Bond Formation: Bringing Silicon to Life. Science 2016, 354, 1048-1051.
R. J. Fessenden, R. A. Hartman, Metabolic Fate of Phenyltrimethylsilane and Phenyldimethylsilane. J. Med. Chem. 1970, 13, 52-54.
S. T. Jung, R. Lauchli, F. H. Arnold, Cytochrome P450: taming a wild type enzyme. Curr. Op. Biotech. 2011, 22, 809-817.
H. Li, T. L. Poulos, Fatty acid metabolism, conformational change, and electron transfer in cytochrome P-450(BM-3). Biochim. Biophys. Acta 1999, 1441, 141-149.
D. C. Haines, D. R. Tomchick, M. Machius, J. A. Peterson, Pivotal role of water in the mechanism of P450BM-3. Biochemistry 2001, 40, 13456-13465.
S. Kille, C. G. Acevedo-Rocha, L. P. Parra, Z. G. Zhang, D. J. Opperman, M. T. Reetz, J. P. Acevedo, Reducing Codon Redundancy and Screening Effort of Combinatorial Protein Libraries Created by Saturation Mutagenesis. ACS Synth. Biol. 2013, 2, 83-92.
K. Zhang, B. M. Shafer, M. D. Denars II, H. A. Stern, R. Fasan, Controlled Oxidation of Remote sp3 C—H Bonds in Artemisinin via P450 Catalysis with Fine-Tuned Regio-and Stereoselectivity. J. Am. Chem. Soc. 2012, 134, 18695-18704.
R. J. P. Corriu, C. Guerin, Nucleophilic displacement at silicon sterochemistry and mechanistic implications, J. Organomet. Chem. 1980, 198, 231-320.
C. Chuit, R. J. P. Corriu, C. Reye, J. C. Young, Reactivity of penta- and hexacoordinate silicon compounds and their role as reaction intermediates. Chem. Rev. 1993, 93, 1371-1448.
R. Walsh, Bond Dissociation Energy Values in Silicon-Containing Compounds and Some of Their Implications. Acc. Chem. Res. 1981, 14, 246-252.
S. J. Blanksby, G. B. Ellison, Bond Dissociation Energies of Organic Molecules. Acc. Chem. Res. 2003, 36, 255-263.

C. Chatgilialoglu, Organosilanes as Radical-Based Reducing Agents in Synthesis. Acc. Chem. Res. 1992, 25, 188-194.
H. Zhou, B. Wang, F. Wang, X. Yu, L. Ma, A. Li, M. T. Reetz, Chemo-and Regioselective Dihydroxylation of Benzene to Hydroquinone Enabled by Engineered Cytochrome P450 Monooxygenase. Angew. Chem. Int. Ed. 2019, 58, 764-768 .
K. Wang, J. Zhou, Y. Jiang, M. Zhang, C. Wang, D. Xue, W. Tang, H. Sun, J. Xiao, C. Li, Selective Manganese-Catalyzed Oxidation of Hydrosilanes to Silanols under Neutral Reaction Conditions. Angew. Chem. Int. Ed. 2019, 58, 6380-6384.
G. Roiban, M. T. Reetz, Expanding the Toolbox of Organic Chemists: Directed Evolution of P450 Monooxygenases as Catalysts in Regio- and Stereoselective Oxidative Hydroxylation. Chem. Comm. 2015, 51, 2208-2224.
M. Lee, S. Ko, S. Chang, Highly Selective and Practical Hydrolytic Oxidation of Organosilanes to Silanols Catalyzed by a Ruthenium Complex. J. Am. Chem. Soc. 2000, 122, 48, 12011-12012.
J. Rittle, M. T. Green, M. T. Cytochrome P450 Compound I: Capture, Characterization, and C—H Bond Activation Kinetics. Science 2010, 330, 933-937.
International Search Report for PCT/US2021/018749 dated May 10, 2021, 4 pages.
Jeon et al., "Catalytic Synthesis of Silanols from Hydrosilanes and Applications", ACS Catalysis, vol. 2, No. 8 (2012) pp. 1539-1549.
Abbatte et al., "Enzyme mediated silicon-oxygen bond formation; the use of Rhizopus oryzae lipase, lysozyme and phytase under mild conditions", Dalton Transactions, 39(39), (2010) pp. 9361-9368.
Abbatte et al., "A large scale enzyme screen in the search for new methods of silicon-oxygen bond formation", Journal of Inorganic Biochemistry, 105(2), (2011) pp. 268-275.
Bahr et al., "Selective Enzymatic Oxidation of Silanes to Silanols", Angewandte Chemie International Edition, vol. 59, No. 36 (2020) pp. 15507-15511.
Kille et al., "Reducing Codon Redundancy and Screening Effort of Combinatorial Protein Libraries Created by Saturation Mutagenesis", American Chemical Society Synthetic Biology 2 (2013) pp. 83-92.
Sambrook et al., "Transformation of E. coli by Electroporation", Cold Spring Harbor Protocols 2006.1 (2006).
Lee et al., "Highly Selective and Practical Hydrolytic Oxidation of Organosilanes to Silanols Catalyzed by a Ruthenium Complex", J. Am. Chem. Soc. 122 (2000) pp. 12011-12012.
Tuokko et al. "Palladium on Charcoal Catalyzed 3,4-Hydroperoxidation of α-Substituted Enals with Triethylsilane and Water", Synlett, (2016) pp. 1649-1652.
Kan et al., "Directed Evolution of Cytochrome c for Carbon-Silicon Bond Formation: Bringing Silicon to Life", Sciencemag.org vol. 354, Issue 6315 (2016) pp. 1048-1051.
Dayal et al., "Effect of the Functionalization of the Axial Phthalocyanine Ligands on the Energy Transfer in QD-based Donor-Acceptor Pairs", Photochemistry and Photobiology 84 (2008) pp. 243-249.
Denmark et al., "Palladium-Catalyzed Cross-Coupling Reactions of Heterocyclic Silanolates with Substituted Aryl Lodides and Bromides", Organic Letters vol. 8, No. 4 (2006) pp. 793-795.
Denmark et al., "Palladium-Catalyzed Silylation of Aryl Bromides Leading to Functionalized Aryldimethylsilanols", Organic Letters vol. 5, No. 19 (2003) pp. 3483-3486.
Maya et al., "A Bentonite-Gold Nanohybrid as a Heterogeneous Green Catalyst for Selective Oxidation of Silanes", Chem. Commun. 52 (2016) pp. 10625-10628.
Hirabayashi et al., "A Facile Preparation and Cyclopropanation of 1-Alkenylsilanols", Bull. Chem. Soc. Jpn. 71 (1998) pp. 2409-2417.
Volkova et al., "Synthesis of Difunctional 1, 4-dimethyl-1, 4-Disilacyclohexanes", Russian Chemical Bulletin vol. 48 No. 9 (1999) pp. 1712-1716.
Guengerich et al., "Measurement of Cytochrome P450 and NADPH-Cytochrome P450 Reductase", Nature Protocols vol. 4 No. 9 (2009) pp. 1245-1251.
Studier, "Protein Production by Auto-Induction in High-Density Shaking Cultures", Protein Expression and Purification 41 (2005) pp. 207-234.
Gibson et al., "Enzymatic Assembly of DNA Molecules Up to Several Hundred Kilobases", Nature Methods, vol. 6, No. 5 (2009) pp. 343-347.

(56) References Cited

OTHER PUBLICATIONS

Fukuzumi et al., "P-450 Type Activation of Dioxygen by Heterogenized Metal Porphyrins: Comparison with the Corresponding Homogeneous Systems", Israel Journal of Chemistry, 28(1) (1987) pp. 29-36.

V. Chandrasekhar, R. Boomishankar, S. Nagendran, Recent Developments in the Synthesis and Structure of Organosilanols. Chem. Rev. 2004, 104, 5847-5910.

A. Colas, Silicones: Preparation, Properties and Performance; Dow Corning, Life Sciences, 2005.

S. E. Denmark, C. S. Regens, Palladium-Catalyzed Cross-Coupling Reactions of Organosilanols and their Salts: Practical Alternatives to Boron- and Tin-based Methods. Acc. Chem. Res. 2009, 41, 1486-1499.

M. Mewald, J. A. Schiffner, M. Oestreich, A New Direction in C—H Alkenylation: Silanol as a Helping Hand, Angew. Chem. Int. Ed. 2012, 51, 1763-1765.

S. E. Denmark, A. Ambrosi, Why You Really Should Consider Using Palladium-Catalyzed Cross-Coupling of Silanols and Silanolates. Org. Process Res. Dev. 2015, 19, 982-994.

K. M. Diemoz, J. E. Hein, S. O. Wilson, J. C. Fettinger, A. K. Franz, Reaction Progress Kinetics Analysis of 1,3-Disiloxanediols as Hydrogen-Bonding Catalysts. J. Org. Chem. 2017, 82, 6738-6747.

A. G. Schafer, J. M. Wieting, T. J. Fisher, A. E. Mattson, Chiral Silanediols in Anion-Binding Catalysis. Angew. Chem. Int. Ed., 2013, 52, 11321-11324.

A. K. Franz, S. O. Wilson, Organosilicon Molecules with Medicinal Applications. J. Med. Chem. 2013, 56, 388-405.

R. Ramesh, D. S. Reddy, Quest for Novel Chemical Entities through Incorporation of Silicon in Drug Scaffolds. J. Med. Chem. 2018, 61, 3779-3798.

James A. Cella, John C. Carpenter. Procedures for the preparation of silanols. Journal of Organometallic Chemistry 1994, 480 (1-2), 23-26.

P. D. Lickiss, R. Lucas, Oxidation of sterically hindered organosilicon hydrides using potassium permanganate. J. Organomet. Chem. 1995, 521, 229-234.

K. Valliant-Saunders, E. Gunn, G. R. Shelton, D. A. Hrovat, W. T. Borden, J. M. Mayer, Oxidation of Tertiary Silanes by Osmium Tetroxide. Inorg. Chem. 2007, 46, 5212-5219.

W. Adam, R. Mello, R. Curci, O-Atom Insertion into Si—H Bonds by Dioxiranes: A Stereospecific and Direct Conversion of Silanes into Silanols. Angew. Chem. Int. Ed. Engl. 1990, 29, 890-891.

L. H. Sommer, L. A. Ulland, G. A. Parker, Stereochemistry of Asymmetric Silicon. XX. Hydroxylation and Carbene Insertion Reactions of R3Si*H, J. Am. Chem. Soc. 1972, 94, 3469-3471.

* cited by examiner

FIG. 1
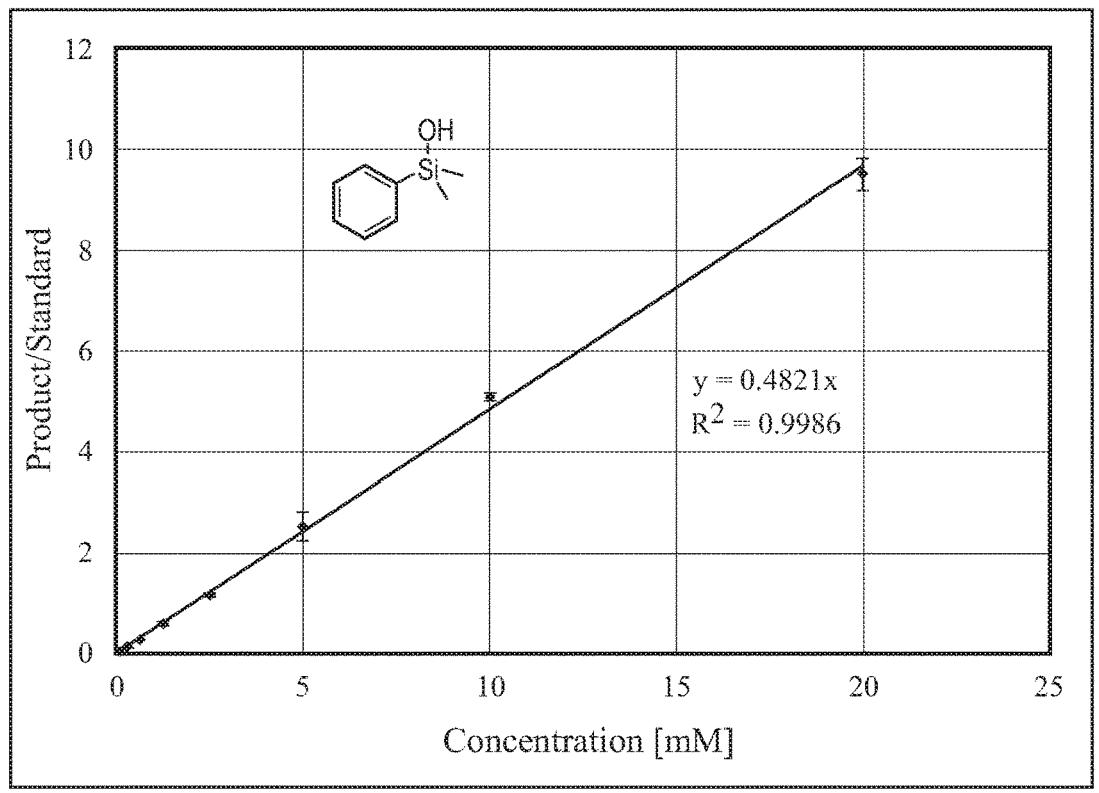
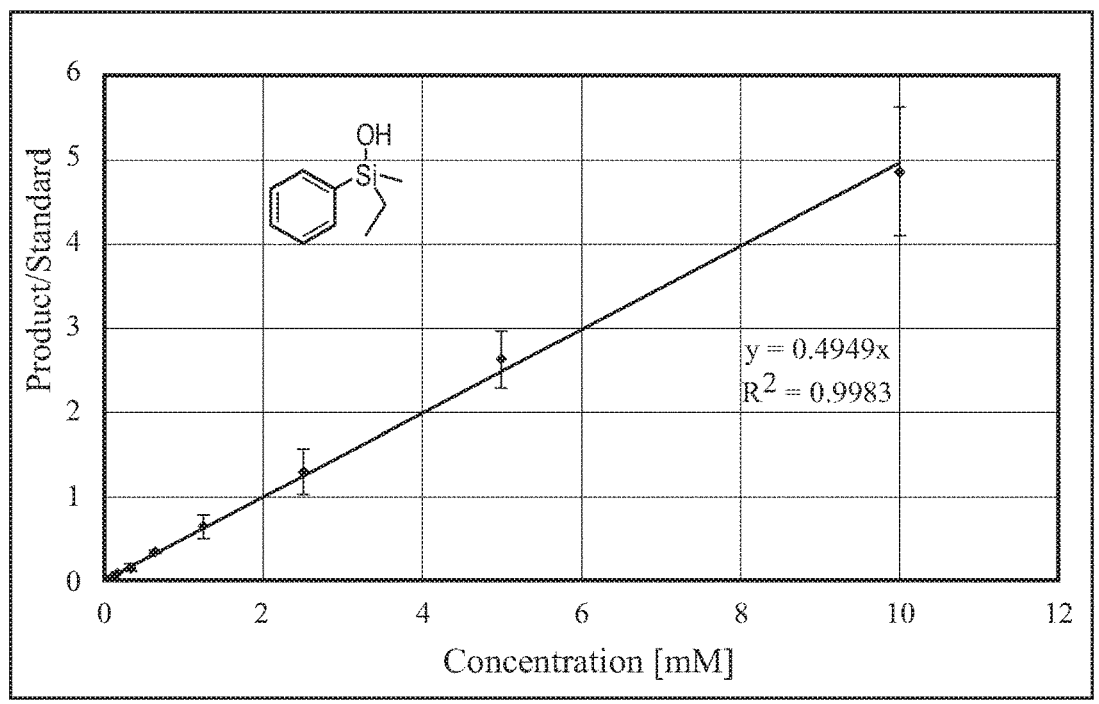
FIG. 2

FIG. 5
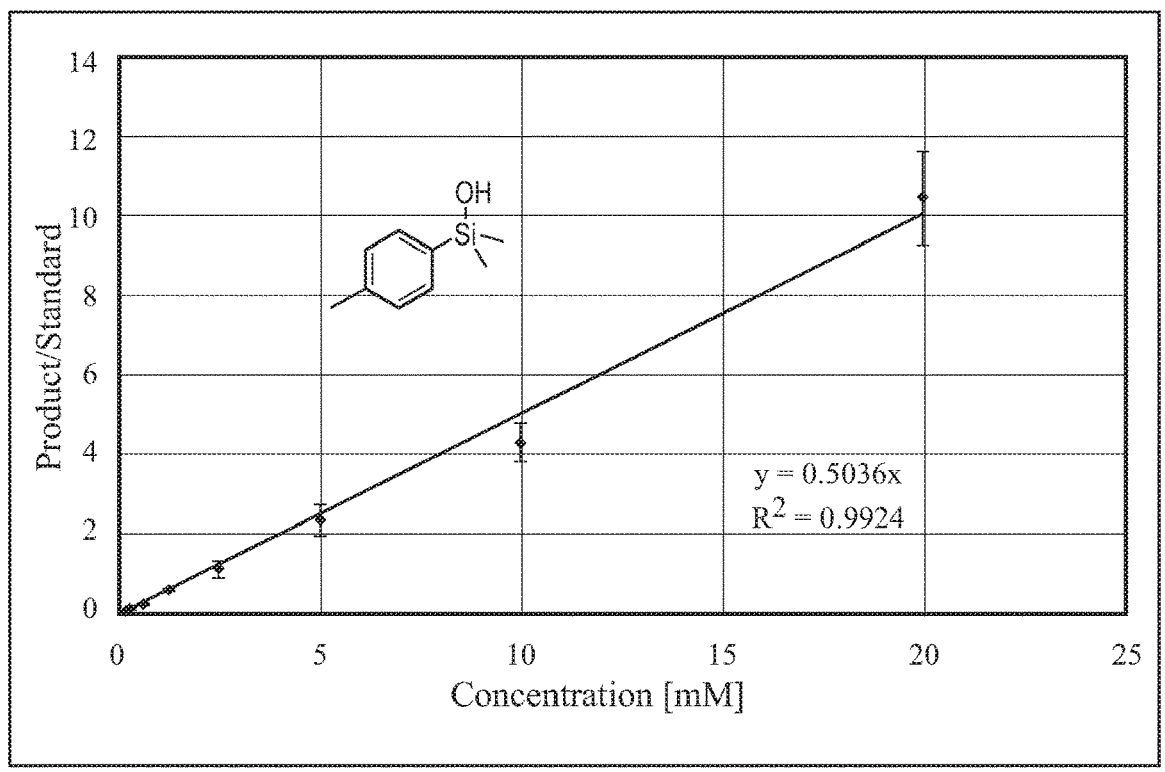
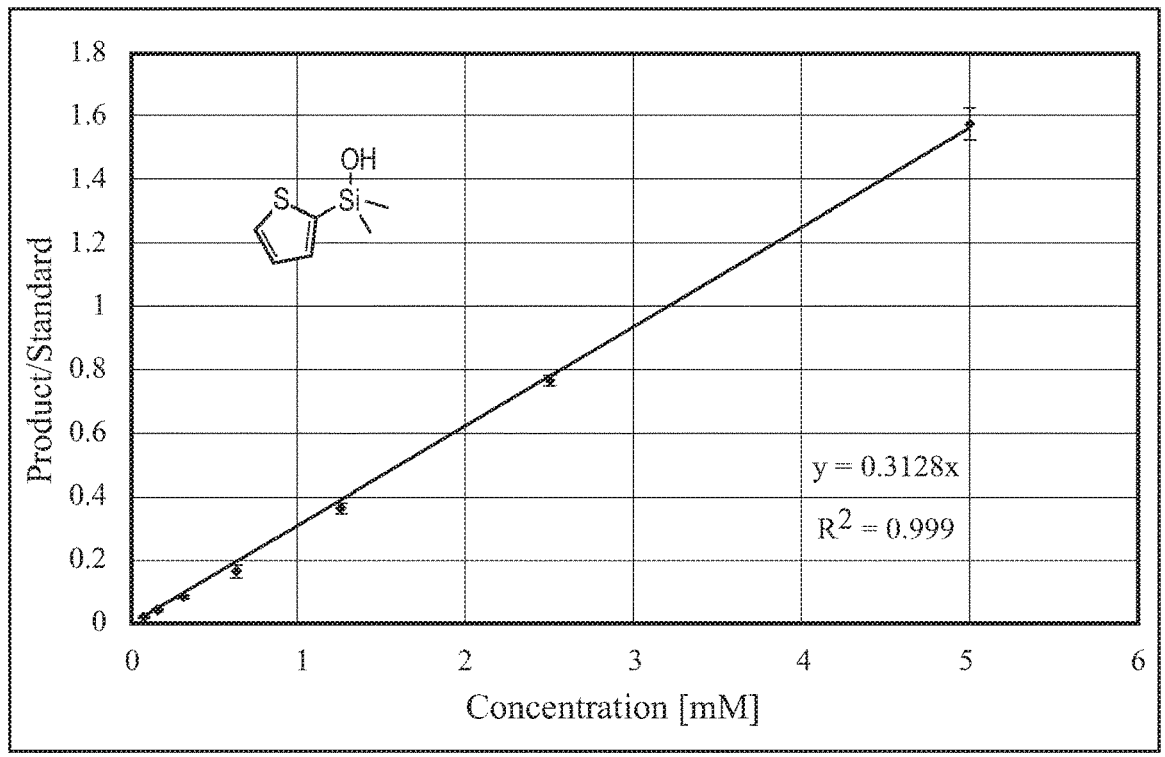
FIG. 6

FIG. 9
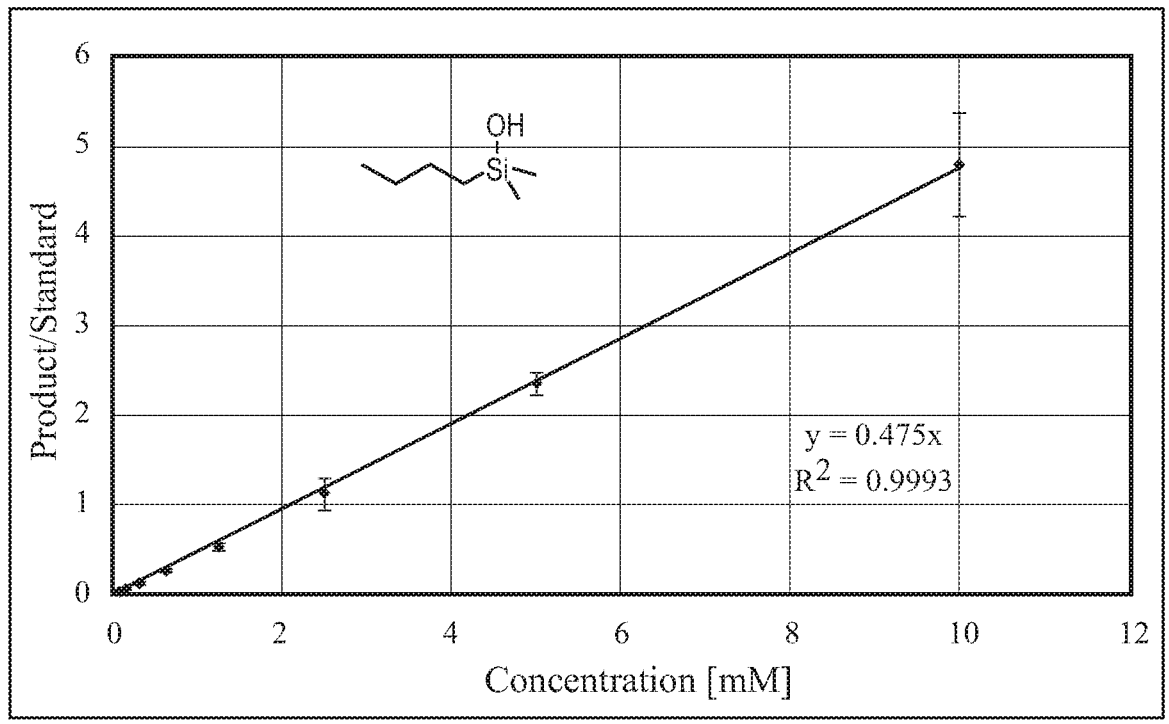
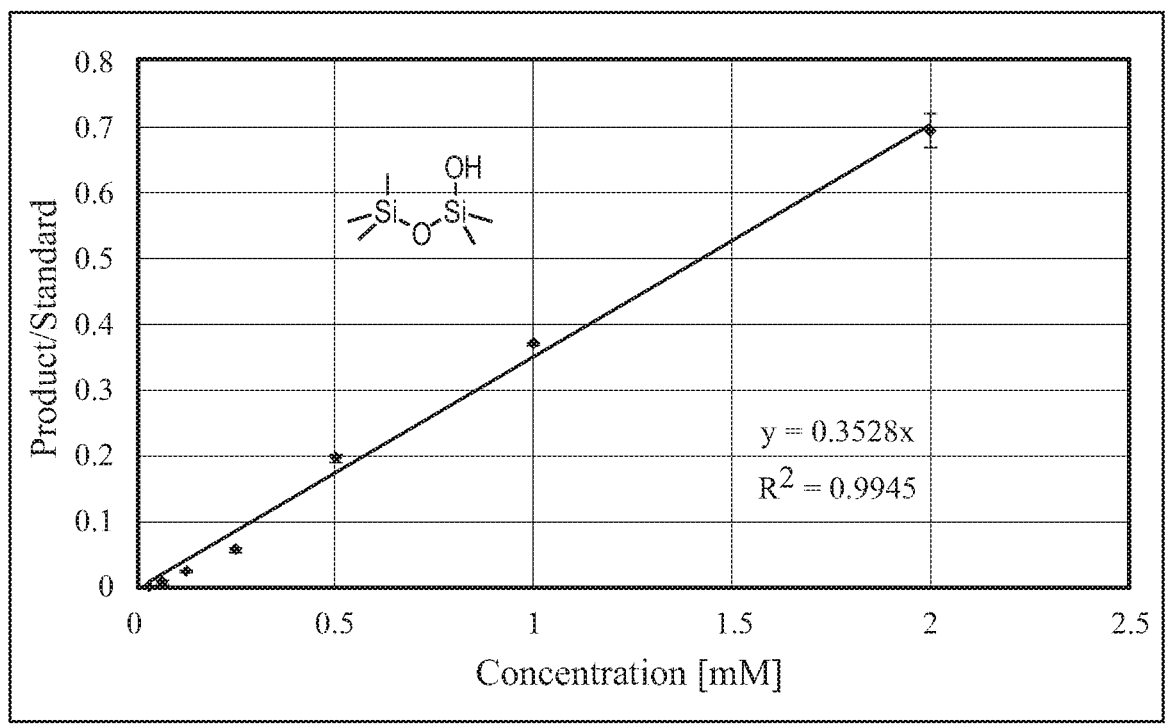
FIG. 10

SEQUENCE LISTING

```
<160> NUMBER OF SEQ ID NOS: 51

<210> SEQ ID NO 1
<211> LENGTH: 1049
<212> TYPE: PRT
<213> ORGANISM: Bacillus megaterium

<400> SEQUENCE: 1

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190
```

-continued

```
Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
```

```
                610             615             620
Val Ala Ala Tyr Phe Asn Leu Asp Ile Glu Asn Ser Glu Asp Asn Lys
625                     630             635                 640

Ser Thr Leu Ser Leu Gln Phe Val Asp Ser Ala Ala Asp Met Pro Leu
            645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680             685

Leu Pro Lys Glu Ala Ser Tyr Gln Glu Gly Asp His Leu Gly Val Ile
        690                 695             700

Pro Arg Asn Tyr Glu Gly Ile Val Asn Arg Val Thr Ala Arg Phe Gly
705                 710             715                 720

Leu Asp Ala Ser Gln Gln Ile Arg Leu Glu Ala Glu Glu Lys Leu
            725                 730             735

Ala His Leu Pro Leu Ala Lys Thr Val Ser Val Glu Glu Leu Leu Gln
            740                 745             750

Tyr Val Glu Leu Gln Asp Pro Val Thr Arg Thr Gln Leu Arg Ala Met
        755                 760             765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790             795                 800

Met Leu Glu Leu Leu Glu Lys Tyr Pro Ala Cys Glu Met Lys Phe Ser
            805                 810             815

Glu Phe Ile Ala Leu Leu Pro Ser Ile Arg Pro Arg Tyr Tyr Ser Ile
            820                 825             830

Ser Ser Ser Pro Arg Val Asp Glu Lys Gln Ala Ser Ile Thr Val Ser
            835                 840             845

Val Val Ser Gly Glu Ala Trp Ser Gly Tyr Gly Glu Tyr Lys Gly Ile
            850                 855             860

Ala Ser Asn Tyr Leu Ala Glu Leu Gln Glu Gly Asp Thr Ile Thr Cys
865                 870             875                 880

Phe Ile Ser Thr Pro Gln Ser Glu Phe Thr Leu Pro Lys Asp Pro Glu
            885                 890             895

Thr Pro Leu Ile Met Val Gly Pro Gly Thr Gly Val Ala Pro Phe Arg
            900                 905             910

Gly Phe Val Gln Ala Arg Lys Gln Leu Lys Glu Gln Gly Gln Ser Leu
            915                 920             925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950             955                 960

Leu His Thr Ala Phe Ser Arg Met Pro Asn Gln Pro Lys Thr Tyr Val
            965                 970             975

Gln His Val Met Glu Gln Asp Gly Lys Lys Leu Ile Glu Leu Leu Asp
            980                 985             990

Gln Gly Ala His Phe Tyr Ile Cys Gly Asp Gly Ser Gln Met Ala Pro
            995                 1000            1005

Ala Val Glu Ala Thr Leu Met Lys Ser Tyr Ala Asp Val His Gln
        1010            1015                1020

Val Ser Glu Ala Asp Ala Arg Leu Trp Leu Gln Gln Leu Glu Glu
        1025            1030                1035
```

Lys Gly Arg Tyr Ala Lys Asp Val Trp Ala Gly
    1040                1045

<210> SEQ ID NO 2
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Gly Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp

```
                340                 345                 350
Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765
```

```
Ala Ala Lys Thr Val Cys Pro Pro His Lys Val Glu Leu Glu Ala Leu
        770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 3
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
```

-continued

```
              65                  70                  75                  80
Asp Phe Ala Gly Asp Gly Leu Gly Thr Ser Trp Thr His Glu Lys Asn
                    85                  90                  95
Trp Lys Lys Ala His Asn Ile Leu Leu Pro Ser Phe Ser Gln Gln Ala
                   100                 105                 110
Met Lys Gly Tyr His Ala Met Val Asp Ile Ala Val Gln Leu Val
                   115                 120                 125
Gln Lys Trp Glu Arg Leu Asn Ala Asp Glu His Ile Glu Val Pro Glu
                   130                 135                 140
Asp Met Thr Arg Leu Thr Leu Asp Thr Ile Gly Leu Cys Gly Phe Asn
145                150                 155                 160
Tyr Arg Phe Asn Ser Phe Tyr Arg Asp Gln Pro His Pro Phe Ile Thr
                        165                 170                 175
Ser Met Val Arg Ala Leu Asp Glu Ala Met Asn Lys Leu Gln Arg Ala
                   180                 185                 190
Asn Pro Asp Asp Pro Ala Tyr Asp Glu Asn Lys Arg Gln Phe Gln Glu
                   195                 200                 205
Asp Ile Lys Val Met Asn Asp Leu Val Asp Lys Ile Ile Ala Asp Arg
210                215                 220
Lys Ala Ser Gly Glu Gln Ser Asp Asp Leu Leu Thr His Met Leu Asn
225                    230                 235                 240
Gly Lys Asp Pro Glu Thr Gly Glu Pro Leu Asp Asp Gly Asn Ile Arg
                   245                 250                 255
Tyr Gln Ile Ile Thr Phe Leu Ile Ala Gly His Glu Thr Thr Ser Gly
                        260                 265                 270
Leu Leu Ser Phe Ala Leu Tyr Phe Leu Val Lys Asn Pro His Val Leu
                   275                 280                 285
Gln Lys Ala Ala Glu Ala Ala Arg Val Leu Val Asp Pro Val Pro
                   290                 295                 300
Ser Tyr Lys Gln Val Lys Gln Leu Lys Tyr Val Gly Met Val Leu Asn
305                    310                 315                 320
Glu Ala Leu Arg Leu Trp Pro Thr Leu Pro Ala Phe Ser Leu Tyr Ala
                        325                 330                 335
Lys Glu Asp Thr Val Leu Gly Gly Glu Tyr Pro Leu Glu Lys Gly Asp
                   340                 345                 350
Glu Leu Met Val Leu Ile Pro Gln Leu His Arg Asp Lys Thr Ile Trp
                   355                 360                 365
Gly Asp Asp Val Glu Glu Phe Arg Pro Glu Arg Phe Glu Asn Pro Ser
                   370                 375                 380
Ala Ile Pro Gln His Ala Phe Lys Pro Phe Gly Asn Gly Gln Arg Ala
385                    390                 395                 400
Cys Ile Gly Gln Gln Phe Ala Leu His Glu Ala Thr Leu Val Leu Gly
                        405                 410                 415
Met Met Leu Lys His Phe Asp Phe Glu Asp His Thr Asn Tyr Glu Leu
                   420                 425                 430
Asp Ile Lys Glu Thr Leu Thr Leu Lys Pro Glu Gly Phe Val Val Lys
                   435                 440                 445
Ala Lys Ser Lys Lys Ile Pro Leu Gly Gly Ile Pro Ser Pro Ser Thr
                   450                 455                 460
Glu Gln Ser Ala Lys Lys Val Arg Lys Lys Ala Glu Asn Ala His Asn
465                    470                 475                 480
Thr Pro Leu Leu Val Leu Tyr Gly Ser Asn Met Gly Thr Ala Glu Gly
                        485                 490                 495
```

```
Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
            850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910
```

```
Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
1010                1015                1020

Val Ser Glu Ala Asp Ala Arg Leu Trp Leu Gln Gln Leu Glu Glu
1025                1030                1035

Lys Gly Arg Tyr Ala Lys Asp Val Trp Ala Gly
1040                1045

<210> SEQ ID NO 4
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
50                  55                  60

Glu Ser Arg Phe Asp Lys Asn Leu Ser Gln Ala Leu Lys Phe Val Arg
65                  70                  75                  80

Asp Phe Ala Gly Asp Gly Leu Gly Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Asp Asp Glu His Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
210                 215                 220
```

```
Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Leu Pro Ala Phe Ser Leu Tyr Ala
                325                 330                 335

Lys Glu Asp Thr Val Leu Gly Gly Tyr Pro Leu Glu Lys Gly Asp
                340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
        450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
        530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
        610                 615                 620

Val Ala Ala Tyr Phe Asn Leu Asp Ile Glu Asn Ser Glu Asp Asn Lys
625                 630                 635                 640
```

```
Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
        660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045
```

<210> SEQ ID NO 5
<211> LENGTH: 1399
<212> TYPE: DNA
<213> ORGANISM: Bacillus megaterium

<400> SEQUENCE: 5

| | |
|---|---|
| atgacaatta aagaaatgcc tcagccaaaa acgtttggag agcttaaaaa tttaccgtta | 60 |
| ttaaacacag ataaaccggt tcaagctttg atgaaaattg cggatgaatt aggagaaatc | 120 |
| tttaaattcg aggcgcctgg tcgtgtaacg cgctacttat caagtcagcg tctaattaaa | 180 |
| gaagcatgcg atgaatcacg ctttgataaa aacttaagtc aagcgcttaa atttgtacgt | 240 |
| gattttgcag gagacgggtt atttacaagc tggacgcatg aaaaaaattg gaaaaaagcg | 300 |
| cataatatct tacttccaag cttcagtcag caggcaatga aaggctatca tgcgatgatg | 360 |
| gtcgatatcg ccgtgcagct tgttcaaaag tgggagcgtc taaatgcaga tgagcatatt | 420 |
| gaagtaccgg aagacatgac acgtttaacg cttgatacaa ttggtctttg cggctttaac | 480 |
| tatcgcttta acagcttta ccgagatcag cctcatccat ttattacaag tatggtccgt | 540 |
| gcactggatg aagcaatgaa caagctgcag cgagcaaatc cagacgaccc agcttatgat | 600 |
| gaaaacaagc gccagtttca agaagatatc aaggtgatga cgacctagt agataaaatt | 660 |
| attgcagatc gcaaagcaag cggtgaacaa agcgatgatt tattaacgca tatgctaaac | 720 |
| ggaaaagatc cagaaacggg tgagccgctt gatgacgaga acattcgcta tcaaattatt | 780 |
| acattcttaa ttgcgggaca cgaaacaaca agtggtcttt tatcatttgc gctgtatttc | 840 |
| ttagtgaaaa atccacatgt attacaaaaa gcagcagaag aagcagcacg agttctagta | 900 |
| gatcctgttc caagctacaa acaagtcaaa cagcttaaat atgtcggcat ggtcttaaac | 960 |
| gaagcgctgc gcttatggcc aactgctcct gcgttttccc tatatgcaaa agaagatacg | 1020 |
| gtgcttggag gagaatatcc tttagaaaaa ggcgacgaac taatggttct gattcctcag | 1080 |
| cttcaccgtg ataaaacaat tggggagac gatgtggaag agttccgtcc agagcgtttt | 1140 |
| gaaaatccaa gtgcgattcc gcagcatgcg tttaaaccgt ttggaaacgg tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctcgata ttaaagaaac tttaacgtta | 1320 |
| aaacctgaag ctttgtggt aaaagcaaaa tcgaaaaaaa ttccgcttgg cggtattcct | 1380 |
| tcacctagca ctgaacagt | 1399 |

<210> SEQ ID NO 6
<211> LENGTH: 1399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

| | |
|---|---|
| atgacaatta aagaaatgcc tcagccaaaa acgtttggag agcttaaaaa tttaccgtta | 60 |
| ttaaacacag ataaaccggt tcaagctttg atgaaaattg cggatgaatt aggagaaatc | 120 |
| tttaaattcg aggcgcctgg tcgtgtaacg cgctacttat caagtcagcg tctaattaaa | 180 |
| gaagcatgcg atgaatcacg ctttgataaa aacttaagtc aagcgcttaa atttgtacgt | 240 |
| gattttgcag gagacgggtt aggtacaagc tggacgcatg aaaaaaattg gaaaaaagcg | 300 |
| cataatatct tacttccaag cttcagtcag caggcaatga aaggctatca tgcgatgatg | 360 |
| gtcgatatcg ccgtgcagct tgttcaaaag tgggagcgtc taaatgcaga tgagcatatt | 420 |

```
gaagtaccgg aagacatgac acgtttaacg cttgatacaa ttggtctttg cggctttaac      480
tatcgcttta acagcttta ccgagatcag cctcatccat ttattacaag tatggtccgt       540
gcactggatg aagcaatgaa caagctgcag cgagcaaatc cagacgaccc agcttatgat      600
gaaaacaagc gccagtttca agaagatatc aaggtgatga acgacctagt agataaaatt     660
attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtcttt tatcatttgc gctgtatttc     840
ttagtgaaaa atccacatgt attacaaaaa gcagcagaag aagcagcacg agttctagta    900
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa ggcgacgaac taatggttct gattcctcag   1080
cttcaccgtg ataaaacaat ttggggagac gatgtggaaa agttccgtcc agagcgtttt    1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagt                                                  1399

<210> SEQ ID NO 7
<211> LENGTH: 1399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgacaatta aagaaatgcc tcagccaaaa acgtttggag agcttaaaaa tttaccgtta     60
ttaaacacag ataaaccggt tcaagctttg atgaaaattg cggatgaatt aggagaaatc    120
tttaaattcg aggcgcctgg tcgtgtaacg cgctactat caagtcagcg tctaattaaa    180
gaagcatgcg atgaatcacg ctttgataaa aacttaagtc aagcgcttaa atttgtacgt    240
gattttgcag gagacgggtt aggtacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagcttta ccgagatcag cctcatccat ttattacaag tatggtccgt    540
gcactggatg aagcaatgaa caagctgcag cgagcaaatc cagacgaccc agcttatgat   600
gaaaacaagc gccagtttca agaagatatc aaggtgatga acgacctagt agataaaatt   660
attgcagatc gcaaagcaag cggtgaacaa agcgatgatt tattaacgca tatgctaaac   720
ggaaaagatc cagaaacggg tgagccgctt gatgacgaga acattcgcta tcaaattatt   780
acattcttaa ttgcgggaca cgaaacaaca agtggtcttt tatcatttgc gctgtatttc   840
ttagtgaaaa atccacatgt attacaaaaa gcagcagaag aagcagcacg agttctagta   900
gatcctgttc caagctacaa acaagtcaaa cagcttaaat atgtcggcat ggtcttaaac   960
gaagcgctgc gcttatggcc aacgctgcct gcgttttccc tatatgcaaa agaagatacg  1020
```

```
gtgcttggag gagaatatcc tttagaaaaa ggcgacgaac taatggttct gattcctcag   1080
cttcaccgtg ataaaacaat tgggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact tgaagatcga tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagt                                                1399

<210> SEQ ID NO 8
<211> LENGTH: 1399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgacaatta agaaatgcc tcagccaaaa acgtttggag agcttaaaaa tttaccgtta    60
ttaaacacag ataaaccggt tcaagctttg atgaaaattg cggatgaatt aggagaaatc   120
tttaaattcg aggcgcctgg tcgtgtaacg cgctacttat caagtcagcg tctaattaaa   180
gaagcatgcg atgaatcacg ctttgataaa aacttaagtc aagcgcttaa atttgtacgt   240
gattttgcag gagacgggtt aggtacaagc tggacgcatg aaaaaaattg gaaaaaagcg   300
cataatatct tacttccaag cttcagtcag caggcaatga aaggctatca tgcgatgatg   360
gtcgatatcg ccgtgcagct tgttcaaaag tgggagcgtc taaatgcaga tgagcatatt   420
gaagtaccgg aagacatgac acgtttaacg cttgatacaa ttggtctttg cggctttaac   480
tatcgcttta acagctttta ccgagatcag cctcatccat ttattacaag tatggtccgt   540
gcagatgatg aacatatgaa caagctgcag cgagcaaatc cagacgaccc agcttatgat   600
gaaaacaagc gccagtttca agaagatatc aaggtgatga acgacctagt agataaaatt   660
attgcagatc gcaaagcaag cggtgaacaa agcgatgatt tattaacgca tatgctaaac   720
ggaaaagatc cagaaacggg tgagccgctt gatgacgaga acattcgcta tcaaattatt   780
acattcttaa ttgcgggaca cgaaacaaca agtggtcttt tatcatttgc gctgtatttc   840
ttagtgaaaa atccacatgt attacaaaaa gcagcagaag aagcagcacg agttctagta   900
gatcctgttc aagctacaa acaagtcaaa cagcttaaat atgtcggcat ggtcttaaac   960
gaagcgctgc gcttatggcc aacgctgcct gcgttttccc tatatgcaaa agaagatacg   1020
gtgcttggag gagaatatcc tttagaaaaa ggcgacgaac taatggttct gattcctcag   1080
cttcaccgtg ataaaacaat tgggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact tgaagatcga tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagt                                                1399

<210> SEQ ID NO 9
<211> LENGTH: 50
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
aactttaaga aggagatata catatgacaa ttaaagaaat gcctcagcca                  50

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagtgctagg tgaaggaata ccgccaagcg gaa                                    33

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggctgaggc atttctttaa ttgtcatatg tatatctcct tcttaaagtt                  50

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttccgcttgg cggtattcct tcacctagca ctg                                    33

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taatacgact cactataggg                                                   20

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: a, c, t, g, unknown or other

<400> SEQUENCE: 14
tgcaggagac gggttannka caagctggac gcatg                                  35

<210> SEQ ID NO 15
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(19)
<223> OTHER INFORMATION: a, c, t, g, unknown or other

<400> SEQUENCE: 15
catgcgtcca gcttgtmnnt aacccgtctc ctgca                           35

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 16
gcttatggcc andtndtcct gcgttttcc                                  29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 17
ggaaaacgca ggahnahntg gccataagc                                  29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcttatggcc avhgvhgcct gcgttttcc                                  29

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 19
ggaaaacgca ggcdbcdbtg gccataagc                                              29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other

<400> SEQUENCE: 20
gcttatggcc andtvhgcct gcgttttcc                                              29

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: a, c, t, g, unknown or other

<400> SEQUENCE: 21
ggaaaacgca ggcdbahntg gccataagc                                              29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: a, c, t, g, unknown or other

<400> SEQUENCE: 22
gcttatggcc avhgndtcct gcgttttcc                                              29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: a, c, t, g, unknown or other

<400> SEQUENCE: 23
ggaaaacgca ggahncdbtg gccataagc                                              29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
```

```
    primer
<220> FEATURE:
<221> NAME/KEY: modified_base
<222> LOCATION: (12)..(12)
<223> OTHER INFORMATION: a, c, t, g, unknown or other

<400> SEQUENCE: 24
gcttatggcc andttggcct gcgttttcc                                    29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: a, c, t, g, unknown or other

<400> SEQUENCE: 25
ggaaaacgca ggccaahntg gccataagc                                    29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: a, c, t, g, unknown or other

<400> SEQUENCE: 26
gcttatggcc atggndtcct gcgttttcc                                    29

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: a, c, t, g, unknown or other

<400> SEQUENCE: 27
ggaaaacgca ggahnccatg gccataagc                                    29

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcttatggcc avhgtggcct gcgttttcc                                    29

<210> SEQ ID NO 29
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 29
ggaaaacgca ggccacdbtg gccataagc                                        29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcttatggcc atggvhgcct gcgttttcc                                        29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggaaaacgca ggcdbccatg gccataagc                                        29

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcttatggcc atggtggcct gcgttttcc                                        29

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggaaaacgca ggccaccatg gccataagc                                        29

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 34
```
ggtccgtgca ndtgatgaan dtatgaacaa gc                                    32

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 35
gcttgttcat ahnttcatca hntgcacgga cc                                    32

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 36
ggtccgtgca vhggatgaav hgatgaacaa gc                                    32

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 37
gcttgttcat cdbttcatcc dbtgcacgga cc                                    32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (11)..(11)
<223> OTHER INFORMATION: a, c, t, g, unknown or other

<400> SEQUENCE: 38
ggtccgtgca ndtgatgaav hgatgaacaa gc                                    32

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (22)..(22)
<223> OTHER INFORMATION: a, c, t, g, unknown or other

<400> SEQUENCE: 39
gcttgttcat cdbttcatca hntgcacgga cc                                32

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (20)..(20)
<223> OTHER INFORMATION: a, c, t, g, unknown or other

<400> SEQUENCE: 40
ggtccgtgca vhggatgaan dtatgaacaa gc                                32

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (13)..(13)
<223> OTHER INFORMATION: a, c, t, g, unknown or other

<400> SEQUENCE: 41
gcttgttcat ahnttcatcc dbtgcacgga cc                                32

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (11)..(11)
<223> OTHER INFORMATION: a, c, t, g, unknown or other

<400> SEQUENCE: 42
ggtccgtgca ndtgatgaat ggatgaacaa gc                                32

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (22)..(22)
<223> OTHER INFORMATION: a, c, t, g, unknown or other

<400> SEQUENCE: 43
gcttgttcat ccattcatca hntgcacgga cc                                32

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic

```
      primer
<220> FEATURE:
<221> NAME/KEY: modified_base
<222> LOCATION: (20)..(20)
<223> OTHER INFORMATION: a, c, t, g, unknown or other

<400> SEQUENCE: 44
ggtccgtgca tgggatgaan dtatgaacaa gc                                    32

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(13)
<223> OTHER INFORMATION: a, c, t, g, unknown or other

<400> SEQUENCE: 45
gcttgttcat ahnttcatcc catgcacgga cc                                    32

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggtccgtgca vhggatgaat ggatgaacaa gc                                    32

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcttgttcat ccattcatcc dbtgcacgga cc                                    32

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggtccgtgca tgggatgaav hgatgaacaa gc                                    32

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcttgttcat cdbttcatcc catgcacgga cc                                    32
```

```
<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggtccgtgca tgggatgaat ggatgaacaa gc                                    32

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gcttgttcat ccattcatcc catgcacgga cc                                    32
```

METHOD OF PREPARING SILANOLS WITH SELECTIVE CYTOCHROME P450 VARIANTS AND RELATED COMPOUNDS AND COMPOSITIONS

CROSS-REFERENCE TO RELATED APPLICATIONS

This application is the U.S. National Stage of International Application No. PCT/US2021/018749 filed on 19 Feb. 2021, which claims priority to and all advantages of U.S. Provisional Patent Application No. 62/979,960 filed on 21 Feb. 2020, the content of which is incorporated herein by reference.

SEQUENCE LISTING

This application includes a Sequence Listing, a copy of which, created on 19 Feb. 2021 and having the name "83543-WO-PCT_SL.txt" and a size of 56,647 bytes, has been submitted electronically in ASCII format and is hereby incorporated by reference in its entirety.

FIELD OF THE INVENTION

The present disclosure relates generally to a catalyst and methods for preparing silanol-functional organosilicon compounds and, more specifically, to a cytochrome protein variant catalyst that selectively oxidizes silicon-bonded hydrogen to silanol in organosilicon compounds, methods of using the same, and silanol-functional organosilicon compounds prepared with the catalyst.

DESCRIPTION OF THE RELATED ART

Silicones are polymeric materials used in numerous commercial applications, primarily due to significant advantages they possess over many carbon-based analogues. More particularly referred to as polymerized siloxanes or polysiloxanes, silicones include an inorganic silicon-oxygen backbone chain ( . . . —Si—O—Si—O—Si—O— . . . ) having organic side groups attached to the silicon atoms. Organic side groups may be used to link two or more of these backbones together. By varying the —Si—O— chain lengths, side groups, and cross-linking, silicones can be synthesized with a wide variety of properties and compositions, with silicone networks varying in consistency from liquid to gel to rubber to hard plastic. Silicone and siloxane-based materials are utilized in myriad end use applications and environments, including as components in a wide variety of industrial, home care, and personal care formulations.

Silanols represent an important and valuable class of silicon compounds and are frequently utilized as precursors for preparing many silicone and siloxane-based materials, as well as other products in the silicon industry. Silanols are also used as synthetic intermediates in organic synthesis, as monomeric building blocks for silicone-organic hybrid materials, and as catalysts for certain reactions. Silanols are also utilized directly as components of many commercial formulations, e.g. as reactive or functional components.

Unfortunately, conventional methods of preparing silanols suffer from myriad drawbacks and disadvantageous. In particular, many such methods utilize highly reactive precursors such as chlorosilanes, or strong oxidants in combination with hydrosilanes, which often lead to competing side reactions, such as disiloxane formation, and generate substantial amounts of waste products. Direct catalytic oxidation methods have been developed to overcome such disadvantageous, but typically rely on precious metals such as gold, silver, rhodium, ruthenium, or palladium. Moreover, the methods also suffer from disiloxane contamination, as the silanol products generated are free to react with activated hydrosilane intermediates prepared with the catalysts.

BRIEF SUMMARY

A method of preparing a silanol-functional organosilicon compound is provided. The method comprises combining a cytochrome P450 variant and an organosilicon compound to prepare a reaction mixture. The cytochrome P450 variant has activity oxidizing a silyl hydride group to a silanol group in the presence of oxygen, and the organosilicon compound has at least one silicon-bonded hydrogen atom. The method also comprises exposing the reaction mixture to oxygen to oxidize the organosilicon compound, thereby preparing the silanol-functional organosilicon compound.

Cytochrome P450 variants are also provided. One of the cytochrome P450 variants comprises an amino acid sequence of SEQ ID NO:2 or a conservatively modified variant thereof. Another of the cytochrome P450 variants comprises an amino acid sequence of SEQ ID NO:3 or a conservatively modified variant thereof. Another of the cytochrome P450 variants comprises an amino acid sequence of SEQ ID NO:4 or a conservatively modified variant thereof.

Nucleic acids encoding the cytochrome P450 variants are also provided, along with compositions, expression vectors, and host cells comprising the same. One of the nucleic acids comprises a nucleotide sequence of SEQ ID NO:5 or a conservatively modified variant thereof. Another of the nucleic acids comprises a nucleotide sequence of SEQ ID NO:6 or a conservatively modified variant thereof. Another of the nucleic acids comprises a nucleotide sequence of SEQ ID NO:7 or a conservatively modified variant thereof.

BRIEF DESCRIPTION OF THE DRAWINGS

FIGS. 1-10 include calibration curves prepared from gas chromatography (GC) data obtained from authenticated silanol-functional organosilicon compounds (standards) utilized in the Examples.

DETAILED DESCRIPTION OF THE INVENTION

Figure 3:
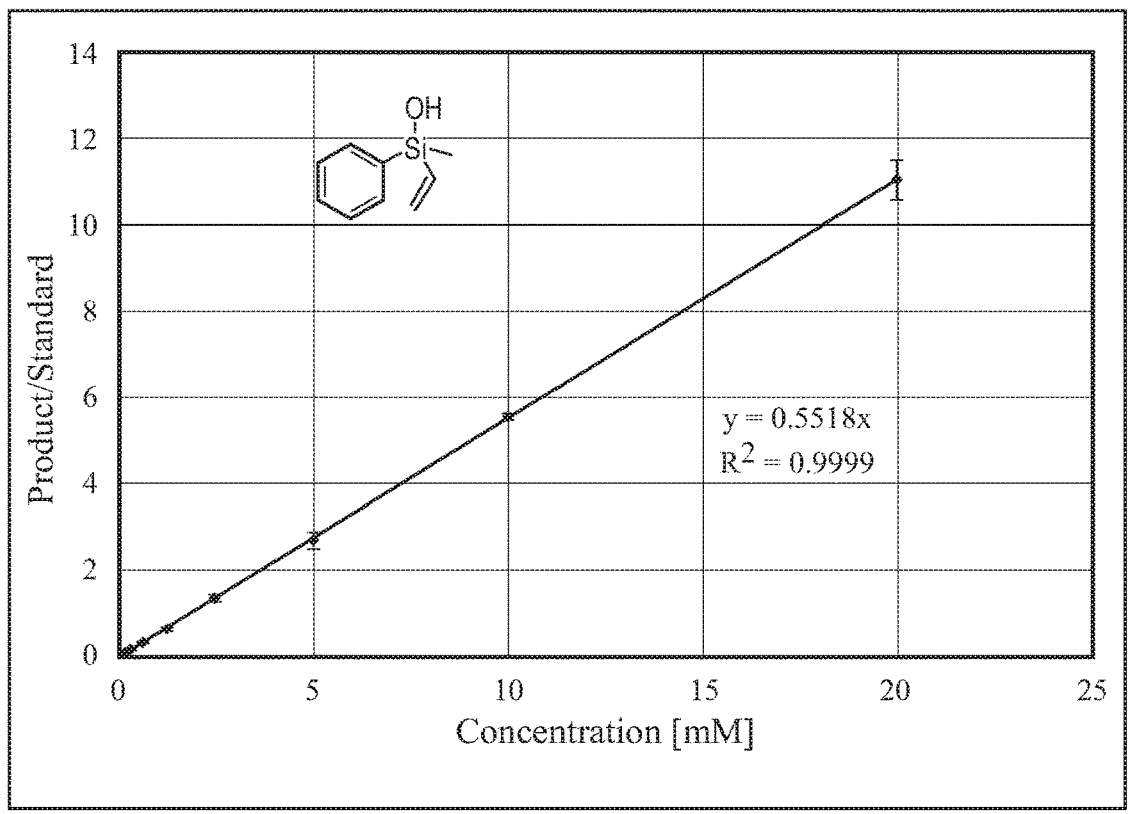

A method of preparing a silanol-functional organosilicon compound is provided. In general, the method comprises combining a cytochrome P450 variant and an organosilicon compound in the presence of oxygen to prepare the silanol-functional organosilicon compound. More specifically, the cytochrome P450 variant is capable of facilitating the oxidation of a hydridosilane to a silanol, and the organosilicon compound comprises at least one silyl hydride group (i.e., a silicon-bonded hydrogen atom) capable of being oxidized to give the silanol-functional organosilicon compound.

Notably, although enzymatic manipulations of functional groups proximal to silicon in various organosilicon compounds are known, the direct biocatalytic functionalization of a silicon center was unknown prior to the recent reporting of a cytochrome c-catalyzed carbene insertion into Si—H bonds, both in vitro and in vivo. It is believed that the present invention, as illustrated by the examples and described herein, represents the first biocatalytic transformation of a silyl hydride group (i.e., Si—H) to a silanol group (i.e., Si—OH). Accordingly, it will be appreciated that certain aspects of the invention described herein in relation to the method may be practiced individually or in various combinations, i.e., without limitation as to any particular end-use, composition, formulation, etc. Such aspects include novel cytochrome P450 variants, materials and compositions relating thereto, as well as various methods of preparing the same.

As will be understood by those of skill in the art, the method and materials described herein relate generally to biocatalysis (i.e., the use of a biological system and/or material to facilitate a chemical reaction), and more specifically to protein-based biocatalysts. For purposes of clarity, certain terms utilized herein are set forth and described below.

The terms "protein," "peptide," and "polypeptide" are used interchangeably herein to refer to a polymer of amino acid residues (i.e., a molecule having 2 or more amino acids that are joined together by a peptide bond) or an assembly of multiple polymers of amino acid residues. In some instances, more specific terms may be utilized, such as with reference to one or more particular oligopeptides (i.e., peptides comprising 20 or fewer, optionally 10 or fewer amino acids, e.g. di-, tri-, tetra-, and pentapeptides, etc.) polypeptides (i.e., peptides comprising greater than 10, optionally greater than 20 amino acids), proteins (i.e., organic compounds comprising amino acids linked via peptide bonds in a linear chain and folded into a globular form), enzymes (i.e., functional proteins, optionally comprising cofactors, multiple proteins, etc.), and the like, which may be modified (e.g. naturally and/or synthetically via glycosylation, acetylation, phosphorylation, etc.), branched, etc. Such terms apply to amino acid polymers in which one or more amino acid residues are an artificial chemical mimic of a corresponding naturally occurring amino acid, as well as to naturally occurring (i.e., native) amino acid polymers and non-naturally occurring (i.e., synthetic, engineered, etc.) amino acid polymers. The identity and order of particular amino acid residues in a protein is generally referred to as an "amino acid sequence".

The term "amino acid" includes both naturally occurring and non-naturally occurring amino acids, as stereoisomers thereof. In this context, a stereoisomer of an amino acids generally refers to a mirror isomer of opposing stereochemistry at the alpha carbon atom, such as an L-stereroisomer (i.e., a left-handed isomer) and a D-stereroisomer (i.e., a right-handed isomer) of the same alpha-amino acid. For example, a stereoisomer of a naturally occurring amino acid (which are L-stereroisomers) refers to the mirror image isomer of the naturally occurring amino acid, i.e., the D-stereroisomer. As will be appreciated from certain examples below, amino acids may be referred to herein by either their commonly known three letter symbols or by the one-letter symbols recommended by the Biochemical Nomenclature Commission of the International Union of Pure and Applied Chemistry and the International Union of Biochemistry (IUPAC-IUB). For example, an L-amino acid may be represented herein by its commonly known three letter symbol (e.g. Arg for L-arginine) or by an upper-case one-letter amino acid symbol (e.g. R for L-arginine). A D-amino acid may be represented herein by its commonly known three letter symbol (e.g. D-Arg for D-arginine) or by a lower-case one-letter amino acid symbol (e.g. r for D-arginine).

Naturally occurring amino acids are those encoded by the genetic code, as well as natural derivative/modifications thereof (e.g. hydroxyproline, γ-carboxyglutamate, O-phosphoserine, etc.). Examples of naturally occurring α-amino acids include, among others, alanine (Ala; A), cysteine (Cys; C), aspartic acid (Asp; D), glutamic acid (Glu; E), phenylalanine (Phe; F), glycine (Gly; G), histidine (His; H), isoleucine (Ile; I), arginine (Arg; R), lysine (Lys; K), leucine (Leu; L), methionine (Met; M), asparagine (Asn; N), proline (Pro; P), glutamine (Gln; Q), serine (Ser; S), threonine (Thr; T), valine (Val; V), tryptophan (Trp; W), and tyrosine (Tyr; Y), and combinations thereof. Likewise, examples of stereoisomers of naturally occurring α-amino acids include D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), and D-tyrosine (D-Tyr). Examples of non-naturally occurring (i.e., unnatural) amino acids include various amino acid analogs and mimetics, as well as synthetic amino acids, in either L- or D-configurations (e.g. N-substituted glycines, and N-methyl amino acids, etc.). Examples of amino acid analogs include unnatural amino acids having the same basic chemical structure as naturally occurring amino acids (i.e., an α-carbon bonded to a hydrogen, a carboxyl group, and an amino group) but a modified side-chain groups, or modified peptide backbones, (e.g. homoserine, norleucine, methionine sulfoxide, methionine methyl sulfonium, etc.). "Amino acid mimetics" refer to chemical compounds that have a structure that is different from the general chemical structure of an amino acid, but that functions in a manner similar to a naturally occurring amino acid.

With respect to the amino acid sequences of proteins, one of skill in the art will recognize that individual substitutions, additions, or deletions that alter, add, and/or delete a single amino acid, or a small percentage of amino acids in the sequence, may be referred to as a "conservative modification" of the amino acid sequence where the alteration results in the substitution of an amino acid with a chemically similar amino acid, particularly where the function of the protein is largely or wholly unchanged. Likewise, a protein having a conservatively modified sequence may be referred to as a "conservatively modified variant" of a wild type or otherwise unmodified protein sequence. Unless otherwise indicated, a particular amino acid sequence is to be understood to implicitly encompass conservatively modified variants in addition to the sequence explicitly indicated.

As will be understood by those of skill in the art, chemically similar amino acids are not limited, and conservative substitution tables setting forth functionally similar amino acids are well known in the art. For example, substitutions may be made wherein one aliphatic amino acid (e.g. G, A, I, L, V, etc.) is substituted with another aliphatic amino acid, where an aliphatic amino acid having a polar-uncharged group (e.g. C, S, T, M, N, Q, etc.) is substituted with another such aliphatic amino acid, where a basic amino acid (e.g. K, R, H, etc.) is substituted for a different basic amino acid, etc. In some instances, a conservative substitution comprises substituting an amino acid with an acidic side chain (e.g. E or D) with an uncharged counterpart (e.g. Q or N, respectively), or vice versa. Each of the following eight groups contains other exemplary amino acids that may be conservative substitutions for one another:
1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

The terms "oligonucleotide," "nucleic acid," and "polynucleotide" are used interchangeably herein to refer to polymers comprising nucleotides, i.e., deoxyribonucleic acids (DNA) and/or ribonucleic acids (RNA) in either single-, double-, or multi-stranded forms (i.e., single-, double-, and multi-stranded DNA and/or RNA, including genomic DNA, cDNA, DNA-RNA hybrids), as well as polymers comprising purine, pyrimidine, or other nucleotide bases, which may be natural or non-naturally occurring bases (e.g. such as chemically modified, biochemically modified, synthetic, and/or derivatized nucleotide bases). As will be understood by those of skill in the art, a polynucleotide may be described in relation to a peptide encoded thereby, such that the term "nucleotide sequence encoding a peptide" or the like may be used to refer to a segment of DNA involved in producing a peptide chain. Such a segment can include regions preceding and/or following a given coding region (i.e., a leader and/or trailer sequence) involved in the transcription/translation of a gene product or regulation thereof, as well as intervening sequences (introns) between individual coding segments (exons). Accordingly, the term "nucleic acid" and the like may be used interchangeably with gene, cDNA, and mRNA encoded by a gene. Unless specifically limited, the terms also encompass nucleic acids containing known analogs of natural/reference nucleotides that have similar binding properties as the reference nucleic acid, which may be metabolized in a manner similar to naturally occurring nucleotides.

The identity and order of particular nucleotide bases in a polynucleotide is generally referred to as a "nucleic acid sequence". As with the amino acid sequences described above, unless otherwise indicated, a particular nucleic acid sequence is to be understood to implicitly encompass conservatively modified variants of the sequence in addition to the nucleic acid sequence explicitly indicated. Conservatively modified variants of a polynucleotide generally comprise degenerate codon substitutions, or complementary or orthologous sequences compared to a given wild type or otherwise unmodified nucleic acid sequence. As known in the art, degenerate codon substitutions may be achieved by generating sequences in which the third position of a selected codon is substituted with mixed-base and/or deoxyinosine residues.

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species.

The terms "homologous" or "homolog" are used herein with reference to similar sequences of polynucleotides and/or nucleic acids. For example, a first protein has "homology" or is "homologous" to a second protein if the amino acid sequence encoded by a gene has a similar amino acid sequence to that of the second gene. Alternatively, a first protein has homology to a second protein if the two proteins have "similar" amino acid sequences. Thus, the term "homologous proteins" is intended to mean that the two proteins have similar amino acid sequences. Similarly, the term "functional homolog" refers to each member of a subgroup of homologs or homologous sequences that share a common functionality, i.e., a primary function for which a protein, gene, sequence, and the like is named and/or utilized. For example, the function of a promoter is to facilitate transcription of a gene or nucleotide sequence and the function of an enzyme is to catalyze a particular chemical reaction or family of chemical reactions. As such, term "functionality" encompasses all reaction rates and all enzymatic efficiencies exhibited by a given protein. In particular embodiments, the homology between two proteins is indicative of its shared ancestry, related by evolution. It will be appreciated that homologs most often have functional, structural, or genomic similarities. For example, in certain embodiments, homologous sequences share at least 70% sequence identity, such as at least 80, alternatively at least 90, alternatively at least 95, alternatively at least 99% sequence identity. Techniques are known by which homologs of an enzyme or gene can readily be cloned using genetic probes and PCR. Identity of cloned sequences as homolog can be confirmed using functional assays and/or by genomic mapping of the genes.

As introduced above, the method utilizes a cytochrome P450 variant capable of oxidizing a hydridosilane to a silanol. More specifically, the cytochrome P450 variant facilitates the selective oxidation of the silyl hydride group (i.e., Si—H) of the organosilicon compound to a silanol group (i.e., Si—OH), as described in additional detail below, and is otherwise not particularly limited.

As will be understood by those of skill in the art, the term "cytochrome P450" as utilized herein refers to an enzyme classified or otherwise characterized as a member of the cytochrome P450 enzyme family, which is known to comprise a large superfamily of heme-thiolate proteins that typically possess an active site containing an Fe(III)-protoporphyrin IX cofactor (i.e., a heme-iron center) proximally tethered by a highly conserved cysteine thiolate residue. In the resting state, the remaining axial iron coordination site is occupied by a water molecule. However, the heme-iron center is capable of binding molecular oxygen at this axial iron coordination site, giving rise to the native catalytic reactivity.

Cytochrome P450 enzymes are involved in the metabolism of a wide variety of both exogenous and endogenous compounds, and often function as a terminal oxidase in multicomponent electron transfer chains, such as P450-containing monooxygenase systems. Cytochrome P450 enzymes are known to catalyze myriad carbon-centered oxidative transformations, including carbon oxygenations and hydroxylations, epoxidations, oxidative ring couplings, and desaturations. A general chemical mechanism used to rationalize most of the oxidative activity of native cytochrome P450 enzymes involves a perfenyl ($FeO^{3+}$) intermediate and odd-electron chemistry. In particular, the heme-iron center activates molecular oxygen in the presence of an electron source (e.g. nicotinamide adenine dinucleotide (NADH) or nicotinamide adenine dinucleotide phosphate (NADPH), such as from an adjacent fused reductase domain, an accessory cytochrome P450 reductase enzyme, etc.) to generate a molecule of water and an iron(IV)-oxo porphyrin radical cation intermediate conventionally known as "P450 Compound 1". More specifically, after induction of a first electron transfer (e.g. via substrate binding), molecular oxygen binds to the ferrous heme center to give a dioxygen adduct (e.g. Fe—$O_2$). The Fe—$O_2$ adduct is reduced via a second electron transfer to give a peroxo intermediate, which undergoes rapid dipronation (i.e., two protonations) to release water and give the iron(IV) oxo intermediate (i.e., P450 Compound 1). The highly reactive iron(IV) oxo intermediate then reacts with a substrate at a C—H or C=C bond (e.g. via abstraction of a hydrogen atom or electron, followed by oxygen rebound, rearrangement, etc.) to affect an oxidative transformation (e.g. a hydroxylation, epoxidation etc.).

As understood in the art, both genes encoding cytochrome P450 enzymes, as well as the enzymes themselves, may be designated according to a common naming convention utilizing the root symbol "CYP" indicating the superfamily, followed by: 1) a number indicating the gene family; 2) a capital letter indicating the subfamily; and 3) a numeral indicating an individual gene. For example, the gene designated "CYP102A1" encodes the enzyme CYP102A1 (also known as cytochrome P450 BM3), which is isolated from soil bacterium *Bacillus megaterium* and facilitates the NADPH-dependent hydroxylation of long-chain fatty acids at the ω-1 through ω-3 positions. Typically, members of a CYP family share at least 40% amino acid identity, while members of subfamilies share at least 55% amino acid identity.

As introduced above, the method utilizes a cytochrome P450 variant. The term "variant", as used herein in the context of a "protein variant" or "enzyme variant" (e.g. the cytochrome P450 variant) describes a protein or enzyme comprising at least one amino acid mutation (e.g. a substitution) with respect to a wild-type version of the protein/enzyme, including chimeric enzymes comprising recombined sequences or blocks of amino acids from two, three, or more different proteins. However, it is to be understood that certain protein variants need not be prepared via purposeful mutagenesis, but may instead be a natural enzyme that exhibits a desired activity and/or substrate specificity (i.e., selective silane oxidation) that is not natively exhibited by one or more homologous wild-type enzymes. As such, it is to be understood that the term "cytochrome P450 variant" as used herein encompasses the particular cytochrome P450 variants designated by given sequences and provided according to some aspects of this disclosure, as well as certain wild-type cytochrome P450 variants suitable for use in the method, which are described in further detail below. It is also to be appreciated that the cytochrome P450 variant may comprise, or be, a fragment of a cytochrome P450 enzyme that exhibits the activity and/or substrate specificity required to prepare the silanol-functional organosilicon compound.

The cytochrome P450 variant utilized in the method is capable of oxidizing a hydridosilane to a silanol and is otherwise not particularly limited. As such, examples of cytochrome P450 variants suitable for use in the method include those which facilitate the selective oxidation of the silyl hydride group (i.e., Si—H) of the organosilicon compound to a silanol group (i.e., Si—OH), as described in additional detail below.

In some embodiments, the cytochrome P450 variant is a P450 BM3 (CYP102A1) protein or a variant thereof. As understood by those of skill in the art, cytochrome P450 BM3 is a self-sufficient 118-kDa monooxygenase having a flavin adenine dinucleotide (FAD)- and flavin mononucleotide (FMN)-containing NADPH-dependent reductase domain fused to the C-terminus of a heme domain. Nucleotide and amino acid sequences for cytochrome P450 BM3 may be obtained from public databases, such as the GenBank database maintained by the U.S. National Center for Biotechnology Information (NCBI) under the International Nucleotide Sequence Database Collaboration (INSDC), or the UniProt database maintained by the UniProt Consortium under accession number P14779.

In some embodiments, the cytochrome P450 variant comprises an amino acid sequence having at least 70% identity to the amino acid sequence set forth in SEQ ID NO:1, such as at least 75, alternatively at least 80, alternatively at least 85, alternatively at least 90, alternatively at least 95% identity to the amino acid sequence set forth in SEQ ID NO:1. In particular embodiments, the cytochrome P450 variant comprises an amino acid sequence having greater than 95%, alternatively greater than 96%, alternatively greater than 97%, alternatively greater than 98%, alternatively greater than 99%, alternatively 100% identical to the amino acid sequence set forth in SEQ ID NO:1.

In certain embodiments, the cytochrome P450 variant is an engineered variant of cytochrome P450 BM3. For example, in some such embodiments, the cytochrome P450 variant is a mutant of cytochrome P450 BM3 comprising a structural mutation, such as an amino acid substitution, deletion, duplication, and/or insertion. In particular embodiments, the structural mutation is an amino acid substitution.

In some embodiments, the cytochrome P450 variant is a mutant of cytochrome P450 BM3 comprising, alternatively consisting essentially of, alternatively consisting of, the same number of amino acid residues as the wild-type protein (e.g. cytochrome P450 BM3). In these or other embodiments, the cytochrome P450 variant comprises an amino acid sequence having from 100 to 465 of the amino acids of SEQ ID NO:1, such as from 150 to 465, alternatively from 200 to 465, alternatively from 250 to 465, alternatively from 300 to 465, alternatively from 350 to 465, alternatively from 400 to 465, alternatively from 425 to 465, alternatively from 450 to 465, alternatively from 450 to 465 of the amino acids of SEQ ID NO:1. In such embodiments, these conserved amino acids may be contiguous, or separated by any number of amino acids in the sequence of the cytochrome P450 variant.

In some embodiments, the cytochrome P450 variant comprises a mutation in an amino acid of the heme-binding pocket, such as at one or more residues near the iron cofactor, the proximal heme-binding pocket, the distal heme-binding pocket, etc. For example, in particular embodiments, the cytochrome P450 variant comprises a mutation at one or more conserved residues of cytochrome P450 BM3 proximal the heme center, such as a residue residing within 15, alternatively within 12, alternatively within 10, alternatively within 8, alternatively within 7 Å of the heme center (e.g. as determined from crystallographic data).

In specific embodiments, the cytochrome P450 variant comprises an F88 mutation relative to the amino acid sequence of SEQ ID NO:1. For example, in some such embodiments, the F88 mutation is an F88G mutation. In some such embodiments, the cytochrome P450 variant comprises an amino acid sequence that having at least 70% identity to the amino acid sequence set forth in SEQ ID NO:2, such as at least 75, alternatively at least 80, alternatively at least 85, alternatively at least 90, alternatively at least 95% identity to the amino acid sequence set forth in SEQ ID NO:2. In particular such embodiments, the cytochrome P450 variant comprises an amino acid sequence having greater than 95%, alternatively greater than 96%, alternatively greater than 97%, alternatively greater than 98%, alternatively greater than 99%, alternatively 100% identical to the amino acid sequence set forth in SEQ ID NO:2.

Other mutations may also be utilized. For example, in certain embodiments, the cytochrome P450 variant comprises an A329 mutation relative to the amino acid sequence of SEQ ID NO:1. In some such embodiments, the A329 mutation is an A329L mutation. In these or other embodiments, the cytochrome P450 variant comprises an L182 mutation relative to the amino acid sequence of SEQ ID NO:1. In some such embodiments, the L182 mutation is an L182D mutation. In these or other embodiments, the cytochrome P450 variant comprises an A185 mutation relative to the amino acid sequence of SEQ ID NO:1. In some such embodiments, the A185 mutation is an A185H mutation.

It is to be appreciated that the cytochrome P450 variant may comprise a combination of different mutations, such as any two or more of the amino acid substitutes described above. For example, in some embodiments, the cytochrome P450 variant comprises both F88 and A329 mutations relative to the amino acid sequence of SEQ ID NO:1. In particular embodiments, the cytochrome P450 variant comprises both F88G and A329L mutations relative to the amino acid sequence of SEQ ID NO:1. In some such embodiments, the cytochrome P450 variant comprises an amino acid sequence that having at least 70% identity to the amino acid sequence set forth in SEQ ID NO:3, such as at least 75, alternatively at least 80, alternatively at least 85, alternatively at least 90, alternatively at least 95% identity to the amino acid sequence set forth in SEQ ID NO:3. In particular such embodiments, the cytochrome P450 variant comprises an amino acid sequence having greater than 95%, alternatively greater than 96%, alternatively greater than 97%, alternatively greater than 98%, alternatively greater than 99%, alternatively 100% identical to the amino acid sequence set forth in SEQ ID NO:3.

In some embodiments, the cytochrome P450 variant comprises F88, A329, L182, and A185 mutations relative to the amino acid sequence of SEQ ID NO:1. In particular embodiments, the cytochrome P450 variant comprises F88G, A329L, L182D, and A185H mutations relative to the amino acid sequence of SEQ ID NO:1. In some such embodiments, the cytochrome P450 variant comprises an amino acid sequence that having at least 70% identity to the amino acid sequence set forth in SEQ ID NO:4, such as at least 75, alternatively at least 80, alternatively at least 85, alternatively at least 90, alternatively at least 95% identity to the amino acid sequence set forth in SEQ ID NO:4. In particular such embodiments, the cytochrome P450 variant comprises an amino acid sequence having greater than 95%, alternatively greater than 96%, alternatively greater than 97%, alternatively greater than 98%, alternatively greater than 99%, alternatively 100% identical to the amino acid sequence set forth in SEQ ID NO:4.

It will be understood by those of skill in the art that, with respect to a particular amino acid sequence of a cytochrome P450, the conventional numbering utilized to identify/signify a particular amino acid residue disregards the initial methionine residue (e.g. encoded by the start codon), such that the first residue following the initial methionine is the first numbered residue in the sequence. As such, with respect to the mutations above, it will likewise be appreciated that such residues may be assigned or otherwise designated based on the conventional numbering of the cytochrome P450 variant rather than a sequential numbering, such that the F88, A329, L182, and A185 mutations may be instead referred to as F87, A328, L181, and A184 mutations.

It is also to be appreciated that the cytochrome P450 variant may comprise mutations (e.g. substitutions, etc.) at one or more residues other than those described above, as alternative or additional mutations. In general, residues suitable for mutations to prepare cytochrome P450 variants suitable for the method will be determined by those of skill in the art (e.g. based on the particular wild-type enzyme being modified, potential hydridosilanes to be oxidized, conditions to be utilized, etc.), and generally include conserved residues capable of influencing the reaction characteristics of the enzyme (e.g. reactivity of the heme-iron center, selectivity, solvent tolerance, and/or cofactor dependence of the enzyme, etc.). For example, in some embodiments, the cytochrome P450 variant comprises a mutation allowing for the incorporation of non-native cofactors, such as alternative heme cofactors (e.g. protoporphyrin IX or other porphyrin molecules containing metals other than iron, such as cobalt, rhodium, copper, ruthenium, iridium, and manganese, etc.) and/or alternative reducing cofactors (e.g. NADH vs. NADPH, etc.). Such residues can be identified using any technique known in the art, including crystallographic studies, phylogenetic studies, mutagenesis studies, etc., for which procedures are well known.

Mutations may be introduced into the sequence of the cytochrome P450 variant using standard gene synthesis and/or cloning techniques such as directed mutagenesis techniques, random mutagenesis techniques, etc., as well as various combinations thereof. Examples of such techniques include error-prone polymerase chain reaction (PCR), cassette mutagenesis, oligonucleotide-directed mutagenesis, parallel PCR, random mutagenesis with random fragmentation and reassembly via mutual priming, chemical mutagenesis, irradiation, DNA shuffling, and the like, as well as modifications and/or combinations thereof. In certain embodiments, the cytochrome P450 variant is prepared using site-directed mutagenesis (i.e., introducing specific nucleotide changes at pre-determined locations), such as via PCR site-directed mutagenesis, cassette mutagenesis, whole plasmid mutagenesis, Kunkel's method, or the like, or a combination thereof. Certain techniques will be selected based on the particular cytochrome P450 variant being prepared. For example, in certain embodiments, directed mutagenesis techniques may be used to selectively substitute one or more of the conserved residues described above. In these or other embodiments, one or more of the mutagenesis techniques above may also be employed under low-fidelity polymerization conditions introduce random point mutations over a long sequence, mutagenize a mixture of fragments of unknown sequences, etc. As such, it will be appreciated that the above techniques are not limiting, and other techniques may also be utilized.

In certain embodiments, the cytochrome P450 variant is engineered using directed evolution. In such embodiments, directed evolution is utilized to optimize the cytochrome P450 variant, i.e., by generating a saturation mutagenesis library (e.g. via single-site-saturation mutagenesis, double-site-saturation mutagenesis, etc.) and selecting cytochrome P450 variants exhibiting improved activity upon screening, as described in additional detail below.

As will be understood by those of skill in the art, saturation mutagenesis is a technique utilized to introduce random mutations at predetermined locations in an encoded protein. More specifically, saturation mutagenesis typically utilizes artificial gene sequences synthesized using one or more primers containing degenerate codons for introducing variability into the position(s) being optimized. Each of three positions within a degenerate codon encodes a base such as adenine (A), cytosine (C), thymine (T), or guanine (G), or a degenerate position such as K (representing G and T), M (representing A and C), R (representing A and G), S (representing C and G), W (representing A and T), Y (representing C and T), B (representing C, G, and T), D (representing A, G, and T), H (representing A, C, and T), V (representing A, C, and G), or N (representing A, C, G, and T). For example, the degenerate codon "NDT" includes 12 codons (i.e., N=[A, C, G, T]; D=[A, G, T]; T=[T]), which collectively encode 12 amino acids (Phe, Leu, Ile, Val, Tyr, His, Asn, Asp, Cys, Arg, Ser, and Gly). Likewise, the degenerate codon NNN is considered "fully randomized," as it includes all 64 codons and encodes all 20 naturally occurring amino acids. It will be appreciated that certain amino acids are encoded by more codons than others, such that the exact ratio of encoded amino acids in a given degenerate codon will not be equal. Additionally, degenerate codons are typically selected to minimize the presence of stop codons. For example, restricted degenerate codons "NNK" and "NNS" may be utilized to encode the same number of amino acids as "NNN" (i.e., all 20 natural amino acids), but with a greatly reduced content of encoded stop codons. As such, in certain embodiments, a mixture of degenerate primers may be utilized to achieve desired parameters including redundancy and stop codon content, as well as the representation of select chemical and/or physical characteristics of the amino acids encoded, such as charge, size, electronics, polarity, hydrophilicity, and hydrophobicity. Such mixtures may comprise any number of different degenerate primers in any ratio. Considerations and methods for choosing optimal combinations of degenerate primers will be known to one of skill in the art. For example, computational tools for selecting particular degenerate codons and are known and may be utilized to control the corresponding encoded amino acids. Specific primers suitable for introducing particular mutations described above are provided herein in the examples below.

It is to be understood that the parent proteins/enzymes to be evolved can be a wild-type protein or enzyme, or a variant, mutant, etc. In general, parent proteins are selected from cytochrome P450 proteins such as cytochrome P450 BM3. As such, parent polynucleotides for use in creating the mutagenesis library, as well as entire vectors containing nucleic acids encoding the parent protein of interest, may be commercially available, and thus can be prepared, purchased, or otherwise obtained from any suitable commercial or non-commercial source.

Once prepared, (e.g. via introducing one or more mutations into a target gene encoding the parent cytochrome P450, such as with one or more of the techniques described above), evolved polynucleotides are cloned into a suitable vector and introduced into a suitable host cell (e.g. via transformation, transfection, infection, etc.) for expression, according to methods well known in the art. Appropriate vectors, host cells, and techniques will be readily selected by one of skill in the art. Examples of suitable vectors generally include various plasmids and viruses known to be compatible with host cells that express oxidation enzymes or oxygenases. Examples of suitable host cells generally include bacterial cells (e.g. from *Escherichia coli* (*E. coli*), *Bacillus, Pseudomonas*, etc.), yeast cells (e.g. from *Saccharomyces cerevisiae*, etc.), fungal cells (e.g. from *Aspergillus*), insect cells, etc. In certain embodiments, plant and/or other animal cells (e.g. mammalian, human, etc.) may also be utilized. Such host cells may be transformed, transfected or infected as appropriate by any suitable method, including electroporation, chemical-mediated DNA uptake, fungal infection, viral infection, microinjection, microprojectile transformation, and the like, or other techniques known in the art.

Once expressed, evolved cytochrome P450 variants are then tested/screened (e.g. in vivo or in vitro via combination with the organosilicon compound, as described below, with silane oxidation/silanol formation monitored via chromatographic and/or spectroscopic methods) to identify particular variants exhibiting a desired activity or property and, optimally, activity greater (i.e., more beneficial) than the parent cytochrome P450 protein. Any such identified variants may then isolated, purified, and/or characterized as desired, and optionally subjected to assays designed to further test functional activity, etc. It will be appreciated that identified variants may also be utilized in further rounds of directed evolution, i.e., as a parent protein from which a subsequent generation of cytochrome P450 variants is prepared (e.g. via the procedures described above). Various aspects of the directed evolution techniques suitable for use in engineering and/or optimizing the cytochrome P450 variants will be better understood in view of certain procedures set form in the Examples below.

As will be appreciated from the description of the directed evolution process above, as well as the additional description below, a nucleic acid (i.e., a nucleic acid molecule) encoding the cytochrome P450 variant is also provided herein. The nucleic acid molecule may be a DNA molecule or an RNA molecule, and in any form (e.g. such as any of the forms described above) suitable for use in preparing the cytochrome P450 variant. As such, the nucleic acid molecule may encode the cytochrome P450 variant or a precursor thereof, e.g. a pro- or pre-proform of the cytochrome P450 variant, optionally comprising a signal sequence or other heterologous amino acid portion(s) (e.g. a tag) for secretion and/or purification. For example, an affinity tag (e.g. a His6-tag, a glutathione S-transferase (GST), etc.) may be added to the N- and/or C-terminus of a cytochrome P450 variant protein expressed from an expression vector utilizing the nucleic acid in order to facilitate protein purification.

In some embodiments, the nucleic acid molecule comprises a nucleic acid sequence having at least 70% identity to the nucleic acid sequence set forth in SEQ ID NO:5, such as at least 75, alternatively at least 80, alternatively at least 85, alternatively at least 90, alternatively at least 95% identity to the nucleic acid sequence set forth in SEQ ID NO:5. In particular embodiments, the nucleic acid molecule comprises an nucleic acid sequence having greater than 95%, alternatively greater than 96%, alternatively greater than 97%, alternatively greater than 98%, alternatively greater than 99%, alternatively 100% identical to the nucleic acid sequence set forth in SEQ ID NO:5. In certain embodiments, the nucleic acid molecule comprises a nucleic acid sequence that encodes a cytochrome P450 variant comprises an amino acid sequence having greater than 95%, alternatively greater than 96%, alternatively greater than 97%, alternatively greater than 98%, alternatively greater than 99%, alternatively 100% identical to the nucleic acid sequence set forth in SEQ ID NO:5.

In some embodiments, the nucleic acid molecule comprises a nucleic acid sequence having at least 70% identity to the nucleic acid sequence set forth in SEQ ID NO:6, such as at least 75, alternatively at least 80, alternatively at least 85, alternatively at least 90, alternatively at least 95% identity to the nucleic acid sequence set forth in SEQ ID NO:6. In particular embodiments, the nucleic acid molecule comprises an nucleic acid sequence having greater than 95%, alternatively greater than 96%, alternatively greater than 97%, alternatively greater than 98%, alternatively greater than 99%, alternatively 100% identical to the nucleic acid sequence set forth in SEQ ID NO:6. In certain embodiments, the nucleic acid molecule comprises a nucleic acid sequence that encodes a cytochrome P450 variant comprises an amino acid sequence having greater than 95%, alternatively greater than 96%, alternatively greater than 97%, alternatively greater than 98%, alternatively greater than 99%, alternatively 100% identical to the nucleic acid sequence set forth in SEQ ID NO:6.

In some embodiments, the nucleic acid molecule comprises a nucleic acid sequence having at least 70% identity to the nucleic acid sequence set forth in SEQ ID NO:7, such as at least 75, alternatively at least 80, alternatively at least 85, alternatively at least 90, alternatively at least 95% identity to the nucleic acid sequence set forth in SEQ ID NO:7. In particular embodiments, the nucleic acid molecule comprises an nucleic acid sequence having greater than 95%, alternatively greater than 96%, alternatively greater than 97%, alternatively greater than 98%, alternatively greater than 99%, alternatively 100% identical to the nucleic acid sequence set forth in SEQ ID NO:7. In certain embodiments, the nucleic acid molecule comprises a nucleic acid sequence that encodes a cytochrome P450 variant comprises an amino acid sequence having greater than 95%, alternatively greater than 96%, alternatively greater than 97%, alternatively greater than 98%, alternatively greater than 99%, alternatively 100% identical to the nucleic acid sequence set forth in SEQ ID NO:7.

In some embodiments, the nucleic acid molecule comprises a nucleic acid sequence having at least 70% identity to the nucleic acid sequence set forth in SEQ ID NO:8, such as at least 75, alternatively at least 80, alternatively at least 85, alternatively at least 90, alternatively at least 95% identity to the nucleic acid sequence set forth in SEQ ID NO:8. In particular embodiments, the nucleic acid molecule comprises an nucleic acid sequence having greater than 95%, alternatively greater than 96%, alternatively greater than 97%, alternatively greater than 98%, alternatively greater than 99%, alternatively 100% identical to the nucleic acid sequence set forth in SEQ ID NO:8. In certain embodiments, the nucleic acid molecule comprises a nucleic acid sequence that encodes a cytochrome P450 variant comprises an amino acid sequence having greater than 95%, alternatively greater than 96%, alternatively greater than 97%, alternatively greater than 98%, alternatively greater than 99%, alternatively 100% identical to the nucleic acid sequence set forth in SEQ ID NO:8.

In certain embodiments, the nucleic acid molecule is generated via gene synthesis (i.e., is a synthetic nucleic acid). In some such embodiments, the synthetic nucleic acid is codon-optimized for expression. For example, in certain embodiments, the synthetic nucleic acid may be engineered to lack certain internal restriction endonuclease sites. Likewise, in certain embodiments, the nucleic acid molecule may comprise, or otherwise may be operatively linked to, an expression control sequence, i.e., a sequence allowing expression of the nucleic acid molecule in a desired host cell. Examples of suitable expression control sequences and vectors are known in the art.

Accordingly, a non-human organism transformed or transfected with the nucleic acid molecule (i.e., a transgenic organism) is also provided, and may be prepared by known methods of homologous recombination or other techniques for genetic transfer, such as any of those described herein.

For example, the nucleic acid molecule may be located on a vector. As such, an expression vector comprising a nucleic acid sequence that encodes the cytochrome P450 variant is also provided. In general, the expression vector is not limited, and may be a viral vector, a plasmid, a phage, a phagemid, a cosmid, a fosmid, a bacteriophage (e.g. a bacteriophage P1-derived vector (PAC)), a baculovirus vector, a yeast plasmid, an artificial chromosome (e.g. a bacterial artificial chromosome (BAC), a yeast artificial chromosome (YAC), a mammalian artificial chromosome (MAC), a human artificial chromosome (HAC), etc.), or other such vectors capable of facilitating the expression of the cytochrome P450 variant, which will be readily apparent to one of skill in the art.

The expression vector may include chromosomal, non-chromosomal, and/or synthetic DNA sequences. In certain embodiments, the expression vector comprises a promotor operably linked to nucleic acid sequence that encodes the cytochrome P450 variant. In such embodiments, the promoter is not particularly limited, and may be selected from viral, bacterial, archaeal, fungal, insect, plant, and/or mammalian promoters. In certain embodiments, the promoter is a constitutive promoter. In some embodiments, the promoter is an inducible promoter. In other embodiments, the promoter is a tissue-specific, environmentally regulated, and/or developmentally regulated.

Examples of expression vectors include pCWori vectors, pET vectors (e.g. pET22), pQE vectors, pBluescript vectors, pNH vectors, lambda-ZAP vectors, pKLAC1 vectors, pKLAC2 vectors, pMT vectors, BacPak baculoviral vectors, pSyn_1 vectors, pCR-TOPO vectors, pChlamy_1 vectors, pAdeno-X adenoviral vectors, and pBABE retroviral vectors, and the like, which are available from various commercial suppliers. Additional examples of expression vectors include ptrc99a, pKK223-3, pDR540, pRIT2T, pRSET, pGEM1, pMAL, pBR322 (i.e., ATCC37017), pXT1, pSG5, pSVK3, pBPV, pMSG, pSVLSV40, pcDNA3.3, pcDNA4/TO, pcDNA6/TR, pLenti6/TR, and the like, as well as derivatives and modifications thereof. It will be appreciated that any other vector replicable and viable in the host cell may also be utilized.

The cytochrome P450 variant may be expressed in whole cells, such as bacterial cells, archaeal cells, yeast cells, fungal cells, insect cells, plant cells, mammalian cells, etc. Examples of bacterial host cells include BL21 *E. coli*, DE3 strain *E. coli*, *E. coli* M15, DH5a, DH10β, HB101, T7 Express Competent *E. coli* (NEB), *B. subtilis* cells, *Pseudomonas fluorescens* cells, and cyanobacterial cells such as *Chlamydomonas reinhardtii* cells and Synechococcus elongates cells. Examples of archaeal host cells include *Pyrococcus furiosus, Metallosphera sedula, Thermococcus litoralis, Methanobacterium thermoautotrophicum, Methanococcus jannaschii, Pyrococcus abyssi, Sulfolobus solfataricus, Pyrococcus woesei*, and *Sulfolobus shibatae*. Examples of fungal host cells include yeast cells from the genera *Saccharomyces* (e.g. *S. cerevisiae*), *Pichia* (e.g. *P. Pastoris*), *Kluyveromyces* (e.g. *K. lactis*), *Hansenula*, and *Yarrowia*, as well as filamentous fungal cells from the genera *Aspergillus, Trichoderma*, and *Myceliophthora*. Examples of insect host cells include Sf9 cells from *Spodoptera frugiperda*, Sf21 cells from *Spodoptera frugiperda*, Hi-Five cells, BTI-TN-5B1-4 *Trichophusia ni* cells, as well as Schneider 2 (S2) and Schneider 3 (S3) cells from *Drosophila melanogaster*. Examples of mammalian host cells include HEK293 cells, HeLa cells, CHO cells, COS cells, Jurkat cells, NS0 hybridoma cells, baby hamster kidney (BHK) cells, MDCK cells, and NIH-313 fibroblast cells. Examples of plant host cells include those from tobacco, tomato, potato, maize, rice, lettuce, and spinach plants, as well as other plant cells having short generation times and/or yield reasonable biomass with standard cultivation techniques. It will be appreciated that these host cells also exemplify the non-human organism comprising the nucleic acid molecule according to certain embodiments, as described above.

In some embodiments, the cytochrome P450 variant exhibits enhanced activity compared to a corresponding wild-type cytochrome P450 protein, with respect to the silicon oxidization of the method. For example, in certain embodiments, the cytochrome P450 variant exhibits an activity of at least 1.5 times higher than the corresponding wild-type protein, such as an activity of at least 2, alternatively at least 5, alternatively at least 10, alternatively at least 20, alternatively at least 25, alternatively at least 50, alternatively at least 100, alternatively at least 250, alternatively at least 500, alternatively at least 1000, alternatively at least 2000 times higher than the corresponding wild-type protein (i.e., when assessed under the same conditions in accordance with the method).

In some embodiments, the activity of the cytochrome P450 variant is expressed in terms of total turnover number (TTN), i.e., the maximum number of substrate molecules (e.g. molecules of the organosilicon compound) the cytochrome P450 variant can convert (i.e., oxidize) before becoming inactivated. For example, in some embodiments, the cytochrome P450 variant exhibits a TTN of at least 1.5 times higher than the corresponding wild-type protein, such as an activity of at least 2, alternatively at least 4, alternatively at least 5, alternatively at least 10, alternatively at least 15, alternatively at least 20, alternatively at least 25, alternatively at least 50, alternatively at least 100, alternatively at least 500, alternatively at least 1000 times higher than the corresponding wild-type protein.

In certain embodiments, the cytochrome P450 variant exhibits a TTN of from 1 to 100, such as a TTN of from 2 to 100, alternatively from 5 to 100, alternatively from 10 to 100, alternatively from 15 to 100, alternatively from 25 to 100, alternatively from 50 to 100, alternatively from 75 to 100. In other embodiments, the cytochrome P450 variant exhibits a TTN of from 100, such as a TTN of from 150 to 1000, alternatively from 200 to 1000, alternatively from 300 to 1000, alternatively from 400 to 1000, alternatively from 500 to 1000, alternatively from 600 to 1000, alternatively from 700 to 1000, alternatively from 800 to 1000, alternatively from 900 to 1000. In yet other embodiments, the cytochrome P450 variant exhibits a TTN greater than 1000, such as a TTN of at least 1100, alternatively at least 1500, alternatively at least 2000, alternatively at least 2500, alternatively at least 5000, alternatively at least 7500, alternatively at least 10000, alternatively at least 15000, alternatively at least 20000.

In some embodiments, the activity of the cytochrome P450 variant is expressed in terms of turnover frequency (TOF). For example, in some embodiments, the cytochrome P450 variant exhibits a TOF of at least 1.5 times higher than the corresponding wild-type protein, such as an activity of at least 2, alternatively at least 3, alternatively at least 4, alternatively at least 5, alternatively at least 10, alternatively at least 12, alternatively at least 15, alternatively at least 20, alternatively at least 25, alternatively at least 50, alternatively at least 100, alternatively at least 200 times higher than the corresponding wild-type protein (i.e., when assessed under the same conditions in accordance with the method).

In certain embodiments, the activity of the cytochrome P450 variant is expressed in terms of selectivity. For example, in some embodiments, the cytochrome P450 variant exhibits a selectivity for oxidizing a silyl hydride (i.e., Si—H) over a hydrocarbon or alkene group of a substrate, such as a selectivity of at least 2:1 [Si]:[C], where [Si] represents equivalents silicon centers oxidized and [C] represents equivalents carbon centers oxidized for a given substrate. In some such embodiments, the cytochrome P450 variant exhibits a selectivity of at least 5:1, alternatively at least 10:1, alternatively at least 50:1, alternatively at least 100:1, alternatively at least 500:1, alternatively at least 1000:1, alternatively at least 5000:1, alternatively at least 10000:1 1 [Si]:[C]. In specific embodiments, the cytochrome P450 variant exhibits an oxidative selectivity such that the amount of carbon-centered oxidation is negligible, essentially nonexistent, or undetectable with standard characterization/monitoring techniques.

The cytochrome P450 variant may be utilized in the method in any form. For example, in certain embodiments, the cytochrome P450 variant is utilized as a whole cell catalyst, i.e., a composition comprising host cells expressing the cytochrome P450 variant. Examples of such host cells, as well as various techniques for preparing such whole cell catalysts comprising the cytochrome P450 variant are described above. As such, in some embodiments, the method comprises preparing a whole cell catalyst comprising (e.g. expressing) the cytochrome P450 variant, and subsequently combining the whole cell catalyst with the organosilicon compound to prepare the silanol-functional organosilicon compound. In particular embodiments, the cytochrome P450 variant is utilized as a cell lysate, i.e., a composition comprising a lysis product of the whole cell catalyst comprising the cytochrome P450 variant described above. In yet other embodiments, the cytochrome P450 variant is utilized as an isolated enzyme. For example, in such embodiments, the method comprises isolating and/or purifying the cytochrome P450 variant from the host cells expressing the cytochrome P450 variant and/or the cell lysate described above to give an isolated cytochrome P450 variant, which is then combined with the organosilicon compound to prepare the silanol-functional organosilicon compound.

As introduced above, the method of preparing the silanol-functional organosilicon compound is provided comprises combining the cytochrome P450 variant and an organosilicon compound in the presence of oxygen. More specifically, the organosilicon compound comprises at least one silyl hydride group (i.e., a silicon-bonded hydrogen atom) capable of being oxidized to a silanol group to give the silanol-functional organosilicon compound.

The organosilicon compound may vary widely with respect to the other substituents bonded to the silicon atom of the silyl hydride group. In general, the organosilicon compound is a hydridosilane or hydridosiloxane, and thus corresponds to the general formula $R_3Si$—H, where each R is independently selected from hydrocarbyl groups, hydrocarbyloxy groups, and siloxy groups.

Hydrocarbyl groups suitable for R include monovalent hydrocarbon moieties, as well as derivatives and modifications thereof, which may independently be substituted or unsubstituted, linear, branched, cyclic, or combinations thereof, and saturated or unsaturated. With regard to such hydrocarbyl groups, the term "unsubstituted" describes hydrocarbon moieties composed of carbon and hydrogen atoms, i.e., without heteroatom substituents. The term "substituted" describes hydrocarbon moieties where either at least one hydrogen atom is replaced with an atom or group other than hydrogen (e.g. a halogen atom, an alkoxy group, an amine group, etc.) (i.e., as a pendant or terminal substituent), a carbon atom within a chain/backbone of the hydrocarbon is replaced with an atom other than carbon (e.g. a heteroatom, such as oxygen, sulfur, nitrogen, etc.) (i.e., as a part of the chain/backbone), or both. As such, suitable hydrocarbyl groups may comprise, or be, a hydrocarbon moiety having one or more substituents in and/or on (i.e., appended to and/or integral with) a carbon chain/backbone thereof, such that the hydrocarbon moiety may comprise, or be, an ether, an ester, etc. Linear and branched hydrocarbyl groups may independently be saturated or unsaturated and, when unsaturated, may be conjugated or nonconjugated. Cyclic hydrocarbyl groups may independently be monocyclic or polycyclic, and encompass cycloalkyl groups, aryl groups, and heterocycles, which may be aromatic, saturated and nonaromatic and/or non-conjugated, etc. Examples of combinations of linear and cyclic hydrocarbyl groups include alkaryl groups, aralkyl groups, etc. General examples of hydrocarbon moieties suitably for use in or as the hydrocarbyl group include alkyl groups, aryl groups, alkenyl groups, alkynyl groups, halocarbon groups, and the like, as well as derivatives, modifications, and combinations thereof. Examples of alkyl groups include methyl, ethyl, propyl (e.g. iso-propyl and/or n-propyl), butyl (e.g. isobutyl, n-butyl, tert-butyl, and/or sec-butyl), pentyl (e.g. isopentyl, neopentyl, and/or tert-pentyl), hexyl, and the like (i.e., other linear or branched saturated hydrocarbon groups, e.g. having greater than 6 carbon atoms). Examples of aryl groups include phenyl, tolyl, xylyl, naphthyl, benzyl, dimethyl phenyl, and the like, as well as derivatives and modifications thereof, which may overlap with alkaryl groups (e.g. benzyl) and aralkyl groups (e.g. tolyl, dimethyl phenyl, etc.). Examples of alkenyl groups include vinyl, allyl, propenyl, isopropenyl, butenyl, isobutenyl, pentenyl, heptenyl, hexenyl, cyclohexenyl groups, and the like, as well as derivatives and modifications thereof. General examples of halocarbon groups include halogenated derivatives of the hydrocarbon moieties above, such as halogenated alkyl groups (e.g. any of the alkyl groups described above, where one or more hydrogen atoms is replaced with a halogen atom such as F or Cl), aryl groups (e.g. any of the aryl groups described above, where one or more hydrogen atoms is replaced with a halogen atom such as F or Cl), and combinations thereof. Examples of halogenated alkyl groups include fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl, 2,2-difluorocyclopropyl, 2,3-difluorocyclobutyl, 3,4-difluorocyclohexyl, 3,4-difluoro-5-methylcycloheptyl, chloromethyl, chloropropyl, 2-dichlorocyclopropyl, 2,3-dichlorocyclopentyl, and the like, as well as derivatives and modifications thereof. Examples of halogenated aryl groups include chlorobenzyl, pentafluorophenyl, fluorobenzyl groups, and the like, as well as derivatives and modifications thereof.

In certain embodiments, at least one R is a substituted or unsubstituted hydrocarbyl group having from 1 to 12 carbon atoms. For example, in some such embodiments, the at least one R is an independently selected substituted or unsubstituted alkyl group, such as an alkyl group having from 1 to 6, alternatively from 1 to 5, alternatively from 1 to 4 carbon atoms. Specific examples of alkyl groups include methyl groups, ethyl groups, propyl groups (e.g. n-propyl and iso-propyl groups), butyl groups (e.g. n-butyl, sec-butyl, iso-butyl, and tert-butyl groups), pentyl groups, hexyl groups, heptyl groups, etc., and the like, as well as derivatives and/or modifications thereof. Examples of derivatives and/or modifications of such alkyl groups include substituted versions thereof. For example, R may comprise, alternatively may be, a hydroxyl ethyl group, which will be understood to be a derivative and/or a modification of the ethyl groups described above. Likewise, R may comprise, alternatively may be, an acetoacetoxyethyl group, which will also be understood to be a derivative and/or a modification of the ethyl groups described above (e.g. as an acetoacetoxy-substituted ethyl group), as well as a derivative and/or a modification of other hydrocarbyl groups described above (e.g. a hexyl group substituted with an ester and a ketone, etc.). In these or other embodiments, at least one R is an independently selected substituted or unsubstituted alkenyl groups having from 2 to 6 carbon atoms, such as from 2 to 5, alternatively from 2 to 4, alternatively from 2 to 3 carbon atoms.

In particular embodiments, at least one R is independently selected from substituted and unsubstituted aryl, alkaryl, and aralkyl groups having from 1 to 12 carbon atoms, such as from 2 to 12, alternatively from 2 to 10, alternatively from 3 to 10, alternatively from 3 to 8, alternatively from 4 to 8 carbon atoms. In particular embodiments, the at least one R is independently selected from substituted and unsubstituted aryl, alkaryl, and aralkyl groups having from 5 to 12 heteroatoms (e.g. C, O, N, S, P, etc.), such as from 6 to 12, alternatively from 6 to 10, alternatively from 6 to 9, alternatively from 6 to 8 heteroatoms.

Hydrocarbyloxy groups suitable for R include those having the general formula —OR', where R' is one of the hydrocarbyl groups set forth above with respect to R. Examples of such hydrocarbyloxy groups include alkoxy and aryloxy groups. Examples of alkoxy groups include methoxy, ethoxy, propoxy, butoxy, benzyloxy, and the like, as well as derivatives and modifications thereof. Examples of aryloxy groups include phenoxy, tolyloxy, pentafluorophenoxy, and the like, as well as derivatives and modifications thereof.

Examples of suitable siloxy groups suitable for R include [M], [D], [T], and [Q] units/siloxy groups, which, as understood in the art, each represent structural units of individual functionality present in siloxanes, such as organosiloxanes and organopolysiloxanes. More specifically, [M] represents a monofunctional unit of general formula $R''_3SiO_{1/2}$; [D] represents a difunctional unit of general formula $R''_2SiO_{2/2}$; [T] represents a trifunctional unit of general formula $R''SiO_{3/2}$; and [Q] represents a tetrafunctional unit of general formula $SiO_{4/2}$, as shown by the general structural moieties below:

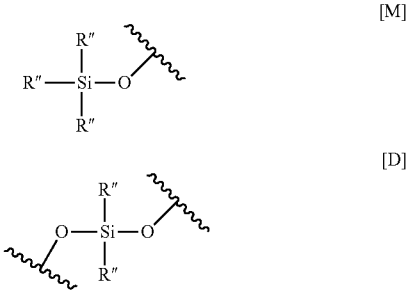

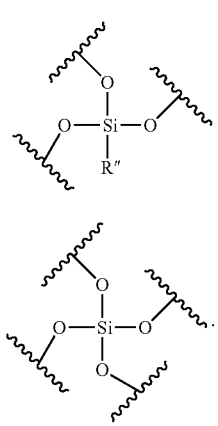

In these general structural moieties, each R" is independently a monovalent or polyvalent substituent. As understood in the art, specific substituents suitable for each R" are not limited, and may be monoatomic or polyatomic, organic or inorganic, linear or branched, substituted or unsubstituted, aromatic, aliphatic, saturated or unsaturated, and combinations thereof. Typically, each R" is independently selected from hydrocarbyl groups, alkoxy and/or aryloxy groups, and siloxy groups. As such, each R" may independently be a hydrocarbyl group of formula —R' or an alkoxy or aryloxy group of formula —OR', where R' is as defined above (e.g. including any of the hydrocarbyl groups set forth above with respect to R), or a siloxy group represented by any one, or combination, of [M], [D], [T], and/or [Q] units described above.

In certain embodiments, at least one R is a siloxy group of formula $R''_3SiO$— such that the organosilicon compound may be characterized or otherwise referred to as a siloxane, where each R" is independently selected and defined above. In some such embodiments, each R" is substituted or unsubstituted hydrocarbyl group having from 1 to 6 carbon atoms. In specific embodiments, each R" is an alkyl group having from 1 to 6 carbon atoms, such as from 1 to 5, alternatively from 1 to 4, alternatively from 1 to 3, alternatively from 1 to 2, alternatively 1 carbon atom(s). In particular embodiments, each R" is methyl, such that the siloxy group is a trimethylsiloxy group.

As introduced above, R is independently selected. As such, any R of the organosilicon compound may be the same as or different from any other R, e.g. in terms of type, identity, or characteristics of the substituents. For ease of reference, the general formula for the organosilicon compound above may be rewritten as the following general formula:

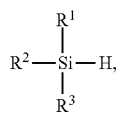

where each $R^1$, $R^2$, and $R^3$ are independently selected from substituted or unsubstituted hydrocarbyl groups, hydrocarbyloxy groups, and siloxy groups, such as those described above with respect to R.

With respect to the preceding structure, in certain embodiments, each of $R^1$, $R^2$, and $R^3$ is independently selected from alkyl groups having from 1 to 6 carbon atoms, hydrocarbyloxy groups having from 1 to 12 carbon atoms, alkenyl groups having from 2 to 6 carbon atoms, and siloxy groups of formula $R^4_3SiO$—, where each $R^4$ is an independently selected hydrocarbyl group having from 1 to 6 carbon atoms, where $R^1$, $R^2$, and $R^3$ are each independently selected from substituted or unsubstituted hydrocarbyl groups, hydrocarbyloxy groups, and siloxy groups. In some such embodiments, $R^1$ is an alkyl group having from 1 to 6 carbon atoms, $R^2$ is an alkyl group having from 1 to 6 carbon atoms or a hydrocarbyloxy group having from 6 to 12 carbon atoms, and $R^3$ is an alkyl group having from 1 to 6 carbon atoms, a hydrocarbyloxy group having from 6 to 12 carbon atoms, an alkenyl groups having from 2 to 6 carbon atoms, or a trimethylsiloxy group.

Particular examples of compounds suitable for use as the organosilicon compound include dimethyl(phenyl)silane, ethyl(methyl)(phenyl)silane, methyl(phenyl)(vinyl)silane, benzyldimethylsilane, dimethyl(p-tolyl)silane, dimethyl (thiophen-2-yl)silane, triethylsilane, butyldimethylsilane, methyldiphenylsilane, pentamethyldisiloxane, and the like, as well as derivatives, modifications, and combinations thereof. It is to be appreciated that these exemplary compounds are utilized to illustrate the varied scope of substrates suitable for use in the method (i.e., with the cytochrome P450 variant), and are not limiting with respect to the any particular organosilicon compounds that may be utilized in the method, which will be selected by those of skill in the art in view of the description and examples herein.

The organosilicon compound may be prepared or otherwise obtained, i.e., as a prepared compound. Methods of preparing the organosilicon compound are known in the art, with such compounds and suitable starting materials commercially available from various suppliers. Preparing the organosilicon compound when part of the method, is typically performed prior to combining the same with the cytochrome P450 variant.

Likewise, the organosilicon compound may be utilized in any form, such as neat (i.e., absent solvents, carrier vehicles, diluents, etc.), or disposed in a carrier vehicle, such as a solvent or dispersant. For example, the organosilicon compound may be disposed in a carrier vehicle, such as one of those described herein. It will be appreciated that the acryloxy-functional organosilicon monomer may be combined with the carrier vehicle, if utilized, prior to, during, or after being combined with the cytochrome P450 variant. In some embodiments, the organosilicon compound is utilized free from, alternatively substantially free from carrier vehicles. For example, in certain embodiments, the method may comprise stripping the organosilicon compound of volatiles and/or solvents, or distilling the organosilicon compound from solvents, volatiles, etc., to prepare the organosilicon compound for use in the method.

The organosilicon compound may comprise but one type of organosilicon compound or, alternatively, may comprise more than one type of organosilicon compound, such as two, three, or more acryloxy-functional organosilicon monomers that differ from one another with regard to at least one of variables $R^1$, $R^2$, and $R^3$ defined and described above.

The organosilicon compound may be utilized in any amount, which will be selected by one of skill in the art, e.g. dependent upon the particular components selected for reacting, the reaction parameters employed, the scale of the reaction (e.g. total amounts of the organosilicon compound to be reacted and/or silanol-functional organosilicon compound to be prepared), etc.

The method of preparing the silanol-functional organosilicon compound comprises combining the cytochrome P450 variant and the organosilicon compound in the presence of oxygen and, optionally, any other components utilized (collectively, the "reaction components"). As will be understood by those of skill in the art, there is generally no proactive step required for the cytochrome P450 variant-facilitated reaction of the organosilicon compound and oxygen beyond combining the components together. As introduced above, the reaction of the method may be generally defined or otherwise characterized as an oxidation and/or hydroxylation reaction, and certain parameters and conditions of the reaction may be selected by those known in the art of such reactions in order to prepare the silanol-functional organosilicon.

Typically, the reaction components are reacted in a vessel or reactor to prepare the silanol-functional organosilicon compound. More specifically, the reaction components are typically combined in the vessel to prepare a reaction mixture, such that the silanol-functional organosilicon compound is prepared from the reaction mixture.

As introduced above, the reaction mixture may comprise components other than the cytochrome P450 variant, the organosilicon compound, and oxygen. For example, the cytochrome P450 variant and the organosilicon compound are typically combined in the presence of a carrier vehicle (e.g. a solvent, diluent, fluid, etc., or a combination thereof), such that the reaction mixture comprises a solution, emulsion, suspension, slurry, biphasic mixture, or combinations thereof. The particular solvents, carriers, and/or diluents utilized, and the respective amounts thereof employed, will be independently selected by one of skill in the art, e.g. based the particular reaction components being utilized, the particular silanol-functional organosilicon compound being prepared, the scale of the reaction, etc. For example, it is understood by those of skill in the art that biocatalytic reactions may be conducted heterogeneously, e.g. with one or more components suspended, but not dissolved, in the carrier vehicle. Typically, however, certain reaction components are employed as homogeneous mixtures (i.e., prior to forming the reaction mixture) and/or the reaction mixture itself is substantially homogeneous. In general, solvents, carriers, and/or diluents utilized will be selected to help fluidize and/or compatibilize one or more of the reaction components, without promoting undesired reactions of the reaction components. As such, examples of particular carrier vehicles include solvents, fluids, etc. suitable to sufficiently carry, dissolve, and/or disperse any component(s) of the reaction mixture during the preparation of the silanol-functional organosilicon compound.

Examples of suitable solvents include aqueous solvents (e.g. water and water miscible organic solvents), organic solvents, fluids, oil (e.g. an organic oil and/or a silicone oil), etc., as well as combinations thereof. Typically, the carrier vehicle comprises an aqueous solvent comprising, alternatively consisting essentially of, water. However, in certain embodiments, additional and/or alternative carrier fluids and/or diluents may also be utilized, such as any of those described herein. For example, in some embodiments, the carrier vehicle comprises an organic solvent. Examples of organic solvents include those comprising an alcohol, such as methanol, ethanol, isopropanol, butanol, and n-propanol; a ketone, such as acetone, methylethyl ketone, and methyl isobutyl ketone; an aromatic hydrocarbon, such as benzene, toluene, and xylene; an aliphatic hydrocarbon, such as heptane, hexane, and octane; a glycol ether, such as propylene glycol methyl ether, dipropylene glycol methyl ether, propylene glycol n-butyl ether, propylene glycol n-propyl ether, and ethylene glycol n-butyl ether; an acetate, such as ethyl acetate, butyl acetate, ethylene glycol monoethyl ether acetate, and propylene glycol methyl ether acetate; a halogenated hydrocarbon, such as dichloromethane, 1,1,1-trichloroethane, and chloroform; dimethyl sulfoxide; dimethyl formamide, acetonitrile; tetrahydrofuran; white spirits; mineral spirits; naphtha; n-methylpyrrolidone; and the like, as well as derivatives, modifications, and combination thereof. In certain embodiments, the carrier vehicle comprises a polar organic solvent, such as a solvent compatible with water. Specific examples of such polar organic solvents include methanol, ethanol, 1-propanol, 2-propanol, 2-methyl-2-propanol, 2-butanone, tetrahydrofuran, acetone, and combinations thereof.

In certain embodiments, the carrier vehicle comprises an organic fluid, which typically comprises an organic oil including a volatile and/or semi-volatile hydrocarbon, ester, and/or ether. General examples of such organic fluids include volatile hydrocarbon oils, such as $C_6$-$C_{16}$ alkanes, $C_8$-$C_{16}$ isoalkanes (e.g. isodecane, isododecane, isohexadecane, etc.), $C_8$-$C_{16}$ branched esters (e.g. isohexyl neopentanoate, isodecyl neopentanoate, etc.), and the like, as well as derivatives, modifications, and combinations thereof. Additional examples of suitable organic fluids include aromatic hydrocarbons, aliphatic hydrocarbons, alcohols having more than 3 carbon atoms, aldehydes, ketones, amines, esters, ethers, glycols, glycol ethers, acetates, alkyl halides, aromatic halides, and combinations thereof. Hydrocarbons include isododecane, isohexadecane, Isopar L ($C_{11}$-$C_{13}$), Isopar H ($C_{11}$-$C_{12}$), hydrogentated polydecene. Ethers and esters include isodecyl neopentanoate, neopentylglycol heptanoate, glycol distearate, dicaprylyl carbonate, diethylhexyl carbonate, propylene glycol n-butyl ether, ethyl-3 ethoxypropionate, propylene glycol methyl ether acetate, tridecyl neopentanoate, propylene glycol methylether acetate (PG-MEA), propylene glycol methylether (PGME), octyldodecyl neopentanoate, diisobutyl adipate, diisopropyl adipate, propylene glycol dicaprylate/dicaprate, octyl ether, octyl palmitate, and combinations thereof.

In some embodiments, the carrier vehicle comprises a silicone fluid. The silicone fluid is typically a low viscosity and/or volatile siloxane. In some embodiments, the silicone fluid is a low viscosity organopolysiloxane, a volatile methyl siloxane, a volatile ethyl siloxane, a volatile methyl ethyl siloxane, or the like, or combinations thereof. Typically, the silicone fluid has a viscosity at 25° C. in the range of 1 to 1,000 mm$^2$/sec. Specific examples of suitable silicone fluids include hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadecamethylheptasiloxane, heptamethyl-3-{(trimethylsilyl)oxy)}trisiloxane, hexamethyl-3,3, bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes, caprylyl methicone, hexamethyldisiloxane, heptamethyloctyltrisiloxane, hexyltrimethicone, and the like, as well as derivatives, modifications, and combinations thereof. Additional examples of suitable silicone fluids include polyorganosiloxanes with suitable vapor pressures, such as from $5\times10^{-7}$ to $1.5\times10^{-6}$ m$^2$/s.

Other carrier vehicles may also be utilized. For example, in some embodiments, the carrier vehicle comprises an ionic liquid. Examples of ionic liquids include anion-cation combinations. Generally, the anion is selected from alkyl sulfate-based anions, tosylate anions, sulfonate-based anions, bis(trifluoromethanesulfonyl)imide anions, bis(fluorosulfonyl) imide anions, hexafluorophosphate anions, tetrafluoroborate anions, and the like, and the cation is selected from imidazolium-based cations, pyrrolidinium-based cations, pyridinium-based cations, lithium cation, and the like. However, combinations of multiple cations and anions may also be utilized. Specific examples of the ionic liquids typically include 1-butyl methylpyrrolidinium bis(trifluoromethanesulfonyl)imide, 1-methyl-1-propylpyrrolidinium bis-(trifluoromethanesulfonyl)imide, 3-methyl-1-propylpyridinium bis(trifluoromethanesulfonyl)imide, N-butyl-3-methylpyridinium bis(trifluoromethanesulfonyl)imide, 1-methyl-1-propylpyridinium bis(trifluoromethanesulfonyl)imide, diallyldimethylammonium bis(trifluoromethanesulfonyl)imide, methyltrioctylammonium bis(trifluoromethanesulfonyl)imide, 1-butyl-3-methylimidazolium bis(trifluoromethanesulfonyl)imide, 1,2-dimethyl-3-propylimidazolium bis(trifluoromethanesulfonyl)imide, 1-ethyl-3-methylimidazolium bis(trifluoromethanesulfonyl)imide, 1-vinylimidazolium.bis(trifluoromethanesulfonyl)imide, 1-allyl imidazolium bis(trifluoromethanesulfonyl)imide, 1-allyl-3-methylimidazolium bis(trifluoromethanesulfonyl)imide, lithium bis(trifluoromethanesulfonyl)imide, and the like, as well as derivatives, modifications, and combinations thereof.

The carrier vehicle may comprise a combination of different vehicles/solvents/diluents, etc., which may be miscible or immiscible with one another. For example, as introduced above, the reaction mixture may be homogenous or heterogeneous (e.g. in the form of an emulsion, such as a water-in-oil emulsion, silicone-in-oil emulsion, oil-in-water emulsion, oil-in-silicone emulsion, etc.

In certain embodiments, the reaction mixture may comprise one or more additional components, which will be selected by those of skill in the art in view of the particular parameters employed in the method. Examples of such additional components include buffers (e.g. M9-N buffer, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline solutions, sodium citrate, sodium acetate, sodium borate, etc.), reducing agents and/or cofactors (e.g. NADPH, NADH, sodium dithionite, dithiothreitol (DTT), β-mercaptoethanol (BME), tris(2-carboxyethyl)phosphine (TCEP), etc.), chelators (e.g. 2-({2-[bis(carboxymethyl)amino]ethyl} (carboxymethyl)amino)acetic acid (EDTA), ethylene glycol-bis(2-aminoethylether)-N,N,N',N'-tetraacetic acid (EGTA), 1,2-bis(o-aminophenoxy)ethane-N,N,N',N'-tetraacetic acid (BAPTA), etc.), salts (e.g. halide salts of sodium, calcium, potassium, magnesium, etc., such as NaCl, KCl, CaCl$_2$, etc.), cosolvents and/or diluents (e.g. dimethylsulfoxide, dimethylformamide, ethanol, methanol, isopropanol, glycerol, tetrahydrofuran, acetone, acetonitrile, acetic acid, etc.), denaturants (e.g. urea, guandinium hydrochloride, etc.), detergents (sodium dodecylsulfate and Triton-X 100) and/or surfactants (e.g. cationic, anionic, nonionic, and/or zwitterionic surfactants), sugars (e.g. glucose, sucrose, etc.), as well as combinations thereof.

When utilized, such additional components can be used in any amount, loading, and/or to suitable concentration, which can be readily determined by one of skill in the art. In general, such components are typically present in the reaction mixture, when utilized, at concentrations of from 1 µM to 1 M, such as in concentration of about 1, 10, or 100 µM, about 1, 10, 25, 50, 100, 250, or 500 mM, or about 1 M. In some embodiments, a reducing agent is used in a sub-stoichiometric amount with respect to the organosilicon compound. Cosolvents, when utilized, may be pressing in the reaction mixture in an amount of from 1 to 75% (v/v), such from 1 to 50, alternatively from 1 to 25, alternatively from 1 to 10, alternatively from 1 to 5%.

As introduced above, the cytochrome P450 variant may be utilized in the method in any form, such as in the form of a whole cell catalyst, a cell lysate, or a protein isolate. As such, it will be appreciated that the reaction mixture may comprise a suspension of such cells and/or cellular components. For example, the reaction may be conducted in vivo with intact cells expressing cytochrome P450 variant such that, in some embodiments, the method comprises preparing a suspension of the whole cell catalyst in a suitable medium supplemented with nutrients (e.g. mineral micronutrients, glucose and other fuel sources, cofactors, if necessary for the reaction, etc.). As will be understood by those of skill in the art, yields of the silanol-functional organosilicon compound may be controlled, in part, by selecting the cell density in the reaction mixtures. For example, in some embodiments, the reaction mixture comprises a cellular suspension exhibiting optical densities in the range of from 0.1 to about 50 at 600 nm may be employed. However, it will be appreciated that densities outside this range may also be utilized, e.g. depending on the type of host cell utilized, the specific cytochrome P450 variant being expressed, etc.

In certain embodiments, the reaction mixture is pH adjusted and/or controlled. The pH may be monitored, adjusted, controlled, etc. by any method known in the art, with the pH adjusting generally comprising adding an acid (e.g. HCl), a base (e.g. NaOH), a buffer, or combinations thereof, to the reaction mixture itself (i.e., once formed) or to one or more of the reaction components. For example, in certain embodiments, the cytochrome P450 variant is utilized in a pH adjusted and/or controlled composition prior to being combined with the organosilicon compound. In general, the reaction is carried out at a pH of from 7 to about 9, alternatively of about 8. For example, in certain embodiments, the reaction mixture is formulated to comprise a pH (e.g. upon formation and/or during the reaction) of from 7.5 to 8.5, such as from 7.6 to 8.4, alternatively from 7.7 to 8.3, alternatively from 7.8 to 8.2, alternatively from 7.9 to 8.1. In particular embodiments, the pH of the reaction mixture is adjusted to and/or maintained at a pH of about 8 during the reaction. It is to be appreciated that values outside of these ranges may also be utilized, as will be understood by those of skill in the art in view of the description herein. For example, in particular embodiments, the particular pH of the reaction mixture will typically be adjusted to optimize the activity of the particular cytochrome P450 variant utilized, and may also be varied during the method (e.g. in real-time) to increase/decrease the rate of the oxidation reaction and/or to stop the reaction altogether.

The reaction components can be utilized in varying amounts and/or ratios, which will be selected by those of skill in the art.

Typically, the cytochrome P450 variant is utilized in a catalytic amount, i.e., a substoichiometric amount with respect to the organosilicon compound. For example, in certain embodiments, the cytochrome P450 variant is utilized in an amount of from 0.001 to 10 mol %, such as from 0.001 to 5, alternatively from 0.001 to 1, alternatively from 0.001 to 0.5, alternatively from 0.001 to 0.2, alternatively from 0.01 to 0.2 mol %. In these or other embodiments, the cytochrome P450 variant may be utilized in an amount sufficient to provide the reaction mixture with a concentration of the cytochrome P450 variant of at least 0.1 μM, such as a concentration of from 0.1 to 10, alternatively from 0.1 to 5 μM, alternatively from 0.1 to 1 μM. In some embodiments, the cytochrome P450 variant is utilized in an amount sufficient to provide the reaction mixture with a concentration of the cytochrome P450 variant of from 1 to 15, such as from 1 to 10 μM.

The amount of the organosilicon compound utilized in the method is not limited, and will be selected in view of the size/scale of the reaction, the particular species, properties, and loading of the cytochrome P450 variant utilized, etc. In general, the organosilicon compound is utilized in an amount sufficient to provide the reaction mixture with a concentration of the organosilicon compound of at least 1 mM, such as such as a concentration of from 1 to 50, alternatively from 1 to 25, alternatively from 1 to 15, alternatively from 5 to 15, alternatively from 5 to 10 mM. However, concentrations outside these ranges may also be utilized, and one of skill in the art will select the particular amounts of the organosilicon compound in view of the reaction parameters employed. For example, in some embodiments, the organosilicon compound utilized, e.g. in view of the particular silicone-acrylate polymer being prepared, the particular monomers utilized, etc.

The method may utilize any conditions suitable for promoting the catalytic oxidation of the organosilicon compound in the reaction mixture, and any technique, equipment, or procedure known in the art for achieving such conditions. For example, when the reaction is carried out at an elevated temperature as described below, the vessel or reactor may be heated or cooled in any suitable manner, e.g. via a jacket, mantle, exchanger, bath, coils, etc. Likewise, the method may comprise agitating the reaction mixture during and/or after formation. The agitating may enhance mixing and contacting together the reaction components when combined, e.g. in the reaction mixture. The method may also include independently employing other conditions tailored to enhance the contacting with (e.g. concurrently or sequentially) or without (i.e., independent from, alternatively in place of) the agitating. These or other conditions may be result-effective conditions for enhancing reaction yield of the silanol-functional organosilicon compound. Conditions may independently be an ambient condition (e.g. room temperature and/or atmospheric pressure) and/or a non-ambient parameter (e.g. reduced or elevated temperature and/or reduced or elevated pressure). Additionally, reaction parameters may be dynamically modified, modified in real time (i.e., during the reaction), or may be static (e.g. for the duration of the reaction, or for any portion thereof). For example, temperature, pH, agitation, oxygen content, etc., as well as other parameters, may be independently selected or modified during the reaction.

The reaction is typically conducted under aerobic conditions, as oxygen is a necessary component of the oxidation reaction. However, the reactions can be conducted under an inert atmosphere, such as a nitrogen atmosphere, argon atmosphere, etc., so long as oxygen is introduced to or otherwise present in the reaction mixture. For example, oxygen may be introduced to or otherwise combined with the reaction mixture via exposure of the reaction mixture to ambient atmosphere, via oxygen bubbler, etc. As such, it will be appreciated the reaction mixture is typically prepared in the presence of oxygen, but may be prepared under anaerobic conditions and subsequently combined and/or exposed to oxygen The reaction may be carried out at any temperature compatible with the cytochrome P450 variant. In general, the reaction is carried out at a temperature of from 4 to 45° C. In some embodiments, the reaction is carried out at an elevated temperature. The elevated temperature will be selected and controlled depending on the particular reaction components selected, such as whether the cytochrome P450 variant is provided as an isolated enzyme or in the form of the whole-cell catalyst. Accordingly, the elevated temperature will be readily selected by one of skill in the art in view of the reaction conditions and parameters selected and the description herein. The elevated temperature is typically from greater than 25° C. (ambient temperature) to 45° C., such as from 30 to 45, alternatively from 30 to 40, alternatively from 35 to 40° C. In some embodiments, the method includes heat treating the cytochrome P450. For example, in some such embodiments, the heat treating is conducted by heating the cytochrome P450 to a temperature of about 75° C.

The time during which the reaction to prepare the silanol-functional organosilicon compound is carried out is a function of scale, reaction parameters and conditions utilized, the reaction components selected, etc. In certain embodiments, the reaction may be carried out for a duration of ranging from a few minutes to many hours, such as from 5 minutes to 72 hours. However, the components and conditions of the hydrolysis reaction are typically selected to facilitate hydrolysis during a duration of from 30 minutes to 48 hours, such as from 1 to 48, alternatively from 4 to 48, alternatively from 4 to 24 hours. However, it is to be appreciated that durations outside of these ranges/values may also be utilized, as will be understood by those of skill in the art in view of the description herein. For example, on a relatively large scale (e.g. a scale of greater than 1, alternatively greater than 5, alternatively greater than 10, alternatively greater than 50, alternatively greater than 100 kg), or with a difficult substrate, the reaction may be carried out for one or more days, such as for at least 1, alternatively at least 2, alternatively at least 3, alternatively at least 5 days.

Generally, the reaction of the components of the reaction mixture prepares a reaction product comprising the silanol-functional organosilicon compound. In particular, over the course of the reaction, the reaction mixture comprises increasing amounts of the silanol-functional organosilicon compound being prepared and decreasing amounts of the organosilicon compound utilized in the reaction. Once the reaction is complete (e.g. the organosilicon compound is consumed, no additional amount of silanol-functional organosilicon compound is being prepared, etc.), the reaction mixture may be referred to as the reaction product comprising the silanol-functional organosilicon compound. In this fashion, the reaction product typically includes any remaining amounts of the reaction components, as well as degradation and/or reaction products thereof. For example, when the reaction is carried out in the carrier vehicle, the reaction product will include the solvents/fluids thereof.

Accordingly, in certain embodiments, the method further comprises isolating the silanol-functional organosilicon compound from the reaction product. As used herein with regard to the silanol-functional organosilicon compound of the reaction product, the term "isolating" refers to a process of increasing the relative concentration of the silanol-functional organosilicon compound as compared to other compounds in combination therewith (e.g. in the reaction product or a purified version thereof). As such, as is understood in the art, isolating may comprise removing the other compounds from such a combination (i.e., decreasing the amount of impurities combined with the silanol-functional organosilicon compound, e.g. in the reaction product) and/or removing the silanol-functional organosilicon compound itself from the combination. Any suitable technique and/or protocol for isolation may be utilized. Examples of suitable isolation techniques include centrifugation, distillation, concentration/stripping/evaporation, washing and/or extraction, filtration, partitioning/phase separation (e.g. based on solubility, freeze point, etc.), chromatographic methods (e.g. column chromatography, size exclusion chromatography, ion exchange chromatography, affinity chromatography, hydrophobic interaction chromatography, reverse phase chromatography, etc.), and the like. As will be understood by those of skill in the art, any of these techniques may be used in combination (i.e., sequentially) with any other technique to isolate the silanol-functional organosilicon compound.

It is to be appreciated that isolating may include, and thus may be referred to as, purifying the silanol-functional organosilicon compound. However, purifying the silanol-functional organosilicon compound may comprise alternative and/or additional techniques as compared to those utilized in isolating the silanol-functional organosilicon compound. For example, in certain embodiments where the whole-cell catalyst or cell lysate is employed, general, isolating the silanol-functional organosilicon compound may comprise extracting the silanol-functional organosilicon compound from the reaction product or removing other components from reaction product (e.g. peptides, biological materials, fats, fibers, oils, carriers, solvents, etc.) to give a crude reaction product comprising the silanol-functional organosilicon compound, which is subsequently purified. Regardless of the particular technique(s) selected, isolation and/or purification of silanol-functional organosilicon compound may be performed in sequence (i.e., in line) with the reaction itself, and thus may be automated. In other instances, purification may be a stand-alone procedure to which the reaction product comprising the silanol-functional organosilicon compound is subjected.

In certain embodiments, as described above, the silanol-functional organosilicon compound prepared according to the method is provided as a component of a reaction product, or a purified/isolated form thereof. Such compositions may comprise one or more components in addition to the silanol-functional organosilicon compound. In some embodiments, such compositions are substantially free from, alternatively are free from, disiloxane byproducts of the oxidation reaction. Said differently, the reaction may be performed selectively with respect to the functional group transformation at the silicon atom of the silyl hydride group being oxidized to the silanol group during the method, such that the reaction is substantially free from subsequent condensation reaction of the silanol-functional organosilicon product once prepared. In this fashion, the reaction product prepared by the method may be substantially free from, alternatively is free from, a siloxane condensation product prepared from the silanol-functional organosilicon product.

It is to be appreciated that the method described herein is not limited to any particular application, but instead may be utilized in any application involving the oxidation of a suitable silyl hydride-containing organosilicon compound to the corresponding silanol-functional organosilicon compound. For example, in some embodiments, the method is utilized to prepare the silanol-functional compound as a final compound for a desired end use (e.g. as a stand-alone compound, or a component of a functional composition) or as a precursor for use in another reaction (e.g. a condensation or other such reaction for functionalizing and/or derivatizing silanol compounds). In other embodiments, the method may be utilized to oxidize silyl hydride-containing organosilicon compounds for purposes of biodegradation, e.g. to solubilizing and/or degrade such compounds.

The silanol-functional organosilicon compound prepared according to the method is also provided. In general, the silanol-functional organosilicon compound has the general formula $R_3Si$—OH, where each R is independently selected and defined above. In certain embodiments, the silanol-functional organosilicon compound corresponds to the following general formula:

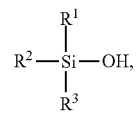

where each $R^1$, $R^2$, and $R^3$ are independently selected and defined above.

With regard to both preceding formulas, as will be appreciated by those of skill in the art in view of the description herein, the organosilicon compound utilized in the method forms the silyl moieties indicated by subformulas $R_3Si$— and $R^1R^2R^3Si$—. As such, the description above with regard to substituents R, $R^1$, $R^2$, and $R^3$ of the organosilicon compound applies equally to the silanol-functional organosilicon compound. For example, in some embodiments, the silanol-functional organosilicon compound corresponds to the general formula $R_3Si$—OH, where each R is an independently selected from hydrocarbyl groups, hydrocarbyloxy groups, and siloxy groups. In specific embodiments, the silanol-functional organosilicon compound corresponds to the general formula $R^1R^2R^3Si$—OH, where each $R^1$, $R^2$, and $R^3$ is independently selected from alkyl groups having from 1 to 6 carbon atoms, hydrocarbyloxy groups having from 1 to 12 carbon atoms, alkenyl groups having from 2 to 6 carbon atoms, and siloxy groups of formula $R^4_3SiO$—, where each $R^4$ is an independently selected hydrocarbyl group having from 1 to 6 carbon atoms.

In specific embodiments, the silanol-functional organosilicon compound is dimethyl(phenyl)silanol, ethyl(methyl)(phenyl)silanol, methyl(phenyl)(vinyl)silanol, benzyldimethylsilanol, dimethyl(p-tolyl)silanol, dimethyl(thiophen-2-yl)silanol, triethylsilanol, butyldimethylsilanol, methyldiphenylsilanol, and pentamethyldisiloxanol. One of skill in the art will appreciate the range of silanol-functional organosilicon compounds that may be prepared according to the method in view of the examples herein.

The following examples, illustrating embodiments of this disclosure, are intended to illustrate and not to limit the invention. Unless otherwise noted, all reactions are carried out under aerobic conditions. Reference to specific mutations in the exemplary cytochrome P450 variants are referred to using conventional residue identification/numbering, disregarding the initial methionine residue (i.e., M1) shown in the sequences of the Sequence Listing (i.e., SEQ ID NOS:1-4).

Materials

Unless otherwise noted, all other solvents, substrates, and reagents are purchased or otherwise obtained from various commercial suppliers (e.g. Sigma-Aldrich, VWR, Alfa Aesar) and utilized as received (i.e., without further purification).

Electrocompetent *Escherichia coli* (*E. coli*) cells are prepared following the protocol set forth in Sambrook et al., Transformation of E. coli by Electroporation, CSH Protoc. 2006 Jun. 1; 2006(1), the procedure of which is incorporated by reference herein.

Phusion polymerase and DpnI are purchased from New England Biolabs (NEB, Ipswich, MA).

Trace Metal Mix used in the protein expression protocols is the trace metal mix set forth in F. W. Studier, Protein production by auto-induction in high density shaking cultures, Protein Expr. Purif. 2005, 41, 207-234, the relevant composition of which is incorporated by reference herein.

Certain organosilicon compounds utilized in the Examples are set forth in Table 1 below.

TABLE 1

Organosilicon Compounds (1a)-(1j)

| Organosilicon Compound | Name/Description | Structure |
|---|---|---|
| 1a | Dimethylphenylsilane | 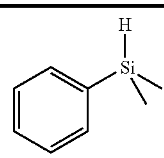 |
| 1b | Ethylmethylphenylsilane | 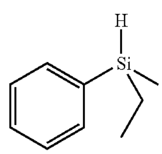 |
| 1c | Methylphenylvinylsilane | 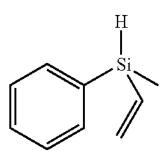 |
| 1d | Benzyldimethylsilane | 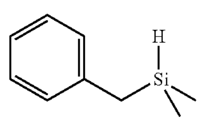 |
| 1e | Dimethyl(p-tolyl)silane | 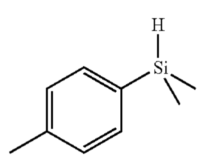 |
| 1f | Dimethyl(2-thienyl)silane | 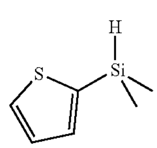 |
| 1g | Methyldiphenylsilane | 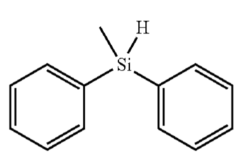 |
| 1h | Triethylsilane | 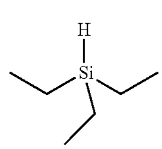 |
| 1i | Butyldimethylsilane | |
| 1j | Pentamethyldisiloxane | |

Organosilicon compounds 1a, 1d, and 1g-1j were purchased from commercial vendors, and organosilicon compounds 1b, 1c, and 1e-1f were prepared using literature procedures, including those set forth in M. Lee et al., Highly Selective and Practical Hydrolytic Oxidation of Organosilanes to Silanols Catalyzed by a Ruthenium Complex, J. Am. Chem. Soc. 2000, 122, 48, 12011-12012, and P. Volkova et al., Synthesis of difunctional 1,4-dimethyl-1,4-disilacyclohexanes, Russ. Chem. Bull. 1999, 48, 1712-1716, the relevant procedures of which are incorporated by reference herein. An exemplary synthesis of such organosilicon compounds is set forth in Preparation Example 1 below.

Preparation Example 1: Synthesis of Dimethyl(p-tolyl)silane

A round-bottom flask (100 mL) is charged with chlorodimethylsilane (1.11 mL, 10.0 mmol) in THF (6 mL) and cooled to 0° C. A solution of 4-methylphenylmagnesium bromide (24 mL, 0.5 M in THF) is added dropwise slowly over 15 min, and the resulting reaction mixture allowed to warm to room temperature and stirred for 8 hours. The reaction mixture is quenched with $NH_4Cl$ (5 mL, sat. aq.), extracted with $Et_2O$ (3×15 mL), and the combined organics washed with water (20 mL) and brine (20 mL) before being dried over $MgSO_4$. The organics are then filtered and concentrated under reduced pressure (200 torr) to give a crude product. The crude product is purified via silica column chromatography with a pentane mobile phase to give dimethyl(p-tolyl)silane (organosilicon compound 1e; 1.27 g, 8.44 mmol, 84%).

Equipment & Characterization

The following equipment and characterization procedures/parameters are used to evaluate various physical properties of the compounds and compositions prepared in the examples below.

Thin-Layer and Column Chromatography

Synthetic reactions are monitored using thin layer chromatography (TLC) (Merck 60 gel plates) using a UV-lamp for visualization.

Silica gel chromatography re performed using AMD Silica Gel 60, 230-400 mesh.

Nuclear Magnetic Resonance (NMR) Spectroscopy $^1H$ and $^{13}C$ NMR are recorded on a Bruker Prodigy 400 MHz instrument. Chemical shifts are reported in parts per million (ppm) downfield from tetramethylsilane and are referenced to the residual solvent resonance as the internal standard ($CHCl_3$: δ=7.26 ppm for $^1H$ NMR and $CDCl_3$: δ=77.16 ppm for $^{13}C$ NMR). Data are reported as follows: chemical shift, multiplicity (br s=broad singlet, s=singlet, d=doublet, t=triplet, q=quartet, m=multiplet, mc=centrosymmetric multiplet), coupling constant (Hz), integration.

Gas Chromatography (GC)

Gas chromatography data were collected on an Agilent 7820A GC system equipped with a flame ionization detector (GC-FID) using a DB-WAXetr column (30 m×0.32 mm, 0.25 μm film thickness) under the following conditions: Carrier Gas: helium; Column Flow: 2.5 mL/min; Split Ratio: 20:1; Injection Temperature: 250° C.; Detector Temperature: 300° C.

GC-FID Methods

Each GC-FID analysis was conducted according to one of the following temperature methods (A)-(E):

GC-FID Method A:

| Phase | Rate (° C./min) | Temperature (° C.) | Hold time (min) |
|---|---|---|---|
| Initial | — | 110 | 1 |
| Ramp 1 | 20 | 120 | 0 |
| Ramp 2 | 70 | 260 | 2 |

GC-FID Method B:

| Phase | Rate (° C./min) | Temperature (° C.) | Hold time (min) |
|---|---|---|---|
| Initial | — | 110 | 2 |
| Ramp 1 | 12 | 140 | 0 |
| Ramp 2 | 40 | 260 | 1 |

GC-FID Method C:

| Phase | Rate (° C./min) | Temperature (° C.) | Hold time (min) |
|---|---|---|---|
| Initial | — | 110 | 2 |
| Ramp 1 | 15 | 140 | 0 |
| Ramp 2 | 40 | 200 | 0 |

GC-FID Method D:

| Phase | Rate (° C./min) | Temperature (° C.) | Hold time (min) |
|---|---|---|---|
| Initial | — | 50 | 1 |
| Ramp 1 | 20 | 60 | 0 |
| Ramp 2 | 70 | 260 | 0.7 |

GC-FID Method E:

| Phase | Rate (° C./min) | Temperature (° C.) | Hold time (min) |
|---|---|---|---|
| Initial | — | 140 | 1 |
| Ramp 1 | 70 | 260 | 2.3 |

Sample Standards

Certain silanol-functional organosilicon compounds utilized as standards in the characterization procedures are obtained or prepared according to the procedures of one of Preparation Examples 2-3 below. Once obtained or prepared, each standard is characterized via NMR and GC according to the procedures set forth above, the results of which are listed in Table 2 further below.

Preparation Example 2: Synthesis of Silanol-Functional Organosilicon Compound with Pd/C A silyl-hydride functional organosilicon compound (1-5 mmol, 1.0 equiv.) is added dropwise to a suspension of Pd/C (10 wt. %, 0.1-0.4 mol %) and $H_2O$ (3 equiv) in ethyl acetate (0.8-1 M). The resulting suspension is stirred at room temperature until $H_2$ evolution ceases (0.5-4 h) and then filtered over neutral $Al_2O_3$ with ethyl acetate to remove particulates. The resulting solution is then stripped of solvent under reduced pressure, and purified via column chromatography on silica gel (eluent: hexanes/ethyl acetate) if necessary, to give a silanol-functional organosilicon compound, which is characterized via NMR and GC-FID according to the procedures set forth above.

Preparation Example 3: Synthesis of Silanol-Functional Organosilicon Compound with Ruthenium Catalyst A silyl-hydride functional organosilicon compound (0.37 mmol, 1.0 equiv.) is added dropwise to a suspension of solution of $[Ru(p-cymene)_2Cl_2]$ (0.88 mol %) and $H_2O$ (12 equiv.) in MeCN (0.5 M). The resulting mixture is stirred at room temperature until $H_2$ evolution ceases (0.5-4 h), stripped of solvent, and then filtered over neutral $Al_2O_3$ with hexanes to remove particulates. The resulting solution is then stripped of solvent under reduced pressure to give a silanol-functional organosilicon compound, which is characterized via NMR and GC-FID according to the procedures set forth above.

TABLE 2

Silanol-functional Organosilicon Compound Standards (2a)-(2l)

| Silanol-functional Organosilicon Compound | Structure | Name/Description |
|---|---|---|
| 2a | (dimethylphenylsilanol structure) | Dimethylphenylsilanol, obtained from commercial supplier. $^1$H NMR: δ = 0.41 (s, 6H), 2.05 (br s, 1H), 7.37-7.43 (m, 3H), 7.59-7.62 (m, 2H); $^{13}$C NMR: δ = 0.0, 128.0, 133.2, 139.2 ppm; GC (Method A): $t_R$ = 3.02 min. |

TABLE 2-continued

Silanol-functional Organosilicon Compound Standards (2a)-(2l)

| Silanol-functional Organosilicon Compound | Structure | Name/Description |
|---|---|---|
| 2b | (structure: phenyl-Si(OH)(Me)(Et)) | Ethylmethylphenylsilanol; prepared from organosilicon compound 1b according to Preparation Example 2 (clear liquid; 170 mg, 1.0 mmol, quant.). $^1$H NMR: δ = 0.39 (s, 1H), 0.83-0.88 (m, 2H), 0.99-1.03 (m, 3H), 1.81 (br s, 1H), 7.36-7.41 (m, 3H), 7.58-7.60 (m, 2H) ppm; $^{13}$C NMR: δ = −2.1, 6.8, 8.3, 128.0, 129.8, 133.4, 138.3 ppm; GC (Method B): $t_R$ = 6.76 min. |
| 2c | (structure: phenyl-Si(OH)(Me)(vinyl)) | Methylphenylvinylsilanol, prepared from organosilicon compound 1c according to Preparation Example 3 (clear liquid; 55 mg, 4.3 mmol, 90%). $^1$H NMR: δ = 0.48 (s, 3H), 1.83 (br s, 1H), 5.89 (dd, J = 20.3, 3.9 Hz, 1H), 6.14 (dd, J = 14.8, 3.9 Hz, 1H), 6.31 (dd, J = 20.3, 14.8 Hz, 1H), 7.36-7.44 (m, 3H), 7.60-7.62 (m, 2H) ppm. $^{13}$C NMR: δ = −1.56, 128.1, 130.0, 133.7, 134.8, 136.6, 137.3 ppm. GC (Method B): $t_R$ = 7.10 min. |
| 2d | (structure: benzyl-Si(OH)(Me)$_2$) | Benzyldimethylsilanol, prepared from organosilicon compound 1d according to Preparation Example 2 (clear liquid; 65 mg, 0.39 mmol, 39%). $^1$H NMR: δ = 0.14 (s, 6H), 1.60 (br s, 1H), 2.18 (s, 2H), 7.06 ($m_c$, 2H), 7.10 ($m_c$, 1H), 7.24 ($m_c$, 1H) ppm. $^{13}$C NMR: δ = −0.6, 28.2, 124.4, 128.3, 128.6, 139.1 ppm. GC (Method B): $t_R$ = 6.61 min. |
| 2e | (structure: p-tolyl-Si(OH)(Me)$_2$) | Dimethyl(p-tolyl)silanol, prepared from organosilicon compound 1e according to Preparation Example 2 (clear liquid; 100 mg, 0.67 mmol, 67% yield). $^1$H NMR: δ = 0.40 (s, 6H), 1.80 (br s, 1H), 2.37 (s, 3H), 7.22 ($m_c$, 2H), 7.50 ($m_c$, 2H) ppm. $^{13}$C NMR: δ = 0.2, 21.6, 128.9, 133.3, 135.7, 139.8 ppm. GC (Method B): $t_R$ = 6.75 min. |
| 2f | (structure: 2-thienyl-Si(OH)(Me)$_2$) | Dimethyl(2-thienyl) silanol, prepared from organosilicon compound 1f according to Preparation Example 2 (clear liquid; 150 mg, 0.92 mmol, 92%). $^1$H NMR: δ = 0.47 (s, 6H), 2.05 (br s, 1H), 7.22 (dd, J = 4.7, 3.3 Hz, 1H), 7.37 (dd, J = 3.3, 0.8 Hz, 1H), 7.64 (dd, 4.7, 0.8 Hz, 1H) ppm. $^{13}$C NMR: δ = 1.1, 128.4, 131.3, 134.8, 138.7 ppm. GC (Method B): $t_R$ = 6.77 min. |
| 2g | (structure: diphenyl-Si(OH)(Me)) | Methyldiphenylsilanol, prepared from organosilicon compound 1g according to Preparation Example 2 (clear liquid; 0.92 g, 4.3 mmol, quant.). $^1$H NMR: δ = 0.68 (s, 3H), 2.34 (br s, 1H), 7.36-7.45 (m, 6H), 7.62 ($m_c$, 4H) ppm. $^{13}$C NMR: δ = −1.1, 128.1, 130.0, 134.1, 137.2 ppm. GC (Method E): $t_R$ = 3.99 min. |
| 2h | (structure: Et$_3$Si-OH) | Triethylsilanol, prepared from organosilicon compound 1h according to Preparation Example 2 (clear liquid; 0.53 g, 4.0 mmol, 93%). $^1$H NMR: δ = 0.55-0.62 (m, 6H), 0.94-0.99 (m, 9H), 1.88 (br s, 1H) ppm. $^{13}$C NMR: δ = 5.9, 6.7 ppm. GC (Method C): $t_R$ = 2.56 min. |
| 2i | (structure: butyl-Si(OH)(Me)$_2$) | Butyldimethylsilanol, prepared from organosilicon compound 1i according to Preparation Example 2 (clear liquid; 0.47 g, 0.36 mmol, 83%). $^1$H NMR: δ = 0.11 (s, 6H), 0.57-0.61 (m, 2H), 0.88 ($m_c$, 3H), 1.29-1.37 (m, 4H), 1.94 (br s, 1H) ppm. $^{13}$C NMR: δ = −0.2, 13.9, 17.6, 25.5, 26.5 ppm. GC (Method C): $t_R$ = 2.33 min. |

TABLE 2-continued

Silanol-functional Organosilicon Compound Standards (2a)-(2l)

| Silanol-functional Organosilicon Compound | Structure | Name/Description |
|---|---|---|
| 2j | 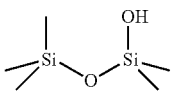 | Pentamethyldisiloxanol, prepared from organosilicon compound 1j according to Preparation Example 2 (clear liquid; 0.17 g, 4.3 mmol, quant.). $^1$H NMR: δ = 0.11 (s, 9H), 0.12 (s, 6H), 1.97 (br s, 1H) ppm. $^{13}$C NMR: δ = 0.6, 1.9 ppm. GC (Method D): $t_R$ = 2.37 min. |

GC Calibration Curves

For each sample to be analyzed via GC-FID, a dilution series of a corresponding standard is prepared according to one of the following procedures, and analyzed via GC-FID using one of temperature methods (A)-(E) methods above.

GC-FID Dilution Series Procedure 1 (DP-1): A series of solutions are prepared using an authenticated standard (800 mM-1.56 mM in MeCN). An aliquot (10 μL) of each solution is added to potassium phosphate buffer (390 μL, 0.1 M, pH=8) to achieve final concentrations of 20 mM-78.1 μM, followed by the addition of cyclohexane (900 μL) and acetophenone (20 μL of a 40 mM solution in cyclohexane) as an internal standard. The mixtures are vortexed for a few seconds and then centrifuged at 15° C. and 14,000 rpm for 10 min. An aliquot (200 μL) of supernatant is then transferred to a 2 mL glass GC screw top vial with a glass insert.

GC-FID Dilution Series Procedure 2 (DP-2): A 2 mM solution is prepared using an authenticated standard and potassium phosphate buffer (2 mL, 0.1 M, pH 8). From this solution, a dilution series is prepared to give 1 mL samples with final concentrations of 1 mM, 0.5 mM, 0.25 mM, 125 μM, 62.5 μM, and 31.25 μM. Et$_2$O (500 μL) is added to each sample, and the resulting mixture vortexed for a few second and then centrifuged at 4° C. and 14,000 g for 10 min. An aliquot (200 μL) of supernatant of each sample is then transferred to a 2 mL glass GC screw top vial with a glass insert, and charged with acetophenone (20 μL of a 40 mM solution in cyclohexane) as an internal standard.

Each series is prepared and analyzed in triplicate, and the resulting GC-data utilized to generate a calibration curve for each standard by plotting the ratio of product area to internal standard area on the GC (y-axis) against product concentration in mM (x-axis). The particular dilution series procedure and GC temperature method used to generate the calibration curve for each standard is set forth Table 3 below, with the results of the GC analyses and calibration curves shown in FIGS. 1-10.

TABLE 3

Calibration Curves for Silanol-functional Organosilicon Compound Standards

Figure 4:
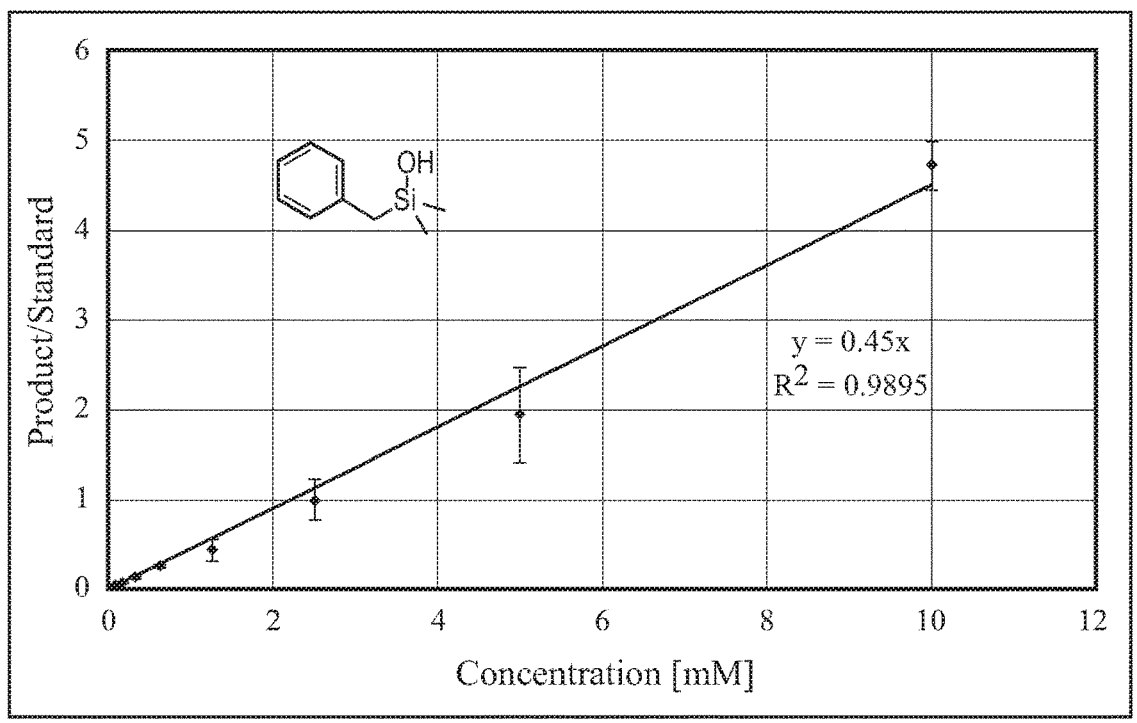
Figure 7:
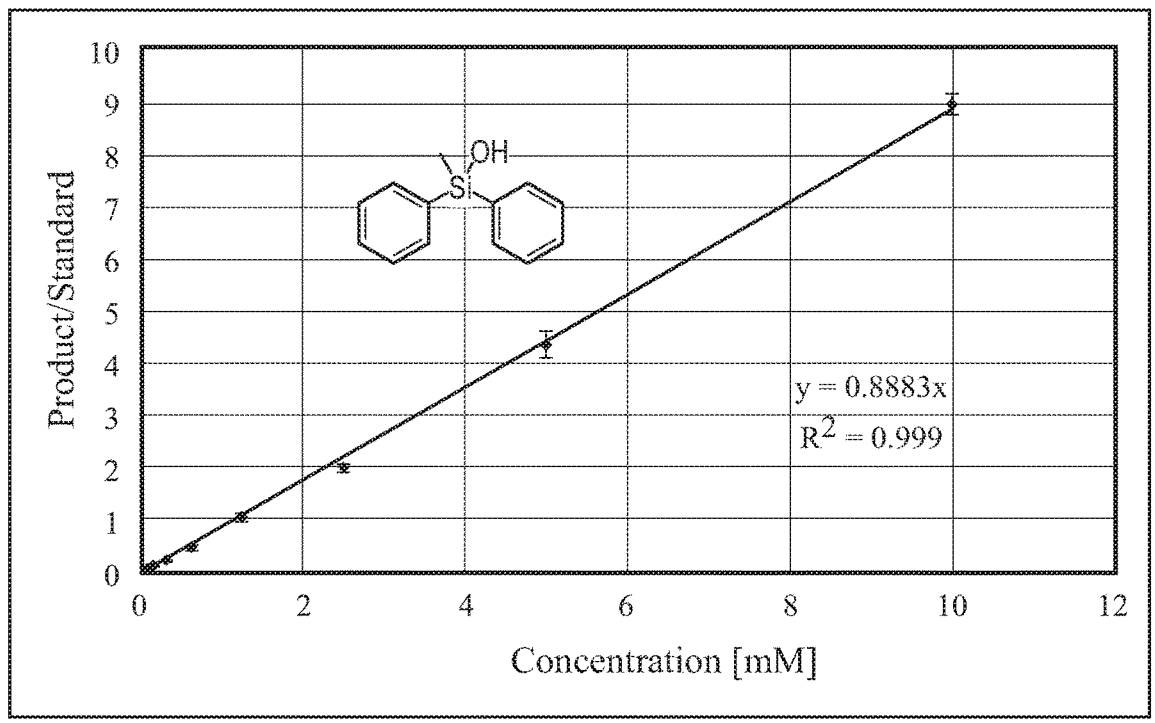
Figure 8:
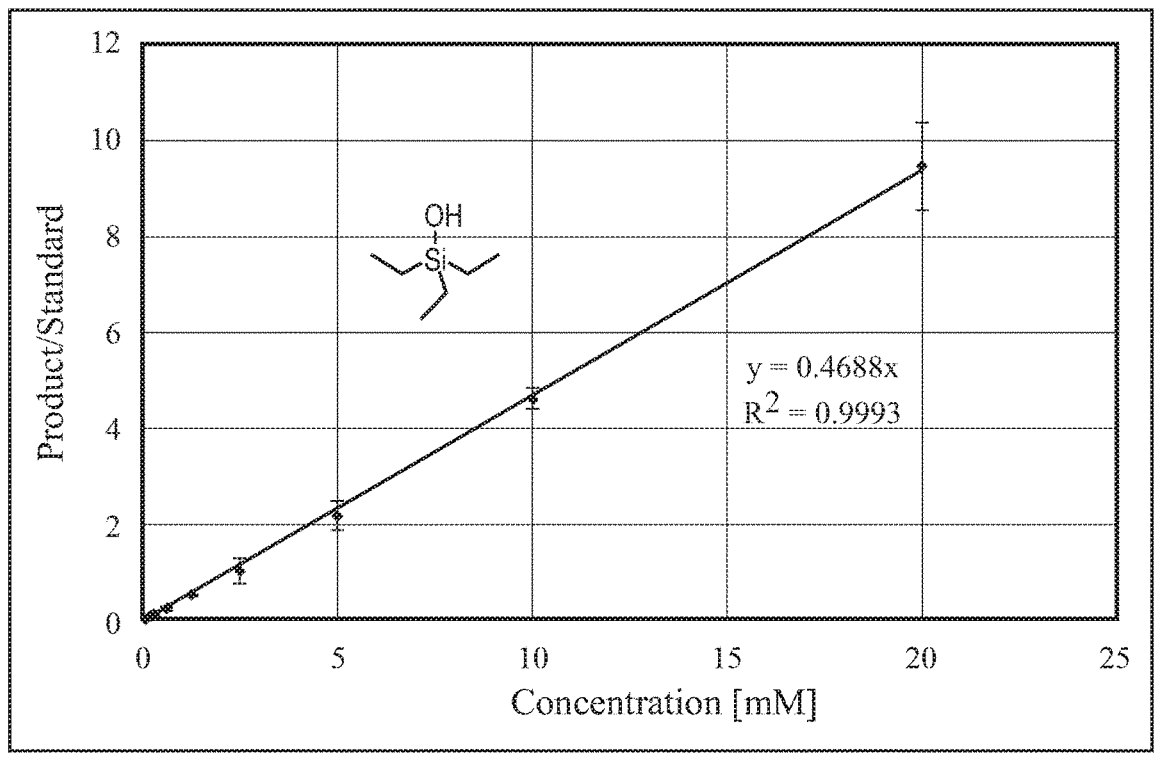
Figure 11A:
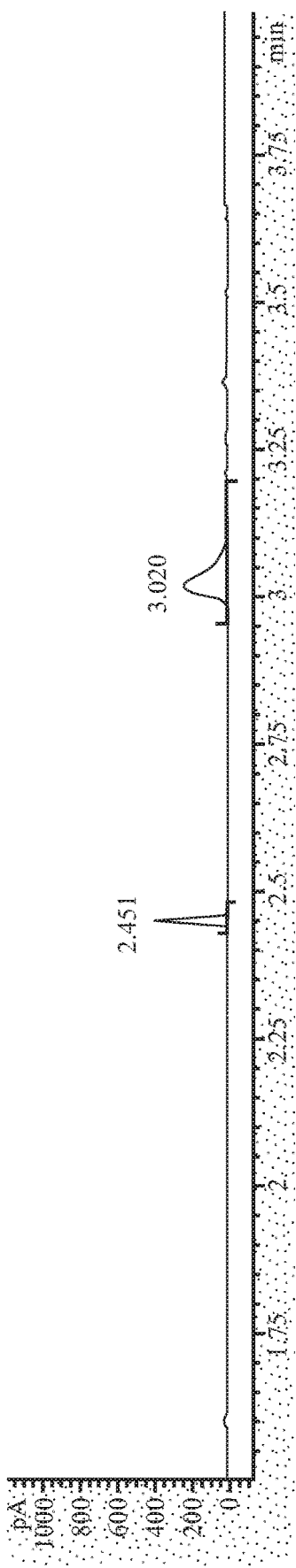
FIGS. 11-21 each include a pair of GC traces obtained from a silanol-functional organosilicon compound standard (FIGS. 11a-21a) and a silanol-functional organosilicon compound prepared according to the inventive method (FIGS. 11b-21b).
Figure 11B:
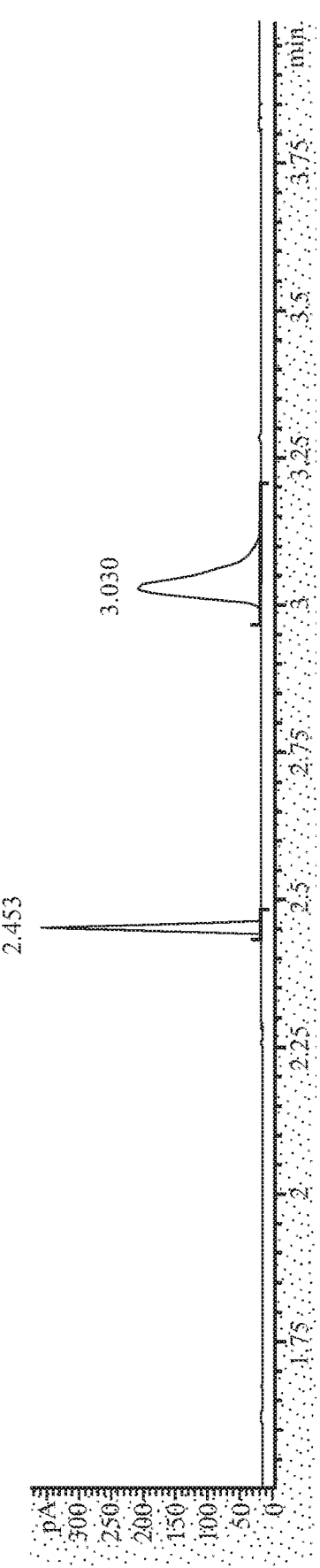

| Standard | Dilution Procedure | GC Method | Curve |
|---|---|---|---|
| 2a | DP-1 | A | FIG. 1 |
| 2b | DP-1 | B | FIG. 2 |
| 2c | DP-1 | B | FIG. 3 |
| 2d | DP-1 | B | FIG. 4 |
| 2e | DP-1 | B | FIG. 5 |
| 2f | DP-1 | B | FIG. 6 |
| 2g | DP-1 | E | FIG. 7 |
| 2h | DP-1 | C | FIG. 8 |
| 2i | DP-1 | C | FIG. 9 |
| 2j | DP-2 | D | FIG. 10 |

Site-Saturation Library Generation

Cytochrome P450 BM3 (CYP102A1, *Bacillus megaterium*) was selected as a scaffold for directed evolution, including sequential rounds of saturation mutagenesis at selected amino acid residues, to increase the enzyme's activity for silane oxidation. More specifically, libraries of mutant/variant P450 proteins were prepared and screened according to the procedures below to identify beneficial mutations.

For each library, two separate PCRs were performed, each using vector-specific primers at the 5' and 3' end of the sequence (005 and 006, Table 4) and one of the mutagenic primers set forth below. Afterwards, the remaining template was digested with DpnI. The two resulting overlapping fragments that contained the base-pair substitutions were then assembled in a second PCR using flanking primers 005 and 006 resulting in the full-length mutated gene. The pET22(b)+ vector (Novagen) was amplified using flanking primers (007 and 008, Table 4) in a long-range PCR. The PCR conditions were as follows (final concentrations): Phusion HF buffer 1×, 0.2 mM dNTPs each, 0.5 μM forward primer, 0.5 μM reverse primer, and 0.02 U/μl Phusion polymerase. The purified gene and the pET22(b)+ vector were then assembled using the Gibson assembly protocol set forth in D. G. Gibson et al., Enzymatic Assembly of DNA Molecules up to Several Hundred Kilobases, Nat. Methods 2009, 6, 343-45, the relevant procedure of which is incorporated by reference herein. The assembly product was used to transform electrocompetent E. cloni EXPRESS BL21 (DE3) Cells (Lucigen, Middleton, WI) with a Gene Pulser Xcell (Bio-Rad, Hercules, CA). SOC medium (0.75 mL) was added to electroporated cells, which were then incubated for 45 min at 37° C. and 220 rpm before being plated on Luria-Bertani (LB) agar plates (100 μg/mL ampicillin). Gel purification was performed with a Zymoclean Gel DNA Recovery Kit (Zymo Research Corp, Irvine, CA). Plasmids were isolated with a QIAprep Spin Miniprep Kit (Qiagen, Hilden, Germany). Generated sequences were sequenced by Laragen using primers T7 and 006 (Table 4).

TABLE 4

Primers for Site-Saturation Library Generation

| Primer | SEQ ID NO: | Sequence |
|---|---|---|
| 005 | 9 | AACTTTAAGAAGGAGATATACATATGACAATTAAAGAAATGCCTCAGCCA |
| 006 | 10 | CAGTGCTAGGTGAAGGAATACCGCCAAGCGGAA |
| 007 | 11 | TGGCTGAGGCATTTCTTTAATTGTCATATGTATATCTCCTTCTTAAAGTT |
| 008 | 12 | TTCCGCTTGGCGGTATTCCTTCACCTAGCACTG |
| T7 | 13 | TAATACGACTCACTATAGGG |

F87 was selected as a first target for directed evolution due to the close proximity of the residue to the heme cofactor. Site-saturation mutagenesis for amino acid residue 87 was performed using mutagenic primers bearing degenerate codon NNK, as set forth in Table 5.

TABLE 5

Primers for 87 Single Site-Saturation Library Generation

| Primer | SEQ ID NO: | Sequence |
|---|---|---|
| 87NNK_for | 14 | TGCAGGAGACGGGTTANNKACAAGCTGGACGCATG |
| 87NNK_rev | 15 | CATGCGTCCAGCTTGTMNNTAACCCGTCTCCTGCA |

The single-site-saturation mutagenesis library was screened in whole E. coli cells according to the procedures below, resulting in the identification of improved variant P450$_{SiOx1}$ containing mutation F87G.

Residues T327 and A328 were selected as further targets based on the close proximity of each residue to the iron cofactor in the distal heme-binding pocket. A double site-saturation mutagenesis strategy for this residue pair was selected to discover potential epistatic interactions between the two sites. Double site-saturation of sites T327 and A328 was performed using mutagenic primers bearing degenerate codons NDT, VHG, and TGG per the 22 codon trick, as set forth in Table 6.

TABLE 6

Primers for 327/328 Double-Site Saturation Library Generation.

| Primer | SEQ ID NO: | Sequence |
|---|---|---|
| 327NDT_328NDT_for | 16 | GCTTATGGCCANDTNDTCCTGCGTTTTCC |
| 327NDT_328NDT_rev | 17 | GGAAAACGCAGGAHNAHNTGGCCATAAGC |
| 327VHG_328VHG_for | 18 | GCTTATGGCCAVHGVHGCCTGCGTTTTCC |
| 327VHG_328VHG_rev | 19 | GGAAAACGCAGGCDBCDBTGGCCATAAGC |
| 327NDT_328VHG_for | 20 | GCTTATGGCCANDTVHGCCTGCGTTTTCC |
| 327NDT_328VHG_rev | 21 | GGAAAACGCAGGCDBAHNTGGCCATAAGC |
| 327VHG_328NDT_for | 22 | GCTTATGGCCAVHGNDTCCTGCGTTTTCC |
| 327VHG_328NDT_rev | 23 | GGAAAACGCAGGAHNCDBTGGCCATAAGC |
| 327NDT_328TGG_for | 24 | GCTTATGGCCANDTTGGCCTGCGTTTTCC |
| 327NDT_328TGG_rev | 25 | GGAAAACGCAGGCCAAHNTGGCCATAAGC |
| 327TGG_328NDT_for | 26 | GCTTATGGCCATGGNDTCCTGCGTTTTCC |
| 327TGG_328NDT_rev | 27 | GGAAAACGCAGGAHNCCATGGCCATAAGC |
| 327VHG_328TGG_for | 28 | GCTTATGGCCAVHGTGGCCTGCGTTTTCC |
| 327VHG_328TGG_rev | 29 | GGAAAACGCAGGCCACDBTGGCCATAAGC |
| 327TGG_328VHG_for | 30 | GCTTATGGCCATGGVHGCCTGCGTTTTCC |
| 327TGG_328VHG_rev | 31 | GGAAAACGCAGGCDBCCATGGCCATAAGC |
| 327TGG_328TGG_for | 32 | GCTTATGGCCATGGTGGCCTGCGTTTTCC |
| 327TGG_328TGG_rev | 33 | GGAAAACGCAGGCCACCATGGCCATAAGC |

The double site-saturation mutagenesis library prepared using the mutagenic primers above was screened in whole E. coli cells according to the procedures below, resulting in the identification of improved variant P450$_{SiOx2}$ containing mutations F87G and A328L.

Residues L181 and A184 were selected as additional targets, and a double site-saturation mutagenesis strategy for this residue pair was again selected to discover potential epistatic interactions between the two sites. Double site-saturation of sites L181 and A184 was also performed using mutagenic primers bearing degenerate codons NDT, VHG, and TGG per the 22 codon trick, as set forth in Table 7.

TABLE 7

Primers for 181/184 Double-Site Saturation Library Generation.

| Primer | SEQ ID NO: | Sequence |
|---|---|---|
| 181NDT_184NDT_for | 34 | GGTCCGTGCANDTGATGAANDTATGAACAAGC |
| 181NDT_184NDT_rev | 35 | GCTTGTTCATAHNTTCATCAHNTGCACGGACC |
| 181VHG_184VHG_for | 36 | GGTCCGTGCAVHGGATGAAVHGATGAACAAGC |
| 181VHG_184VHG_rev | 37 | GCTTGTTCATCDBTTCATCCDBTGCACGGACC |
| 181NDT_184VHG_for | 38 | GGTCCGTGCANDTGATGAAVHGATGAACAAGC |
| 181NDT_184VHG_rev | 39 | GCTTGTTCATCDBTTCATCAHNTGCACGGACC |
| 181VHG_184NDT_for | 40 | GGTCCGTGCAVHGGATGAANDTATGAACAAGC |
| 181VHG_184NDT_rev | 41 | GCTTGTTCATAHNTTCATCCDBTGCACGGACC |

TABLE 7-continued

Primers for 181/184 Double-Site Saturation Library Generation.

| Primer | SEQ ID NO: | Sequence |
|---|---|---|
| 181NDT_184TGG_for | 42 | GGTCCGTGCANDTGATGAATGGATGAACAAGC |
| 181NDT_184TGG_rev | 43 | GCTTGTTCATCCCATTCATCAHNTGCACGGACC |
| 181TGG_184NDT_for | 44 | GGTCCGTGCATGGGATGAANDTATGAACAAGC |
| 181TGG_184NDT_rev | 45 | GCTTGTTCATAHNTTCATCCCATGCACGGACC |
| 181VHG_184TGG_for | 46 | GGTCCGTGCAVHGGATGAATGGATGAACAAGC |
| 181VHG_184TGG_rev | 47 | GCTTGTTCATCCCATTCATCCDBTGCACGGACC |
| 181TGG_184VHG_for | 48 | GGTCCGTGCATGGGATGAAVHGATGAACAAGC |
| 181TGG_184VHG_rev | 49 | GCTTGTTCATCDBTTCATCCCATGCACGGACC |
| 181TGG_184TGG_for | 50 | GGTCCGTGCATGGGATGAATGGATGAACAAGC |
| 181TGG_184TGG_rev | 51 | GCTTGTTCATCCCATTCATCCCATGCACGGACC |

The double site-saturation mutagenesis library prepared using the mutagenic primers above was screened in whole *E. coli* cells according to the procedures below, resulting in the identification of improved variant P450$_{SiOx3}$ containing mutations F87G, A328L, L181D, and A184H.

Cytochrome P450 Variants

Various cytochrome P450 variants prepared according to the procedures above are set forth in Table 8 below.

TABLE 8

Cytochrome P450 Variants

| P450 Variant | Description/Mutation(s) | SEQ ID NO: |
|---|---|---|
| P450$_{BM3}$ WT | Wild type P450BM3 | 1 |
| P450$_{SiOx1}$ | F87G | 2 |
| P450$_{SiOx2}$ | F87G & A328L | 3 |
| P450$_{SiOx3}$ | F87G, A328L, L181D & A184H | 4 |

General Protein Expression Protocol 1

A large-scale (25-250 mL culture) protein expression protocol was used. Specifically, single colonies of *E. coli* BL21(DE3) cells transformed with the plasmid encoding the protein of interest were picked with sterile toothpicks and grown overnight in Luria-Bertani medium supplemented with ampicillin (100 μg/mL final concentration, LB$_{amp}$) at 37° C. and 220 rpm. The preculture was used to inoculate an expression culture (2% v/v preculture) in Terrific Broth supplemented with ampicillin (100 μg/mL final concentration, TB$_{amp}$) in an unbaffled 125 mL to 1 L Erlenmeyer flask. The expression culture was grown at 37° C. and 220 rpm for 3.5 hours and then cooled on ice for 30 min. Isopropyl β-d-glucopyranoside (IPTG, 0.5 mM final concentration), 5-aminolevulinic acid (Ala, 1.0 mM final concentration), FeCl$_3$ (3.5 μM final concentration), and Trace Metal Mix (1000×, 0.6 μL per 100 mL culture), and the proteins expressed at 22° C. and 180 rpm for 20-22 h. Following expression, the cultures were centrifuged at 10° C. and 4000 g for 10 min, and the resulting cell pellets resuspended in potassium phosphate buffer (0.1 M, pH 8.0, 5-25 mL).

General Protein Expression Protocol 2

A small-scale expression of P450s in 96-deep-well plates was used. Specifically, single colonies from *E. coli* BL21 (DE3) cells transformed with plasmids of P450 site-saturation mutagenesis libraries were picked from LB$_{amp}$ agar plates using sterile toothpicks and grown in 300$_4$ of LB$_{amp}$ in 2 mL 96-deep-well plates at 37° C. and 220 rpm (80% humidity) for 12-18 hours. The preculture (50 μL) was used to inoculate 0.6 mL of TB$_{amp}$ media in 2 mL 96-deep-well plates. The expression culture plate was incubated at 37° C. and 220 rpm (80% humidity) for 3.5 hours and then chilled on ice for 30 minutes. TB$_{amp}$ (50 μL) containing isopropyl β-d-glucopyranoside (IPTG, 0.5 mM final concentration), 5-aminolevulinic acid (Ala, 1.0 mM final concentration) as well as FeCl$_3$ (3.5 μM final concentration), and Trace Metal (1000×, 0.6 μL per 100 mL culture) were added, and the proteins expressed at 22° C. and 220 rpm for 20-24 h. Following expression, cells were pelleted via centrifugation at 10° C. and 4000 g for 10 min.

Cell Lysis Procedure

Cell lysates containing the expressed target enzymes were prepared and used for reactions and protein concentration determinations according to various procedures below. In particular, cells were lysed by sonication of 5-10 mL resuspended whole cells in potassium phosphate buffer (0.1 M, pH 8) on ice for 1.5 minutes at 30% amplitude (1 second on, 2 second off) using a QSonica Q500 Sonicator and a ⅛-inch tip. The sonicated cell mixture was clarified via centrifugation at 4° C. and 14000 rpm for 10 min.

Protein Concentration Determination: CO Binding Assay

A CO binding assay was performed with cell lysate to determine protein concentration. A sample of lysate (1 mL) and sodium dithionite (ca. 1 mg) were combined in a cuvette (1 cm). The absorbance was read at 450 nm and 490 nm. CO was bubbled through the lysate for ca. 1 min and absorbance read at 450 nm and 490 nm. Protein concentration was then determined according to Beer's law (l=1 cm, $\varepsilon_{450-490}$=0.091 cm$^{-1}$ μM$^{-1}$) using an average of three samples.

Cytochrome P450 Variants Catalysts

Various catalyst compositions comprising cytochrome P450 variants are prepared according to the procedures above. The particular cytochrome P450 variant and form of the catalyst composition are set forth in Table 9 below.

TABLE 9

Cytochrome P450 Variant Catalyst Compositions

| Catalyst | P450 Variant | Form |
|---|---|---|
| P450 CC1 | P450$_{BM3}$ WT | Whole cell |
| P450 CC2 | P450$_{BM3}$ WT | Lysate |
| P450 CC3 | P450$_{SiOx1}$ | Whole cell |
| P450 CC4 | P450$_{SiOx2}$ | Whole cell |
| P450 CC5 | P450$_{SiOx3}$ | Whole cell |
| P450 CC6 | P450$_{SiOx3}$ | Lysate |

Reaction Screening of Whole-Cell in 96-Well Plates

Cell pellets in 2 mL 96-well plates were resuspended in 390 μL potassium phosphate buffer (0.1 M, pH 8) by vortexing. Organosilicon Compound 1a (400 mM in MeCN, 10 μL, 10 mM final concentration) was added to each well. The plates were then immediately covered with a pierceable foil cover (USA Scientific) and shaken at room temperature and 60 rpm for 3-4 h. Afterwards, cyclohexane (900 µL) was added to each well, the plate was sealed with a silicon mat and vortexed for a few seconds. The phases were separated by centrifugation at 15° C. and 14000 rpm for 10 min. An aliquot (200 µL) of supernatant was transferred to a 2 mL glass GC screw top vial with a glass insert and analyzed via GC-FID according to the procedure of GC-FID Method A set forth above.

Reaction Procedure 1: Small-Scale Biocatalytic Reaction

Unless stated otherwise, small-scale reactions were set up aerobically on 400-µL-scale. In particular, suspensions of *E. coli* cells expressing the appropriate enzyme or the corresponding lysate were adjusted to the desired protein concentration with potassium phosphate buffer (0.1 M, pH 8) and 386 µL (for whole cell reactions) or 390 µL (for lysate reactions) of the mixture were placed in a 2 mL glass GC screw top vial. A glucose solution (1.0 M in potassium phosphate buffer, 4 µL, for whole cell reactions) or NADPH (3.9 mg, 10 mM final concentration, for lysate reactions) was added, followed by Organosilicon Compound 1a (400 mM in MeCN, 10 µL, 10 mM final concentration). The vials were then sealed with a cap and moved to a shaker. After shaking at the indicated temperature and 60 rpm for 4-48 h, cyclohexane (900 µL) and acetophenone (40 mM in cyclohexane, 20 µL) as internal standard were added. The mixture was vortexed for a few seconds, and the phases were separated by centrifugation at 15° C. and 14000 rpm for 10 min. An aliquot (200 µL) of the organic phase was transferred to a 2 mL glass GC screw top vial with a glass insert and analyzed via GC-FID according to the procedure of GC-FID Method A set forth above. All reactions were performed at least in triplicate (technical replicates).

Performance of P450$_{BM3}$ Variants

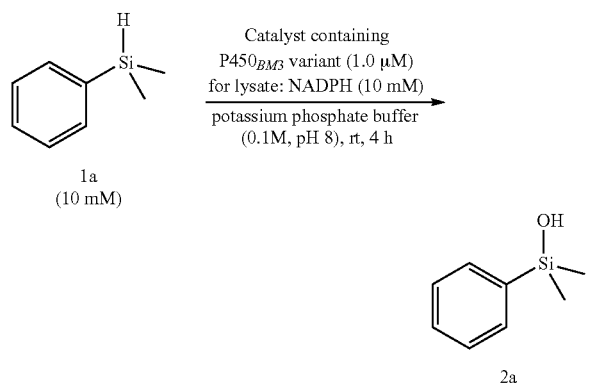

Small-scale biocatalytic reactions were performed with different P450$_{BM3}$ variants at 1.0 µM protein concentration for 4 h at room temperature according to the procedure set forth in Reaction Procedure 1 above to prepare Silanol-Functional Organosilicon Compound 2a. In particular, cells were resuspended in 310 µL potassium phosphate buffer (0.1 M, pH 8), 20 µL of a stock solution containing glucose oxidase (from *Aspergillus niger*, 1000 U/mL) and catalase (from Bovine liver, 14000 U/mL) in double-distilled water, and 60 µL of a glucose solution (250 mM in potassium phosphate buffer) were added. Particular components and parameters of these biocatalytic reactions are set forth in Table 10 below.

TABLE 10

Reactions Using P450$_{BM3}$ Variants

| Entry | Catalyst | Conditions | Yield (%) | TTN | Note |
|---|---|---|---|---|---|
| 1 | P450 CC1 | aerobic | 2.1 ± 0.3 | 210 ± 25 | a |
| 2 | P450 CC1 | anaerobic | 0.20 | n.a. | b |
| 3 | P450 CC1 | anaerobic | 0.20 | n.a. | b, c |
| 4 | P450 CC3 | whole cells | 3.1 ± 0.1 | 310 ± 10 | a |
| 5 | P450 CC4 | whole cells | 8.5 ± 1.3 | 850 ± 130 | a |
| 6 | P450 CC5 | whole cells | 12 ± 2.4 | 1200 ± 240 | a |
| 7 | P450 CC2 | lysate | 18 ± 1.4 | 1740 ± 140 | a |
| 8 | P450 CC6 | lysate | 36 ± 1.5 | 3620 ± 150 | a | n.a. = not applicable.
a: The average of biological duplicates and triplicate runs is given, with six runs in total
b: The reactions were set up anaerobically in a coy chamber.
c: An oxygen depletion system was used.
TTN: Total Turnover Number.

Optimization of Reaction Conditions

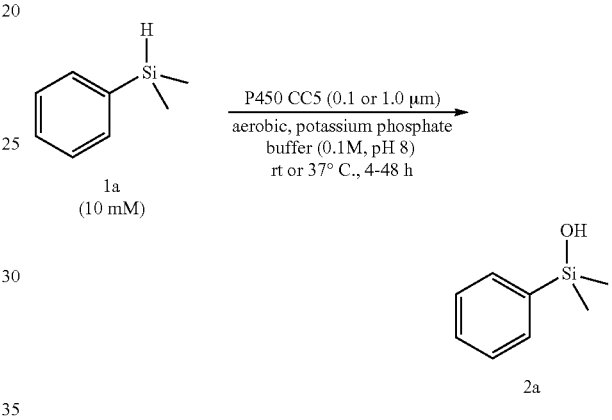

Small-scale biocatalytic reactions were performed according to the procedure set forth in Reaction Procedure 1 above to prepare Silanol-Functional Organosilicon Compound 2a, utilizing P450 CC5 and various reaction conditions. Particular components and parameters of these biocatalytic reactions are set forth in Table 11 below.

TABLE 11

Reactions Using P450$_{BM3}$ Variants Under Varied Conditions

| Entry | Temperature (° C.) | Protein Concentration (µM) | Time (h) | Yield (%) | TTN |
|---|---|---|---|---|---|
| 1$^a$ | rt | 1.0 | 4 | 12 ± 2.4 | 1200 ± 240 |
| 2 | 37 | 1.0 | 4 | 17.5 ± 3.1 | 1750 ± 310 |
| 3 | 37 | 1.0 | 48 | 24 ± 0.6 | 2400 ± 60 |
| 4 | rt | 0.1 | 4 | 1.6 ± 0.1 | 1560 ± 50 |
| 5 | rt | 0.1 | 24 | 2.0 ± 0.1 | 2020 ± 120 |
| 6 | rt | 0.1 | 48 | 3.1 ± 0.1 | 3110 ± 30 |
| 7 | 37 | 0.1 | 4 | 2.5 ± 0.1 | 2500 ± 10 |
| 8 | 37 | 0.1 | 24 | 9.9 ± 0.5 | 9870 ± 490 |
| 9 | 37 | 0.1 | 48 | 19 ± 0.2 | 19100 ± 190 | rt: room temperature
a: See Table 10, Entry 6.

In these examples, yields (of Silanol-Functional Organosilicon Compound 2a) and total turnover number (TTN) are given as an average of triplicate runs (technical replicates).

Reaction Procedure 2: Preparative Scale Biocatalytic Reaction

Single colonies of *E. coli* BL21(DE3) cells carrying a plasmid encoding P450$_{SiOx3}$ were picked with sterile toothpicks and grown overnight in 2×5 mL LB$_{amp}$ at 37° C. and 220 rpm. Each preculture was used to inoculate an expression culture in TB$_{amp}$ (250 mL). The expression cultures were grown at 37° C. and 180 rpm for 3.5 hours and then cooled on ice for 30 min. Isopropyl β-d-glucopyranoside (IPTG, 0.5 mM final concentration), 5-aminolevulinic acid (Ala, 1.0 mM final concentration) as well as FeCl$_3$ (3.5 μM final concentration) and Trace Metal Mix (1000×, 0.6 μL per 100 mL culture) were added, and the proteins were expressed at 22° C. and 180 rpm overnight. Following expression, the cultures were centrifuged at 10° C. and 4,000 g for 10 min. The cell pellets were then resuspended in potassium phosphate buffer (100 mM, pH 8.0, 25 mL per pellet), and the cell suspensions were combined. The protein concentration in the whole-cell suspension was determined to 8.8 μM by lysis of an aliquot, and the CO binding assay as described earlier. A solution of Organosilicon Compound 1a (400 mM in MeCN, 625 μL, 0.25 mmol) was added to the 50 mL of the cell suspension and the reaction mixture was shaken at 180 rpm for 3 d at 37° C. Afterwards, the mixture was extracted with cyclohexane (3×300 mL) and the solvent was removed under reduced pressure. Drying in vacuo delivered Silanol-Functional Organosilicon Compound 2a (dimethylphenylsilanol, 29 mg, 76%) as a clear liquid.

Substrate Scope: Small-Scale Biocatalytic Reactions with Various Organosilicon Compounds

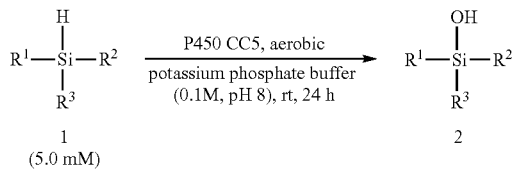

Small-scale biocatalytic reactions were performed according to the procedure set forth in Reaction Procedure 1 above to prepare various Silanol-Functional Organosilicon Compounds (2) utilizing P450 CC5.

In particular, each of Organosilicon Compounds 1a-1i were utilized to prepare Silanol-Functional Organosilicon Compounds 2a-2i, respectively, according to the following procedure: Pelleted E. coli cells expressing P450$_{SiOx3}$ from 25-50 mL cultures were resuspended in potassium phosphate buffer (5-10 mL, 0.1 M, pH 8), and 390 μL of the mixture were placed in a 2 mL glass GC screw top vial. The corresponding Organosilicon Compound (1) (200 mM in MeCN, 10 μL, 5.0 mM final concentration) was added, and the vial sealed with a cap. After shaking at room temperature and 60 rpm for 24 h, cyclohexane (9004) and acetophenone (40 mM in cyclohexane, 20 μL) as internal standard were added. The mixture was vortexed for a few seconds and the phases were separated by centrifugation at 15° C. and 14,000 rpm for 10 min. An aliquot (200 μL) of the organic phase was transferred to a 2 mL glass GC screw top vial with a glass insert.

Organosilicon Compound 1j was utilized to prepare Silanol-Functional Organosilicon Compound 2j according to the following procedure: Pelleted E. coli cells expressing P450$_{SiOx3}$ from 25-50 mL cultures were resuspended in potassium phosphate buffer (5-10 mL, 0.1 M, pH 8), and 1 mL of the mixture was placed in a 2 mL glass GC screw top vial. Organosilicon Compound 1j (pentamethyldisiloxane, 1.074, 5.0 mM final concentration) was added, and the vial sealed with a cap. After shaking at room temperature and 60 rpm for 24 h, diethyl ether (500 μL) was added. The mixture was vortexed for a few seconds, and the phases were separated by centrifugation at 15° C. and 14,000 rpm for 10 min. An aliquot (200 μL) of the organic phase was transferred to a 2 mL glass GC screw top vial with a glass insert.

A negative control was prepared using Organosilicon Compound 1j in potassium phosphate buffer (0.1 M, pH 8) without whole cells added, and otherwise identical reaction conditions to the catalyzed reaction of Organosilicon Compound 1j above.

All reactions were performed in triplicate (technical replicates), and analyzed via GC-FID according to the procedures set forth above. Particular components, parameters, and analysis methods utilized in these biocatalytic reactions are set forth in Table 12 below, with yields and TTN given as average of the technical replicates. The chromatograms obtained from the GC-FID analyses are shown in FIGS. 11-21, which each include a pair of GC traces from the standards (FIGS. 11a-21a, respectively) and entries 1-11 below (FIGS. 11b-21b, respectively).

TABLE 12

Reactions of P450$_{BM3}$ Variant with Varied Substrates

Figure 12A:
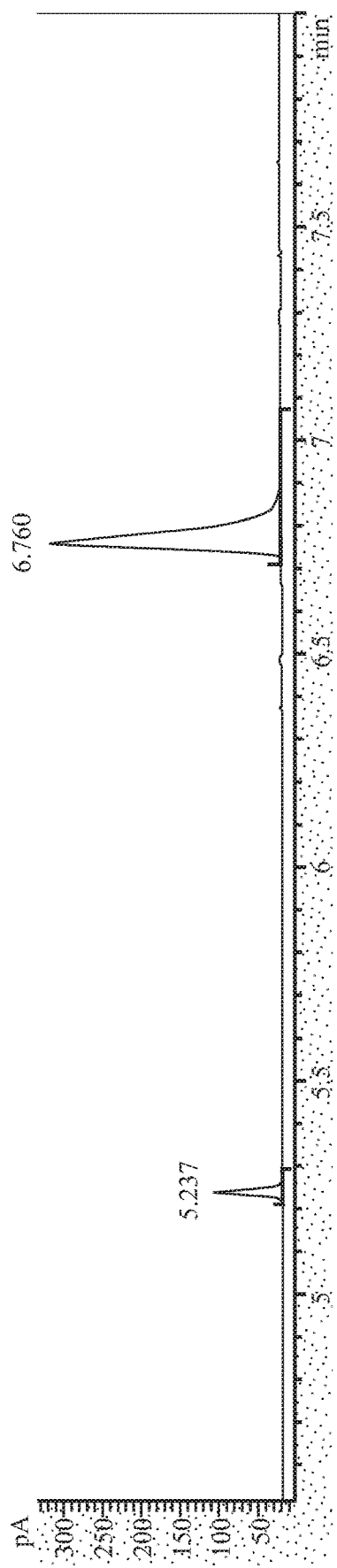
Figure 12B:
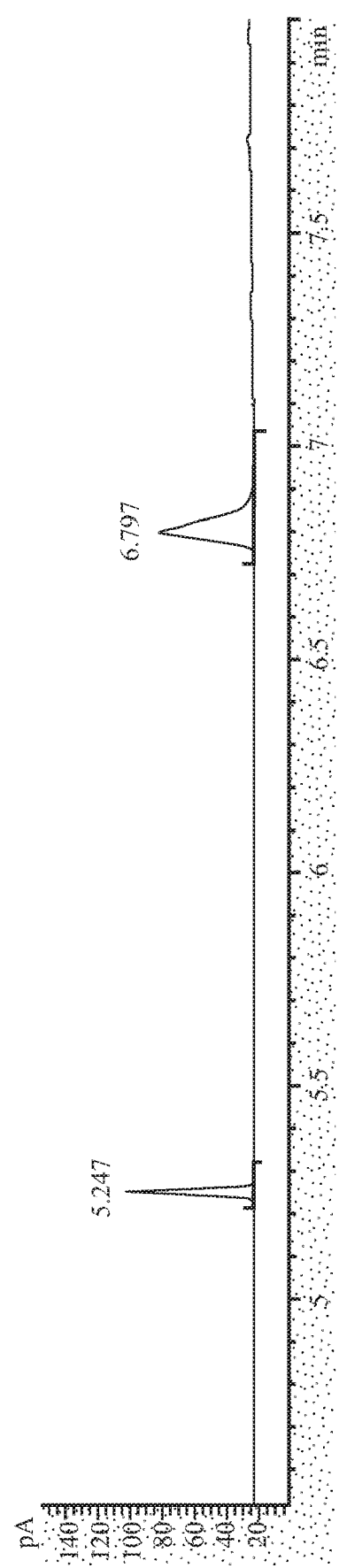
Figure 13A:
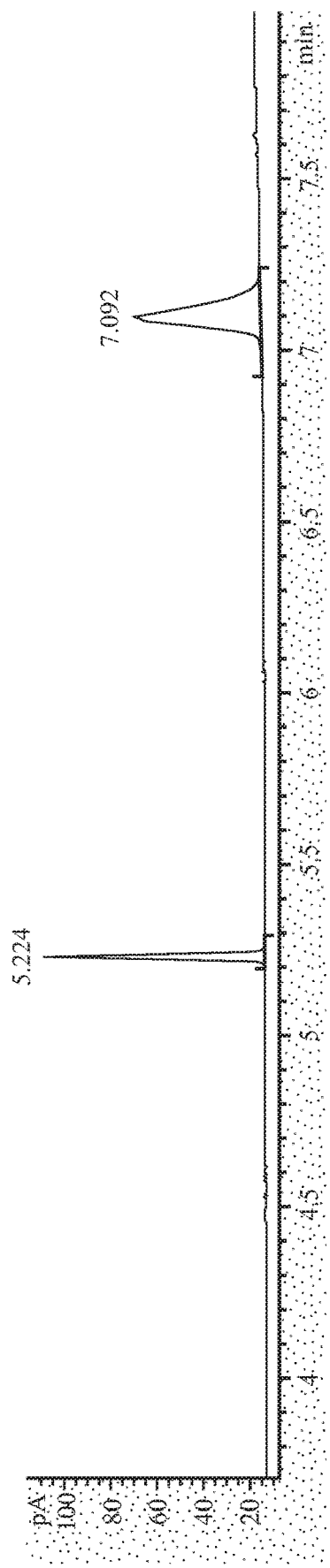
Figure 13B:
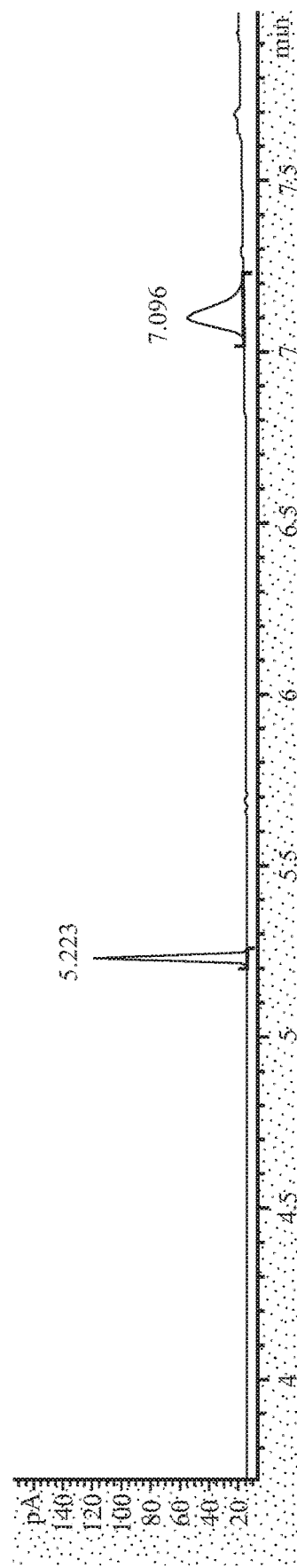
Figure 14A:
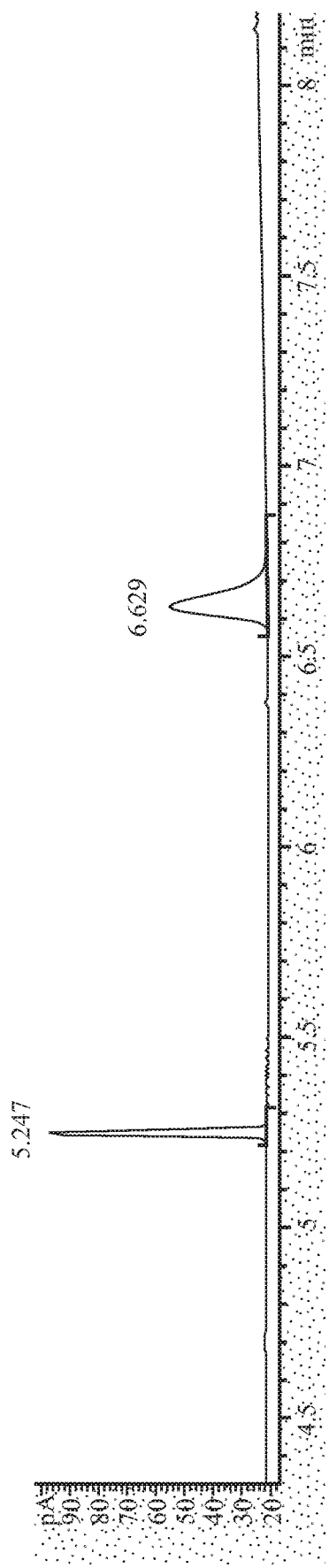
Figure 14B:
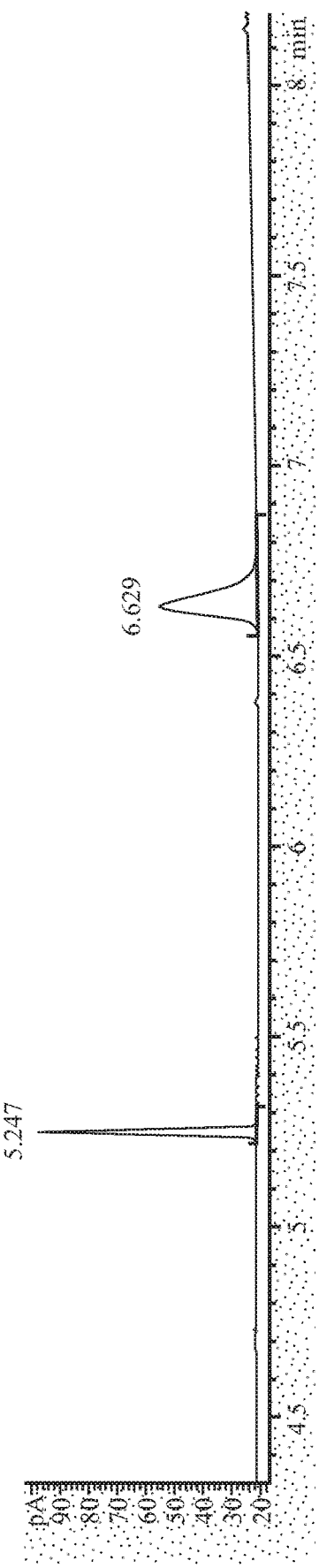
Figure 15A:
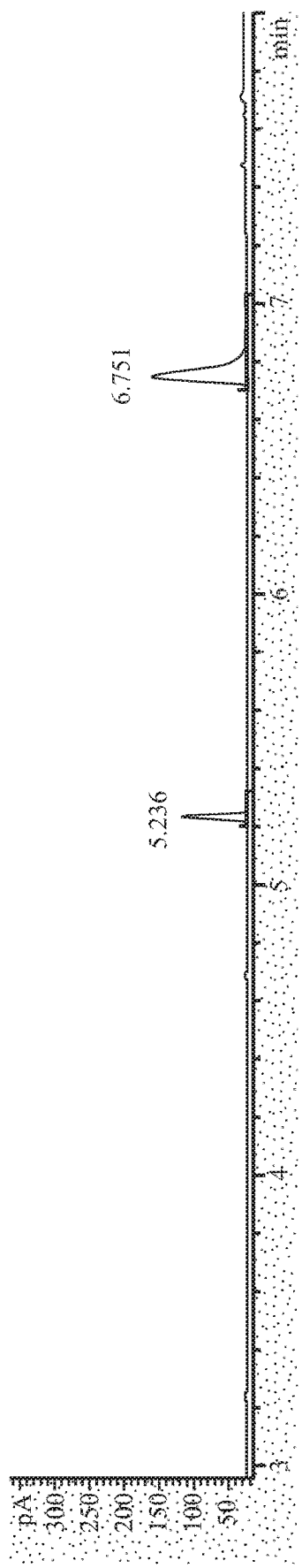
Figure 15B:
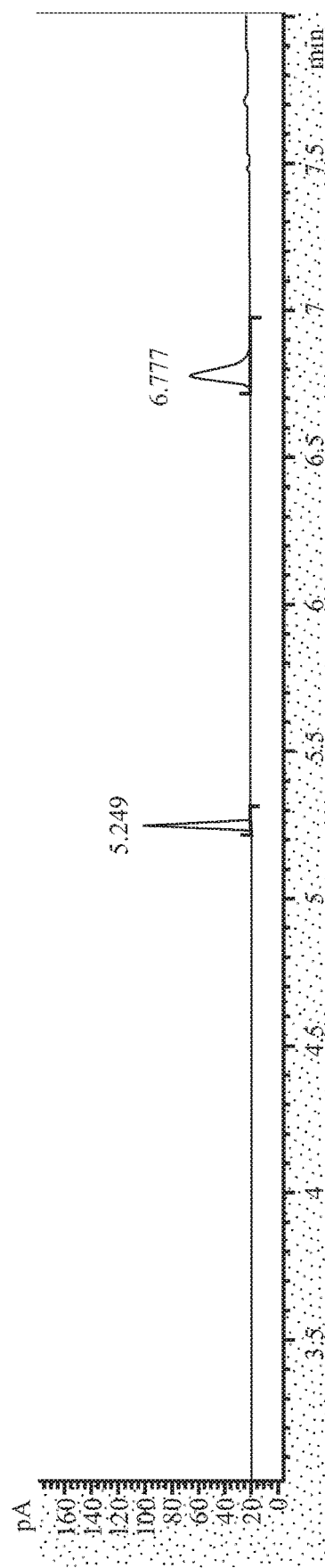
Figure 16A:
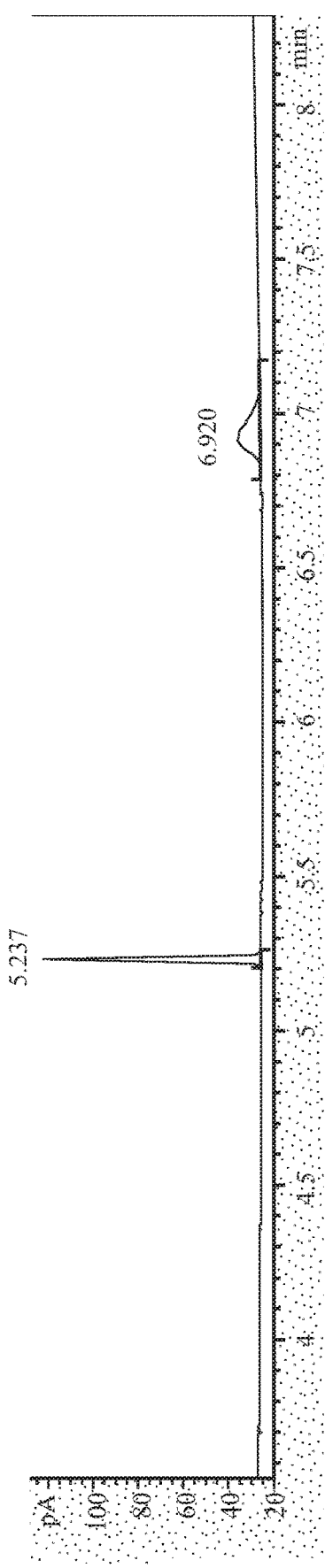
Figure 16B:
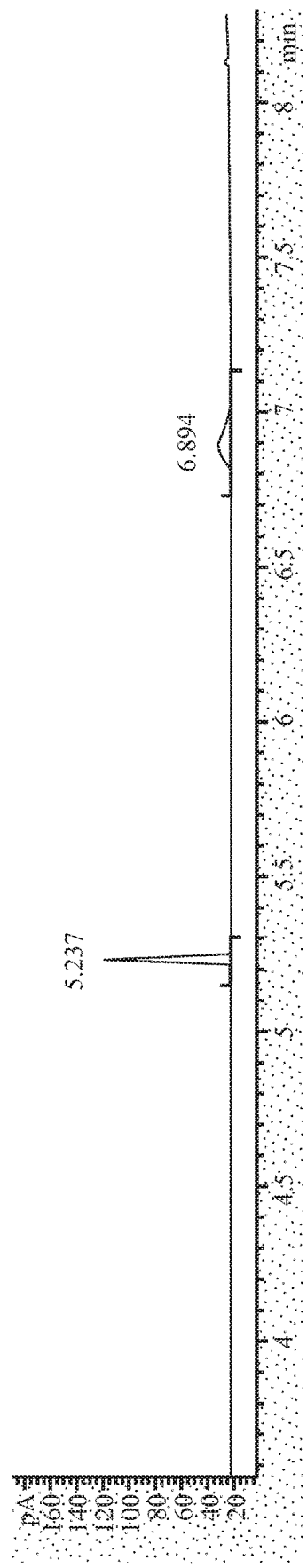
Figure 17A:
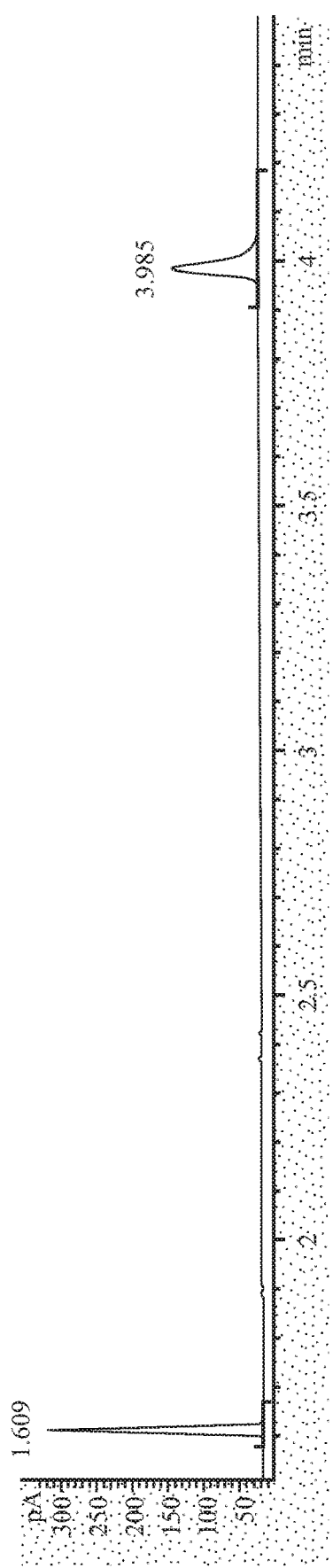
Figure 17B:
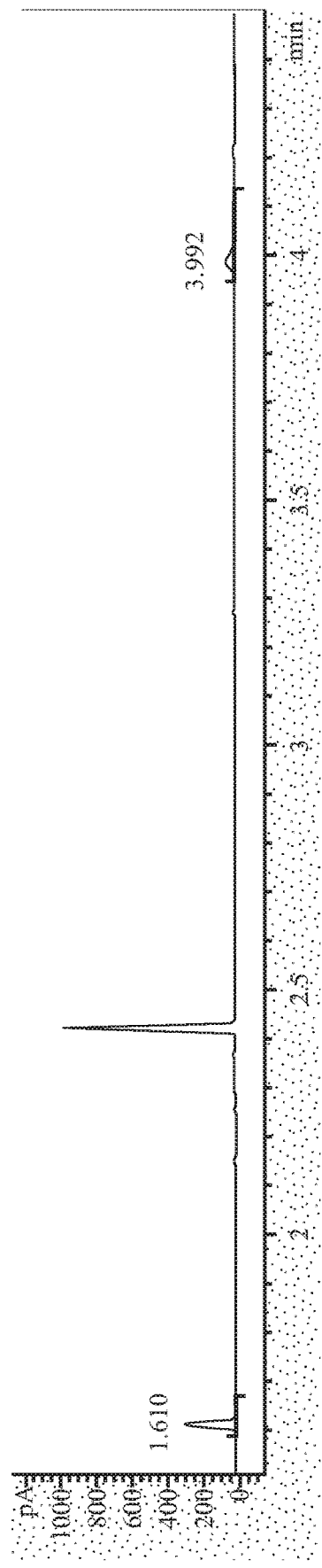
Figure 18A:
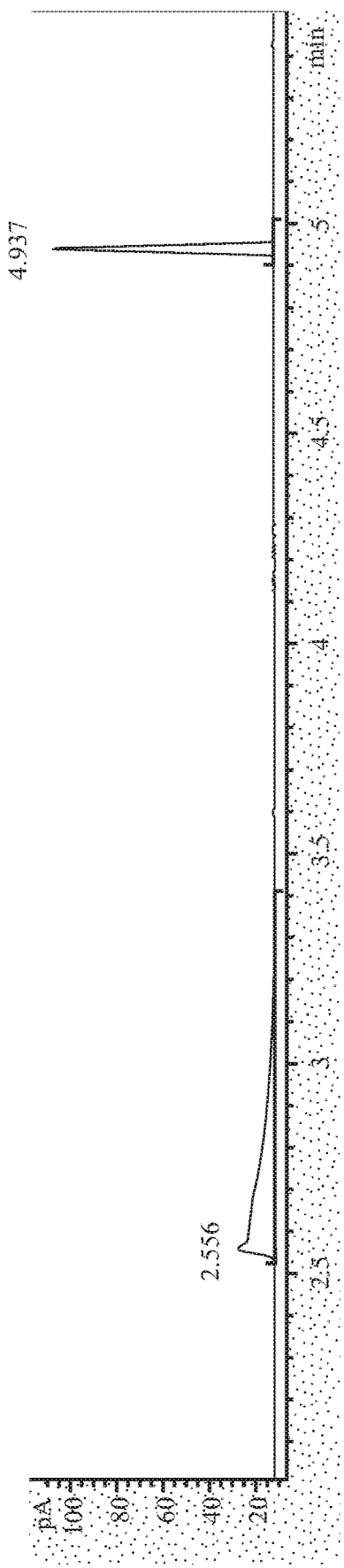
Figure 18B:
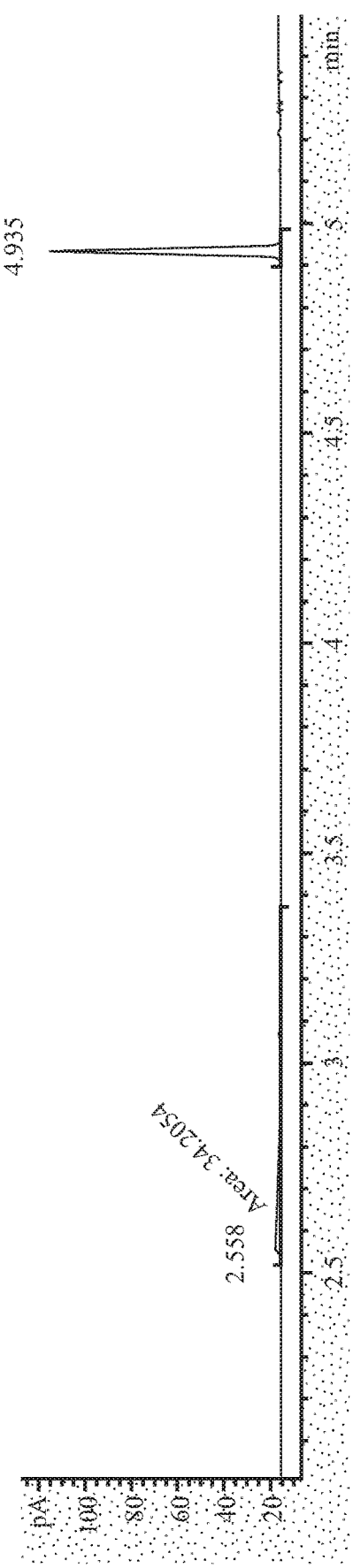
Figure 19A:
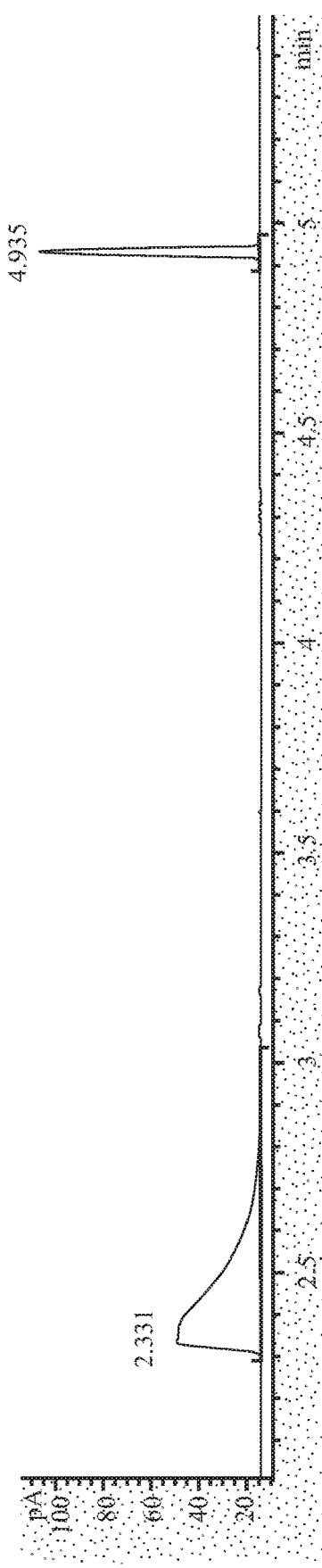
Figure 19B:
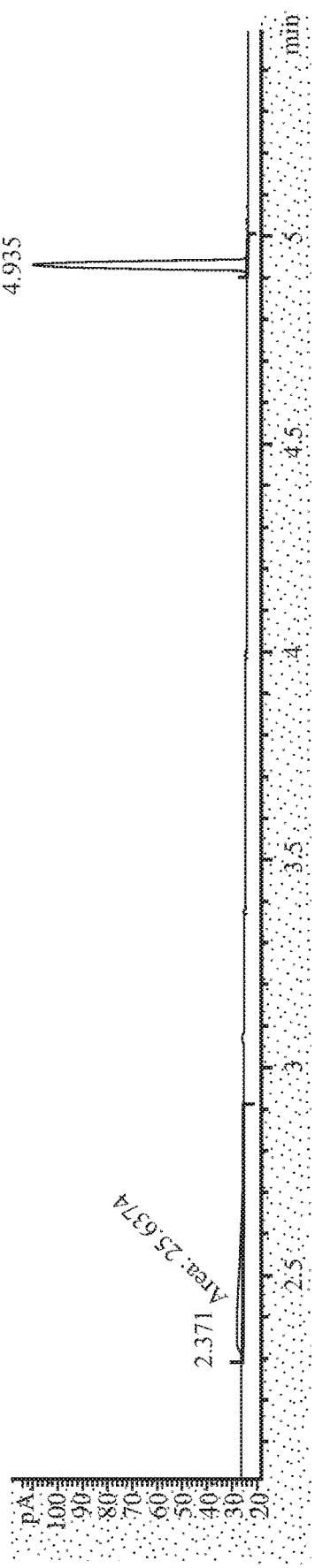
Figure 20A:
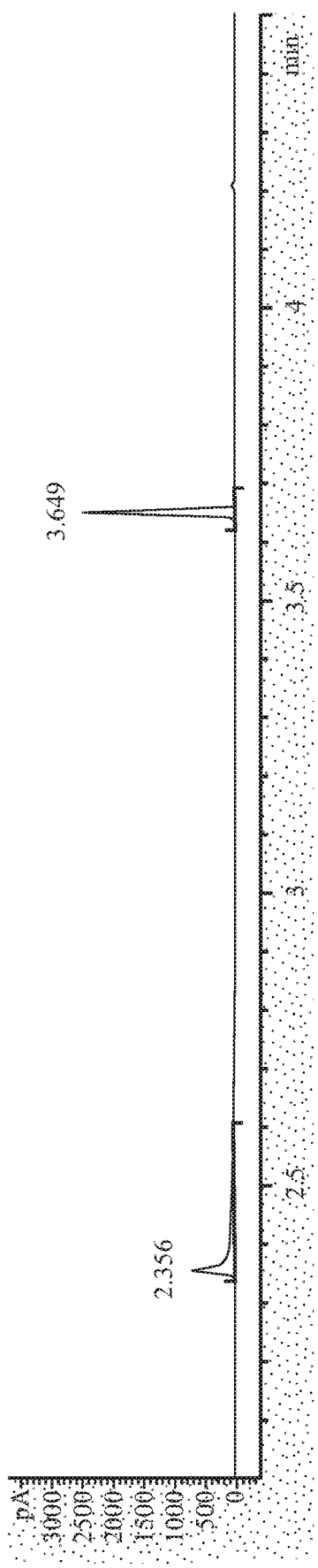
Figure 20B:
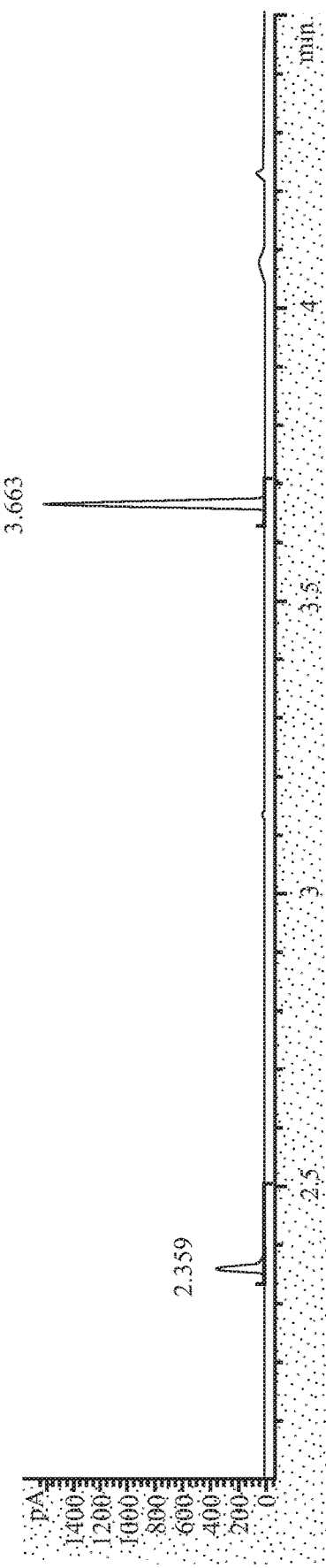
Figure 21A:
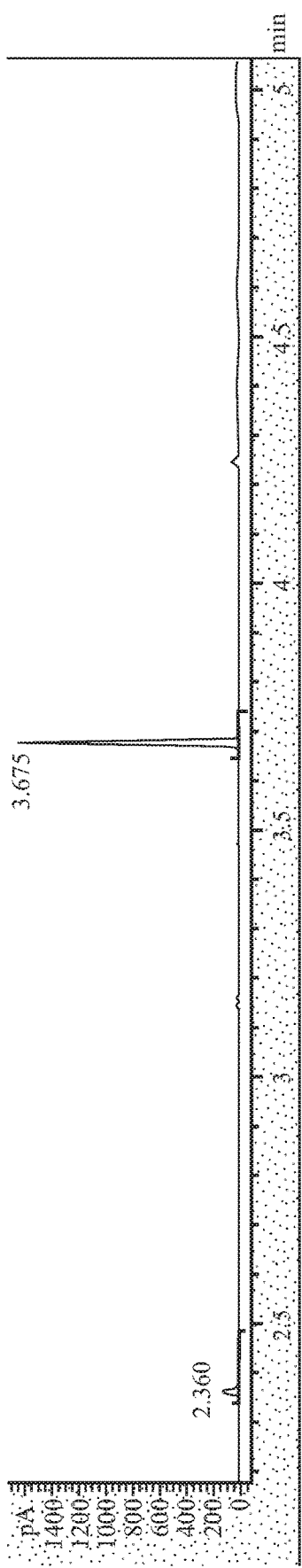
Figure 21B:
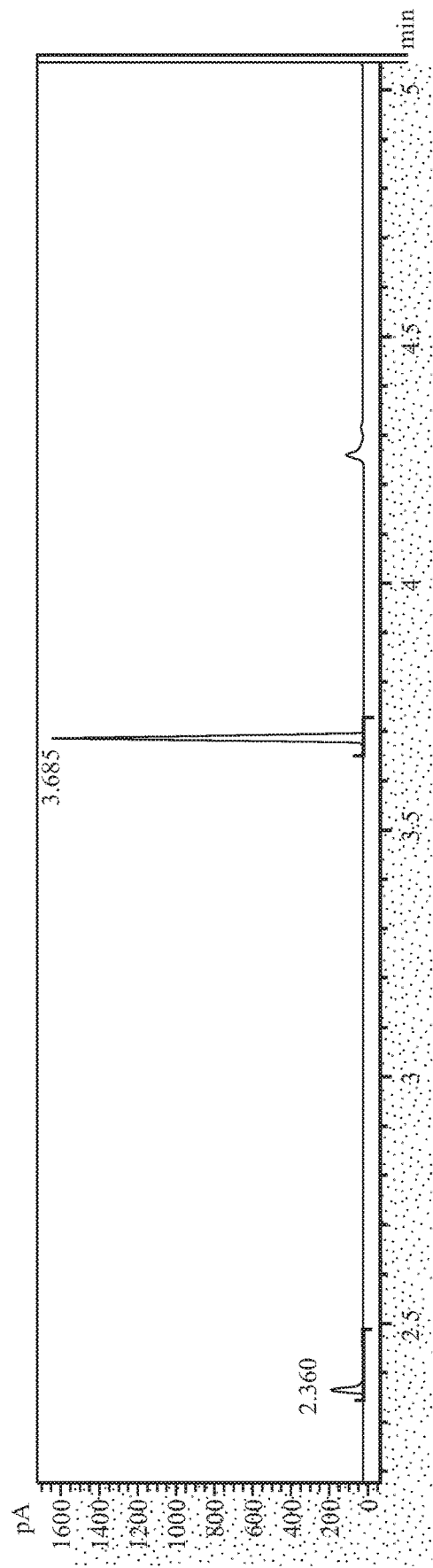

| Entry | OC | Protein Concentration (μM) | SFOC | GC Method | Yield (%) | TTN | GC Trace |
|---|---|---|---|---|---|---|---|
| 1 | 1a | 9 | 2a | A | >99 ± 6.4 | 550 ± 35 | FIG. 11 |
| 2 | 1b | 9 | 2b | B | 94 ± 4.1 | 520 ± 25 | FIG. 12 |
| 3 | 1c | 8.1 | 2c | B | 59 ± 1.3 | 360 ± 10 | FIG. 13 |
| 4 | 1d | 9 | 2d | B | 79 ± 3.7 | 440 ± 20 | FIG. 14 |
| 5 | 1e | 9 | 2e | B | 58 ± 7.6 | 320 ± 40 | FIG. 15 |
| 6 | 1f | 8.1 | 2g | B | 64 ± 2.5 | 400 ± 15 | FIG. 16 |
| 7 | 1g | 9 | 2i | E | 9 ± 1.6 | 50 ± 10 | FIG. 17 |
| 8 | 1h | 9 | 2j | C | 17 ± 1.1 | 95 ± 5 | FIG. 18 |
| 9 | 1i | 9 | 2k | C | 14 ± 0.4 | 80 ± 5 | FIG. 19 |
| 10 | 1j | 9 | 2l | D | 18 ± 1.5 | 100 ± 10 | FIG. 20 |
| 11 | 1j | 0 (Neg. Cont.) | 2l | D | 7 ± 1 | n.a. | FIG. 21 |

OC: Organosilicon compound used in the reaction.
SFOC: Target silanol-functional organosilicon compound being prepared in the reaction.
n.a. = not applicable.

With regard to entry 7, and the GC trace shown in FIG. 19b, the retention time of the Organosilicon Compound 1g (i.e., the starting hydrosilane) is 2.43 min.

Comparative Reactions

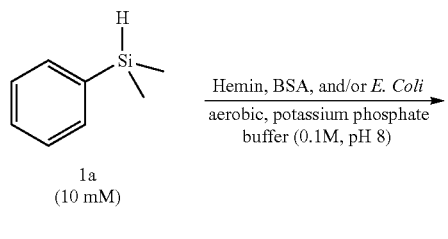

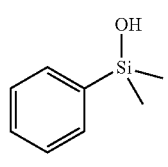

2a

Control reactions were conducted using hemin, bovine serum albumin (BSA), and/or E. coli cells (whole cell or lysate) according to the general reaction procedures set forth above. In particular, the control reactions were performed on a 400-4 scale in potassium phosphate buffer (0.1 M, pH 8) with Organosilicon Compound 1a (10 µL of a 400 mM solution in MeCN, 10 mM final concentration) at room temperature for 4 h. Hemin was added as a 1 mM suspension/solution in MeCN or DMSO (0.4 µL or 4 µL), BSA as a 1 mM solution in potassium phosphate buffer (0.4 µL), and $Na_2S_2O_4$ as a solid (0.9 mg). E. coli cell and lysate reactions were conducted to identify background reactions, and performed with E. cloni EXPRESS BL21(DE3) cells containing a pET22b(+) plasmid encoding a variant of Tryptophane synthase subunit B from Thermotoga maritima (uniprot P50909). E. coli cell lysate was prepared using these E. coli cells, according to the cell lysis procedure above.

All reactions were performed in triplicate (technical replicates), and analyzed via GC-FID according to the procedures set forth above. Particular components, parameters, and results of the control reactions are set forth in Table 13 below, with yields and TTN given as average of the technical replicates.

TABLE 13

Comparative Reactions

| Entry | Catalyst/Additive | Concentration | Yield (%) | TTN |
|---|---|---|---|---|
| 1 | — | — | 0.20 | n.a. |
| 2 | Hemin | 1 µM | 0.20 | n.a. |
| 3 | BSA | 1 µM | 0.20 | n.a. |
| 4 | Hemin + BSA | 1 µM/1 µM | 0.20 | n.a. |
| 5 | Hemin + $Na_2S_2O_4$ | 1 µM/10 mM | 0.20 | n.a. |
| 6 | Hemin + $Na_2S_2O_4$ | 10 µM/10 mM | 1.0 ± 0.1 | 10 ± 1 |
| 7 | Hemin + BSA | 1 µM/1 µM | 0.20 | n.a. |
| 8 | Hemin + BSA + $Na_2S_2O_4$ | 1 µM/1 µM/10 mM | 0.20 | n.a. |
| 9 | E. coli BL21(DE3) | — | 0.30 | n.a. |
| 10 | E. coli lysate | — | 0.30 | n.a. | n.a. = not applicable.

Comparative Substrate Reactions

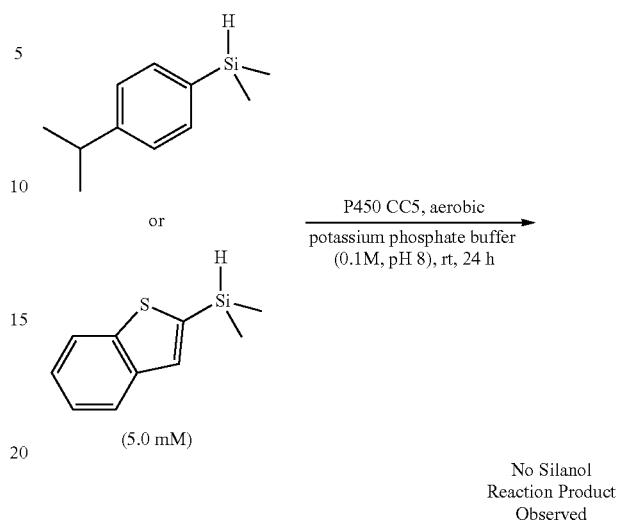

No Silanol Reaction Product Observed

Two small-scale biocatalytic reactions were performed according to the procedure set forth in Reaction Procedure 1 above utilizing two silane compounds, (4-isopropylphenyl)dimethylsilane and (benzothiophen-2-yl)dimethylsilane, individually, and P450 CC5. In particular, pelleted E. coli cells expressing $P450_{SiOx3}$ from 25-50 mL cultures were resuspended in potassium phosphate buffer (5-10 mL, 0.1 M, pH 8), and 390 µL of the mixture were placed in a 2 mL glass GC screw top vial. The silane compound (200 mM in MeCN, 10 µL, 5.0 mM final concentration) was added, and the vial sealed with a cap. After shaking at room temperature and 60 rpm for 24 h, cyclohexane (900 µL) and acetophenone (40 mM in cyclohexane, 20 µL) as internal standard were added. The mixture was vortexed for a few seconds and the phases were separated by centrifugation at 15° C. and 14,000 rpm for 10 min. An aliquot (200 µL) of the organic phase was transferred to a 2 mL glass GC screw top vial with a glass insert. Both reactions were performed in triplicate (technical replicates), and analyzed via GC-FID according to the procedures set forth above. No oxidation product was observed in either reaction.

As will be appreciated from the examples above, a $P450_{BM3}$ variant was engineered to oxidize dimethylphenylsilane (Organosilicon Compound 1a) in E. coli cells under aerobic conditions to prepare a silanol-functional organosilicon compound (i.e., dimethylphenylsilanol, 2a) in 2.1% yield at 1.0 µM protein concentration (i.e., 0.01 mol % catalyst), with 210 TTN (e.g. see Table 10, Entry 1 above). Importantly, no other products were detected. A negligible amount of the silanol-functional organosilicon compound was observed in control reactions under anaerobic conditions and otherwise identical setup containing the $P450_{BM3}$ variant, indicating that oxygen serves as the oxidant (e.g. see Table 10, Entries 2 and 3 above).

With the above results in hand, directed evolution was conducted via sequential rounds of saturation mutagenesis at selected amino acid residues to increase the activity of the enzyme for silane oxidation. In particular, a single-site-saturation mutagenesis (NNK) library was screened in whole E. coli cells (to eliminate the need for addition of the NADPH cofactor) to produce improved variant $P450_{SiOx1}$ containing mutation F87G, which exhibited a 1.5-fold improvement in both yield and TTN under the same conditions as the wild-type enzyme (i.e., the comparative reaction). Further directed evolution conducted via double site-saturation mutagenesis produced improved variant P450$_{SiOx1}$ containing mutations F87G and A328L, which exhibited a further increased yield of 8.5% (850 TTN) in the comparative reaction. An additional round of double site-saturation mutagenesis at another pair of targeted residues produced improved variant P450$_{SiOx3}$, which has mutations F87G, A328L, L181 D, and A328H and exhibits an improved TTN of 1,200 in the comparative reaction.

The performance of the cytochrome P450 variants was assessed in E. coli in both whole-cell and lysate forms, with the latter including a stoichiometric addition of the co-factor NADPH and exhibiting higher turnover numbers (e.g. see Table 10, Entries 7-8). The variant P450$_{SiOx3}$ in particular provided a vast improvement in performance, exhibiting a 3620 TTN (36% yield) compared to 1740 (17% yield) for the wild-type P450$_{BM3}$ in the comparative reaction.

The method was also demonstrated to be compatible across a wide scope of substrates, providing numerous silanol-functional organosilicon compounds in high yields (e.g. see Table 12). For example, Organosilicon Compound 11, a siloxane, was oxidized to the corresponding Silanol-Functional Organosilicon Compound 21, even though uncatalyzed background hydrolysis occurred in significant amounts. Moreover, under certain conditions of the method including increased protein concentrations, lowered substrate concentrations, and particular temperature ranges, provided for the oxidative transformation of Organosilicon Compound 1a to Silanol-Functional Organosilicon Compound 2a in quantitative yield (via GC; 76% isolated yield after 72 h at 37° C.; see Reaction Procedure 2 above).

Notably, moderate or low yields of a silanol reaction product obtained under the particular conditions employed were determined to be consequences of incomplete conversion of the starting hydrosilane, i.e., the organosilicon compound employed. Products of competing C—H or C═C oxidations were not observed. Moreover, no formation of disiloxane byproducts were observed in the examples above, even though such compounds are notorious side products of conventional silanol-producing methods.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

The invention claimed is:

1. A method of preparing a silanol-functional organosilicon compound, said method comprising:
   combining a cytochrome P450 variant that facilitates the oxidization of a silyl hydride group to a silanol group in the presence of oxygen and an organosilicon compound having at least one silicon-bonded hydrogen atom to give a reaction mixture; and
   exposing the reaction mixture to oxygen to oxidize the organosilicon compound, thereby preparing the silanol-functional organosilicon compound.

2. The method of claim 1, wherein the cytochrome P450 variant comprises the amino acid sequence of SEQ ID NO:1 or a conservatively modified variant thereof.

3. The method of claim 1, wherein the cytochrome P450 variant exhibits a total turnover number (TTN) of at least 50.

4. The method of claim 1, wherein the cytochrome P450 variant comprises the amino acid sequence of SEQ ID NO:1 or a conservatively modified variant thereof with a mutation of at least one of F88, A329, L182, and A185 relative to the amino acid sequence of SEQ ID NO:1.

5. The method of claim 4, wherein the cytochrome P450 variant comprises: (i) a F88G mutation; (ii) a A329L mutation; (iii) a L182D mutation; (iv) a A185H mutation; or (v) any combination of (i)-(iv), relative to the amino acid sequence of SEQ ID NO: 1.

6. The method of claim 4, wherein the cytochrome P450 variant exhibits: (i) a higher total turnover number (TTN); (ii) a higher turnover frequency (TOF); or (iii) both (i) and (ii), compared to a wild-type cytochrome P450.

7. The method of claim 6, wherein the cytochrome P450 variant exhibits a TTN of at least 50%, greater than a wild-type cytochrome P450.

8. The method of claim 1, wherein the cytochrome P450 variant exhibits a total turnover number (TTN) greater than 1000.

9. The method of claim 1, wherein the cytochrome P450 variant comprises a non-native heme cofactor.

10. The method of claim 1, wherein preparing the reaction mixture comprises combining the organosilicon compound with a host cell or non-human organism that expresses the cytochrome P450 variant, or a lysate thereof.

11. The method of claim 10, wherein the host cell or non-human organism is transformed or transfected with a nucleic acid comprising the nucleotide sequence of SEQ ID No: 6 or a conservatively modified variant thereof.

12. The method of claim 10, wherein the host cell or non-human organism is transformed or transfected with a polynucleotide comprising the nucleic acid sequence of SEQ ID No: 7 or a conservatively modified variant thereof.

13. The method of claim 10, wherein the host cell or non-human organism is transformed or transfected with a polynucleotide comprising the nucleic acid sequence of SEQ ID No: 8 or a conservatively modified variant thereof.

14. The method of claim 10, wherein the host cell or non-human organism is further defined as an *E. coli* cell.

15. The method of claim 1, wherein the organosilicon compound has the general formula:

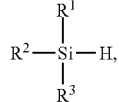

where $R^1$, $R^2$, and $R^3$ are each independently selected from substituted or unsubstituted hydrocarbyl groups, hydrocarbyloxy groups, and siloxy groups.

16. The method of claim 15, wherein each $R^1$, $R^2$, and $R^3$ is independently selected from hydrocarbyl groups having from 1 to 12 carbon atoms, hydrocarbyloxy groups having from 1 to 12 carbon atoms, and siloxy groups of formula $R^4_3SiO-$, where each $R^4$ is an independently selected hydrocarbyl or hydrocarbyloxy group having from 1 to 6 carbon atoms.

17. The method of claim 15, wherein: (i) $R^1$ is an alkyl group having from 1 to 6 carbon atoms; (ii) $R^2$ is an alkyl group having from 1 to 6 carbon atoms, an aryl, alkaryl, or aralkyl group having from 2 to 12 carbon atoms, or an alkenyl group having from 2 to 6 carbon atoms; (iii) $R^3$ is an alkyl group having from 1 to 6 carbon atoms, an aryl, alkaryl, or aralkyl group having from 2 to 12 carbon atoms, an alkenyl group having from 2 to 6 carbon atoms, or a trimethylsiloxy group; or (iv) any combination of (i)-(iii).

18. The method of claim 15, wherein the reaction mixture further comprises: (i) a carrier vehicle; (ii) a buffer; (iii) a reducing agent or cofactor; or (iv) any combination of (i)-(iii).

19. The method of claim 18, wherein: (i) the reaction mixture comprises a concentration of the cytochrome P450 variant of at least 0.1 µM; (ii) the reaction mixture comprises a concentration of the organosilicon compound of from 5 to 10 mM; or (iii) both (i) and (ii).

20. The method of claim 18, wherein the method further comprises: (i) heating the reaction mixture to a temperature of from 30 to 45° C.; (ii) maintaining the pH of the reaction mixture at a pH of about 8; or (iii) both (i) and (ii).

\* \* \* \* \*